United States Patent
De et al.

(10) Patent No.: US 7,989,463 B2
(45) Date of Patent: Aug. 2, 2011

(54) BICCYCLIC COMPOUNDS AS GATA MODULATORS

(75) Inventors: Dibyendu De, Suwanee, GA (US); Ish Kumar Khanna, Alpharetta, GA (US); Sivaram Pillarisetti, Norcross, GA (US)

(73) Assignee: Dr. Reddy's Laboratories Limited, Hyderabad, Andhra Pradesh (IN)

( * ) Notice: Subject to any disclaimer, the term of this patent is extended or adjusted under 35 U.S.C. 154(b) by 0 days.

(21) Appl. No.: 12/553,694

(22) Filed: Sep. 3, 2009

(65) Prior Publication Data

US 2010/0144731 A1    Jun. 10, 2010

Related U.S. Application Data

(60) Provisional application No. 61/190,814, filed on Sep. 3, 2008.

(51) Int. Cl.
*A61K 31/517* (2006.01)
(52) U.S. Cl. ..................... 514/266.4; 544/293
(58) Field of Classification Search ................... 544/293
See application file for complete search history.

(56) References Cited

U.S. PATENT DOCUMENTS

| | | |
|---|---|---|
| 2004/0171073 A1 | 9/2004 | Neiland et al. |
| 2006/0172304 A1 | 8/2006 | Fuchs et al. |
| 2008/0275049 A1 | 11/2008 | Polikandriotis et al. |

FOREIGN PATENT DOCUMENTS

| | | |
|---|---|---|
| WO | 9810090 A1 | 3/1998 |
| WO | 03/078427 A1 | 9/2003 |
| WO | 2007143724 A2 | 12/2007 |
| WO | 2008137533 A1 | 11/2008 |

OTHER PUBLICATIONS

International Searching Authority/European Patent Office, PCT Notification of Transmittal of the International Search Report and the Written Opinion of the International Searching Authority, or the Declaration, date of actual completion Feb. 4, 2010, mailed Feb. 11, 2010, International Application No. PCT/US2009/055926, International Filing Date Sep. 3, 2009.
International Search Report for PCT/US2008/062198 completed Jul. 7, 2008 and mailed Jul. 28, 2008.
GATA-6 Is Involved in PPAR{gamma}-Mediated Activation of Differentiated Phenotype in Human Vascular Smooth Muscle Cells, Mitsuru Abe, et al., Arterioscler Thromb Vas Biol., Mar. 2003, pp. 404-410.

*Primary Examiner* — James O Wilson
*Assistant Examiner* — Brian McDowell
(74) *Attorney, Agent, or Firm* — Balaram Gupta; Robert A. Franks; Thomas C. McKenzie

(57) ABSTRACT

Novel bicyclic compounds of the formula (I), stereoisomers, and/or pharmaceutically acceptable salts of the novel bicyclic compounds, and/or pharmaceutically acceptable salts of the stereoisomers of the novel bicyclic compounds are provided. Additionally, methods of forming novel bicyclic compounds, stereoisomers, and/or pharmaceutically acceptable salts of the novel bicyclic compounds, and/or pharmaceutically acceptable salts of the stereoisomers of the novel bicyclic compounds are provided:

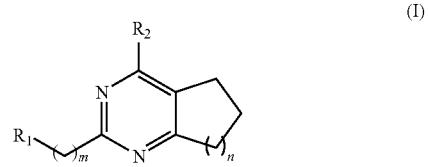

wherein $R_1$, $R_2$, m, and n are defined herein.

15 Claims, No Drawings

BICCYCLIC COMPOUNDS AS GATA MODULATORS

The present application claims priority to U.S. Provisional Patent Application Ser. No. 61/190,814, filed Sep. 3, 2008, which is incorporated herein by reference in its entirety.

BACKGROUND OF THE INVENTION

The present invention relates to novel bicyclic compounds, stereo isomers and/or pharmaceutically acceptable salts thereof.

Atherosclerosis is generally considered an inflammatory disease—with inflammation being the cause of both initiation and progression of the lesion. Without being bound by theory, cholesterol accumulation in macrophages of atherosclerotic lesion (fatty streaks) is believed to be a contributor of localized inflammation and lesion progression. Several types of lipid particles can contribute to the formation of fatty streaks—cholesterol rich low density lipoprotein particles (LDLs) and triglyceride rich very low density lipoproteins (VLDLs) and remnant particles. Cholesterol and other lipids from these particles are typically taken by macrophages in atherosclerotic lesions leading to the formation of lipid-loaded foam cells. Atherosclerotic plaques containing lipid-loaded macrophages are typically inflammatory, are unstable, and are prone to plaque rupture. Acute coronary syndromes (ACS) are often the end manifestations of such plaque rupture, resulting in angina (chest pain), myocardial ischemia (MI, heart attack), fatal MI (sudden death), or stroke. LDL-lowering therapy may allow for remodeling of these plaques, rendering the plaques less prone to rupture. Statin-mediated remodeling processes, however, may take months to years to occur, and hence the benefit of lipid-lowering therapy may not be clinically noticed for several years, as was shown in recent statin prevention trials. Also, although statins are effective at reducing cardiovascular risk, they typically reduce risk by only about one-third over five years. Stabilizing plaque, by reducing cholesterol content or by reducing inflammation, may be important for ACS patients to minimize/prevent reoccurrence of cardiac events.

Cholesterol-loaded macrophages are typically present at all stages of atherosclerosis and are typically abundant in ruptured atherosclerotic plaques. Pathways leading to cholesterol accumulation and egress may determine the physiological (inflammatory/apoptotic) state of the macrophage. Without being bound by theory, macrophage cholesterol is thought to be removed by reverse cholesterol transport (RCT), a process that involves several players including ATP-binding cassette transporters ABCA1 and ABCG1, lecithin cholesterol acyltransferase (LCAT), and scavenger receptor, class B, type I (SR-B1). An increase in the activity of ABCA1, LCAT, and SR-B1, typically results in a boost in the arteries. The ABCA1, LCAT, and SR-B1 genes are, therefore, commonly referred to as reverse cholesterol transport RCT) genes.

Elevated levels of LDL and triglycerides and low levels of HDL are often found in diabetics. This phenotype is referred to as "diabetic dyslipidemia". This condition may result in cholesterol accumulation, especially in tissues that are important in glucose metabolism. Cholesterol accumulation in tissues may lead tissue dysfunction. For example cholesterol accumulation in the pancreas may result in decreased secretion of insulin, the critical hormone required for glucose uptake. Cholesterol accumulation in other tissues, e.g. adipose and skeletal muscle may lead to insulin resistance and, thus, defective glucose uptake in response to insulin. Removal of cholesterol from these tissues will typically have a beneficial effect on insulin resistance, pancreatic function and, thus, is useful for prevention and treatment of diabetes.

GATA can modulate the expression of RCT proteins and pharmacological modulation of GATA can serve as a mechanism for the treatment of atherosclerosis, diabetes and its associated complications (U.S. patent application Ser. No. 12/113,426, incorporated herein by reference in its entirety). GATA transcription factor contains three domains, the C-finger, the N-finger, and the Activation Domain. The C-finger, named for being near the C-terminal, has two highly conserved zinc finger binding domains, which form the Activation Domain that binds the consensus sequence (A/T)GATA (A/G). The N-finger, named for being near the N-terminal also binds DNA and a cofactor named FOG-1. The Activation Domain is responsible for GATA's strong transcriptional activation. The gene for GATA is on the X-chromosome.

SUMMARY OF THE INVENTION

The present invention relates to novel bicyclic compounds having the general formula (I),

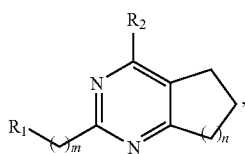

stereoisomers thereof and/or pharmaceutically acceptable salts of compounds of formula (I) and/or pharmaceutically acceptable salts of the stereoisomers of compounds of formula (I); wherein $R_1$ and $R_2$ are each independently selected from —R, —OR, —NR$^a$R$^b$ or

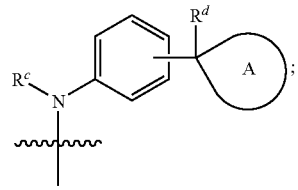

with a proviso that at least one of $R_1$ and $R_2$ is:

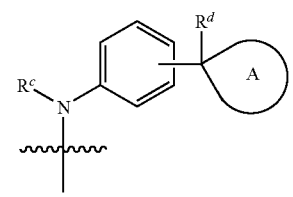

R is selected from an optionally substituted group selected from alkyl, cycloalkyl, aryl, heteroaryl or heterocyclyl, wherein one or more optional substituents on R are selected from halogen, hydroxy, cyano, alkyl, haloalkyl, cycloalkyl, —CO-alkyl, —(CH$_2$)$_p$—OH, —(CH$_2$)$_p$-alkoxy, alkyl, aryl, heteroaryl, —(CH$_2$)$_r$SO$_2$NR$^f$R$^g$ or —(CH$_2$)$_r$SO$_2$R$^h$;

A is a 3 to 7 member cycloalkyl ring;

$R^a$ and $R^b$ are each independently selected from hydrogen, —$(CH_2)_r$—OH, —$(CH_2)_r$-halogen, and an optionally substituted group selected from alkyl, —$(CH_2)_r$-cycloalkyl, —$(CH_2)_r$-heterocyclyl, —$(CH_2)_r$-aryl or —$(CH_2)_r$-heteroaryl, wherein one or more optional substituents on $R^a$ and $R^b$ are each independently selected from halogen, hydroxy, cyano, alkyl, haloalkyl, cycloalkyl, —CO-alkyl, —$(CH_2)_r$—OH, —$(CH_2)_r$-alkoxy, alkyl, aryl, heteroaryl, —$(CH_2)_rSO_2NR^fR^g$ or —$(CH_2)_rSO_2R^h$; or $R^a$ and $R^b$ optionally combine with the nitrogen atom, to which they are attached, to form an optionally substituted 5- to 6-membered heterocyclic ring optionally having 1 to 3 additional hetero atoms or groups selected from nitrogen, oxygen, sulfur, $SO_2$ or CO, wherein one or more optional substituents on the 5- to 6-membered heterocyclic ring are selected from halogen, hydroxy, alkyl, haloalkyl, —CO-alkyl, —$(CH_2)_r$—OH, —$(CH_2)_r$-alkoxy or alkyl;

$R^c$ is selected from hydrogen or alkyl;

$R^d$ is selected from cyano, —$(CH_2)_r$—OH, —$(CH_2)_r$-alkoxy, alkyl, aryl, —NH-aryl, heteroaryl, —$(CH_2)_r$CO-alkyl, —$(CH_2)_rCOOR^e$, —$(CH_2)_rCONR^fR^g$, —$(CH_2)_rSO_2NR^fR^g$ or —$(CH_2)_rSO_2R^h$;

$R^e$ is selected from hydrogen, alkyl, cycloalkyl, aryl, heterocyclyl or heteroaryl;

$R^f$ and $R^g$ are each independently selected from hydrogen or an optionally substituted group selected from alkyl, cycloalkyl, alkoxy, aryl, heteroaryl or heterocyclyl, wherein one or more optional substituents on $R^f$ and $R^g$ are each independently selected from halogen, hydroxyl or alkyl;

$R^h$ is selected from alkyl, cycloalkyl, aryl, heterocyclyl or heteroaryl;

m is an integer from 0-2;

n is an integer from 1-3; and r is an integer from 0 to 3.

In one embodiment, the invention is directed to novel compounds of formula (I), stereoisomers thereof and/or pharmaceutically acceptable salts of compounds of formula (I) and/or pharmaceutically acceptable salts of the stereoisomers of compounds of formula (I) as GATA modulators.

In another embodiment, the invention is directed to novel compounds of formula (I), stereoisomers thereof and/or pharmaceutically acceptable salts of compounds of formula (I) and/or pharmaceutically acceptable salts of the stereoisomers of compounds of formula (I) as RCT activators.

In another embodiment, the invention is directed to a method for the treatment of atherosclerosis, diabetes and its associated complications, Alzheimer's disease and cardiovascular disease in a subject, which comprises administering to the subject a therapeutically effective amount of a compound of formula (I), stereoisomers thereof and/or pharmaceutically acceptable salts of compounds of formula (I) and/or pharmaceutically acceptable salts of the stereoisomers of compounds of formula (I).

DETAILED DESCRIPTION OF THE INVENTION

Reference will now be made in detail to the embodiments of the invention, one or more examples of which are set forth below. Each example is provided by way of explanation of the invention, not limited of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not intended as limiting the broader aspects of the present invention.

The present invention relates to bicyclic compounds having the general formula (I),

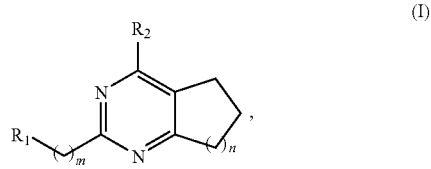

(I)

stereoisomers thereof and/or pharmaceutically acceptable salts of compounds of formula (I) and/or pharmaceutically acceptable salts of the compounds of stereoisomers of formula (I); wherein $R_1$ and $R_2$ are each independently selected from —R, —OR, —$NR^aR^b$ or

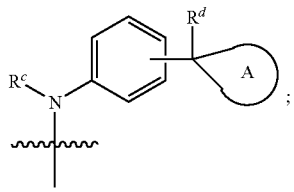

with a proviso that at least one of $R_1$ and $R_2$ is:

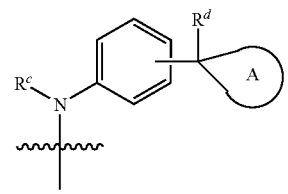

R is selected from an optionally substituted group selected from alkyl, cycloalkyl, aryl, heteroaryl or heterocyclyl, wherein one or more optional substituents on R are selected from halogen, hydroxy, cyano, alkyl, haloalkyl, cycloalkyl, —CO-alkyl, —$(CH_2)_r$—OH, —$(CH_2)_r$-alkoxy, aryl, heteroaryl, —$SO_2NR^fR^g$ or —$SO_2R^h$;

A is a 3 to 7 member cycloalkyl ring;

$R^a$ and $R^b$ are each independently selected from hydrogen, —$(CH_2)_r$-hydroxy, —$(CH_2)_r$-halogen, and an optionally substituted group selected from alkyl, —$(CH_2)_r$-cycloalkyl, —$(CH_2)_r$-heterocyclyl, —$(CH_2)_r$-aryl or —$(CH_2)_r$-heteroaryl, wherein one or more optional substituents on $R^a$ and $R^b$ are each independently selected from halogen, hydroxy, cyano, alkyl, haloalkyl, cycloalkyl, —CO-alkyl, —$(CH_2)_r$—OH, —$(CH_2)_r$-alkoxy, aryl, heteroaryl, —$(CH_2)_rSO_2NR^fR^g$ or —$(CH_2)_rSO_2R^h$; or R$^a$ and R$^b$ optionally combine with the nitrogen atom, to which they are attached, to form an optionally substituted 5- to 6-membered heterocyclic ring optionally having 1 to 3 additional hetero atoms or groups selected from nitrogen, oxygen, sulfur, SO$_2$ or CO, wherein one or more optional substituents on the 5- to 6-membered heterocyclic ring are selected from halogen, hydroxy, alkyl, haloalkyl, —CO-alkyl, —(CH$_2$)$_r$—OH or —(CH$_2$)$_r$-alkoxy;

R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

R$^f$ and R$^g$ are each independently selected from hydrogen or an optionally substituted group selected from alkyl, cycloalkyl, alkoxy, aryl, heteroaryl or heterocyclyl, wherein one or more optional substituents on R$^f$ and R$^g$ are each independently selected from halogen, hydroxyl or alkyl;

R$^h$ is selected from alkyl, cycloalkyl, aryl, heterocyclyl or heteroaryl;

m is an integer from 0-2;

n is an integer from 1-3;

r is an integer from 0 to 3.

In one embodiment, the invention includes compounds of the formula (II),

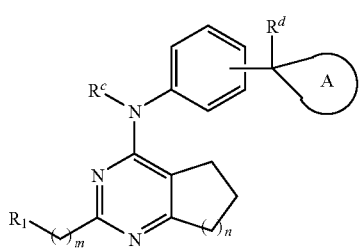

(II)

stereoisomers thereof and/or pharmaceutically acceptable salts of compounds of formula (II) and/or pharmaceutically acceptable salts of the stereoisomers of compounds of formula (II), wherein A, R$_1$, R$^c$, R$^d$, and n are as defined above.

In another embodiment, the invention includes compounds of the formula (III),

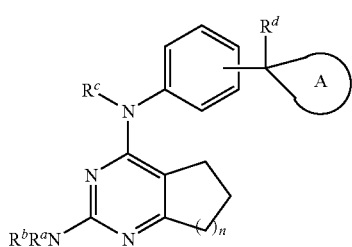

(III)

stereoisomers thereof and/or pharmaceutically acceptable salts of compounds of formula (III) and/or pharmaceutically acceptable salts of the stereoisomers of compounds of formula (III), wherein A, R$_1$, R$^c$, R$^d$, and n are as defined above.

In yet another embodiment, the invention includes compounds of formula (II), wherein A is selected from cyclopropyl, cyclobutyl or cyclopentyl;

R$_1$ is selected from an optionally substituted group selected from alkyl, cycloalkyl, aryl, heteroaryl or heterocyclyl, wherein one or more optional substituents on R$_1$ are selected from halogen, hydroxy, cyano, alkyl, haloalkyl, cycloalkyl, —CO-alkyl, —(CH$_2$)$_r$—OH, —(CH$_2$)$_r$-alkoxy, aryl, heteroaryl, —(CH$_2$)$_r$SO$_2$NR$^f$R$^g$ or —(CH$_2$)$_r$SO$_2$R$^h$;

R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

R$^f$ and R$^g$ are each independently selected from hydrogen or an optionally substituted group selected from alkyl, cycloalkyl, alkoxy, aryl, heteroaryl or heterocyclyl, wherein one or more optional substituents on R$^f$ and R$^g$ are each independently selected from halogen, hydroxyl or alkyl;

R$^h$ is selected from alkyl, cycloalkyl, aryl, heterocyclyl or heteroaryl;

n is an integer selected from 1 or 2; and r is an integer from 0 to 3.

In yet another embodiment, the invention includes compounds of formula (III), wherein A is selected from cyclopropyl, cyclobutyl or cyclopentyl;

R$^a$ is selected from hydrogen or (CH$_2$)$_r$-cycloalkyl;

R$^b$ is selected from hydrogen and an optionally substituted group selected from alkyl, —(CH$_2$)$_r$-cycloalkyl, —(CH$_2$)$_r$-heterocyclyl, —(CH$_2$)$_r$-aryl or —(CH$_2$)$_r$-heteroaryl, wherein one or more optional substituents on R$^b$ are selected from halogen, hydroxy, alkyl, haloalkyl, —CO-alkyl, —(CH$_2$)$_r$—OH, —(CH$_2$)$_r$-alkoxy, —SO$_2$NR$^f$R$^g$ or —SO$_2$R$^h$;

R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

R$^f$ and R$^g$ are each independently selected from hydrogen or an optionally substituted group selected from alkyl, cycloalkyl, alkoxy, aryl, heteroaryl or heterocyclyl, wherein one or more optional substituents on R$^f$ and R$^g$ are each independently selected from halogen, hydroxyl or alkyl;

R$^h$ is selected from alkyl, cycloalkyl, aryl, heterocyclyl or heteroaryl;

n is an integer selected from 1 or 2; and r is an integer from 0 to 3.

In yet another embodiment, the invention includes compounds of formula (III), wherein R$^d$ is COOH.

In another embodiment, the invention includes compounds of formula (III), wherein:

A is selected from cyclopropyl, cyclobutyl or cyclopentyl;

R$^a$ and R$^b$ combine with the nitrogen atom, to which they are attached, to form an optionally substituted 5- to 6-membered heterocyclic ring optionally having 1 to 3 additional hetero atoms or groups selected from nitrogen, oxygen, sulfur, SO$_2$ or CO, wherein one or more optional substituents on the 5- to 6-membered heterocyclic ring are selected from halogen, hydroxy, alkyl, haloalkyl or —CO-alkyl;

$R^c$ is selected from hydrogen or alkyl;

$R^d$ is selected from cyano, —$(CH_2)_r$—OH, —$(CH_2)_r$-alkoxy, alkyl, aryl, —NH-aryl, heteroaryl, —$(CH_2)_r$CO-alkyl, —$(CH_2)_r$COOR$^e$, —$(CH_2)_r$CONR$^f$R$^g$, —$(CH_2)_r$SO$_2$NR$^f$R$^g$ or —$(CH_2)_r$SO$_2$R$^h$;

$R^e$ is selected from hydrogen, alkyl, cycloalkyl, aryl, heterocyclyl or heteroaryl;

$R^f$ and $R^g$ are each independently selected from hydrogen or an optionally substituted group selected from alkyl, cycloalkyl, alkoxy, aryl, heteroaryl or heterocyclyl, wherein one or more optional substituents on $R^f$ and $R^g$ are each independently selected from halogen, hydroxyl or alkyl;

$R^h$ is selected from alkyl, cycloalkyl, aryl, heterocyclyl or heteroaryl;

n is an integer selected from 1 or 2; and r is an integer from 0 to 3.

Another embodiment of the invention comprises compounds of formula (III), wherein $R^d$ is selected from —COOH;

$R^a$ and $R^a$ combine with the nitrogen atom, to which they are attached, to form an optionally substituted morpholinyl, piperidinyl, pyrrolidinyl, piperazinyl, thiomorpholinyl, dioxo-thiomorpholinyl, wherein one or more optional substituents on the heterocyclic ring formed may be selected from halogen, hydroxy, alkoxy, alkyl or —CO-alkyl;

In another embodiment, the invention includes compounds of the formula (IV),

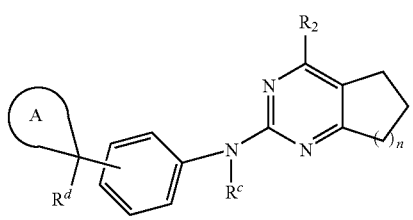

(IV)

stereoisomers thereof and/or pharmaceutically acceptable salts of compounds of formula (IV) and/or pharmaceutically acceptable salts of the stereoisomers of formula (IV), wherein A, $R_2$, $R^c$, and $R^d$ are as defined above.

In another embodiment, the invention includes compounds of the formula (V),

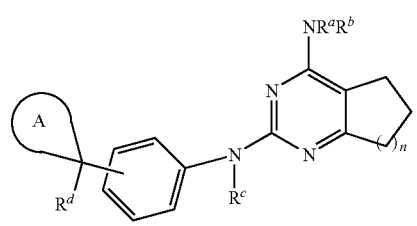

(V)

stereoisomers thereof and/or pharmaceutically acceptable salts of compounds of formula (V) and/or pharmaceutically acceptable salts of the stereoisomers of compounds of formula (V), wherein A, $R_2$, $R^c$, and $R^d$ are as defined above.

In another embodiment, the invention includes compounds of formula (IV), wherein A is selected from cyclopropyl, cyclobutyl or cyclopentyl;

$R_2$ is selected from an optionally substituted group selected from alkyl, cycloalkyl, aryl, heteroaryl or heterocyclyl, wherein one or more optional substituents on $R_2$ are selected from halogen, hydroxy, cyano, alkyl, haloalkyl, cycloalkyl, —CO-alkyl, —$(CH_2)_r$—OH, —$(CH_2)_r$-alkoxy, aryl, heteroaryl, —$(CH_2)_r$SO$_2$NR$^f$R$^g$ or —$(CH_2)_r$SO$_2$R$^h$;

$R^c$ is selected from hydrogen or alkyl;

$R^d$ is selected from cyano, —$(CH_2)_r$—OH, —$(CH_2)_r$-alkoxy, alkyl, aryl, —NH-aryl, heteroaryl, —$(CH_2)_r$CO-alkyl, —$(CH_2)_r$COOR$^e$, —$(CH_2)_r$CONR$^f$R$^g$, —$(CH_2)_r$SO$_2$NR$^f$R$^g$ or —$(CH_2)_r$SO$_2$R$^h$;

$R^e$ is selected from hydrogen, alkyl, cycloalkyl, aryl, heterocyclyl or heteroaryl;

$R^f$ and $R^g$ are each independently selected from hydrogen or an optionally substituted group selected from alkyl, cycloalkyl, alkoxy, aryl, heteroaryl or heterocyclyl, wherein one or more optional substituents on $R^f$ and $R^g$ are each independently selected from halogen, hydroxyl or alkyl;

$R^h$ is selected from alkyl, cycloalkyl, aryl, heterocyclyl or heteroaryl;

n is an integer selected from 1 or 2; and r is an integer from 0 to 3.

In yet another embodiment, the invention includes compounds of formula (V), wherein A is selected from cyclopropyl, cyclobutyl or cyclopentyl;

$R^a$ is selected from hydrogen or $(CH_2)_r$-cycloalkyl;

$R^b$ is selected from hydrogen and an optionally substituted group selected from alkyl, —$(CH_2)_r$-cycloalkyl, —$(CH_2)_r$-heterocyclyl, —$(CH_2)_r$-aryl or —$(CH_2)_r$-heteroaryl, wherein one or more optional substituents on $R^b$ are selected from halogen, hydroxy, alkyl, haloalkyl, —CO-alkyl, —$(CH_2)_r$—OH, —$(CH_2)_r$-alkoxy, —$(CH_2)_r$SO$_2$NR$^f$R$^g$ or —$(CH_2)_r$SO$_2$R$^h$;

$R^c$ is selected from hydrogen or alkyl;

$R^d$ is selected from cyano, —$(CH_2)_r$—OH, —$(CH_2)_r$-alkoxy, alkyl, aryl, —NH-aryl, heteroaryl, —$(CH_2)_r$CO-alkyl, —$(CH_2)_r$COOR$^e$, —$(CH_2)_r$CONR$^f$R$^g$, —$(CH_2)_r$SO$_2$NR$^f$R$^g$ or —$(CH_2)_r$SO$_2$R$^h$;

$R^e$ is selected from hydrogen, alkyl, cycloalkyl, aryl, heterocyclyl or heteroaryl;

$R^f$ and $R^g$ are each independently selected from hydrogen or an optionally substituted group selected from alkyl, cycloalkyl, alkoxy, aryl, heteroaryl or heterocyclyl, wherein one or more optional substituents on $R^f$ and $R^g$ are each independently selected from halogen, hydroxyl or alkyl;

$R^h$ is selected from alkyl, cycloalkyl, aryl, heterocyclyl or heteroaryl;

n is an integer selected from 1 or 2; and r is an integer from 0 to 3.

In yet another embodiment, the invention includes compounds of formula (V), wherein:

$R^d$ is COOH.

In another embodiment, the invention includes compounds of formula (V), wherein:

A is selected from cyclopropyl, cyclobutyl or cyclopentyl;

$R^a$ and $R^b$ combine with the nitrogen atom, to which they are attached, to form an optionally substituted 5- to 6-membered heterocyclic ring optionally having 1 to 3 additional hetero atoms or groups selected from nitrogen, oxygen, sulfur, SO$_2$ or CO, wherein one or more optional substituents on the 5- to 6-membered heterocyclic ring are selected from halogen, hydroxy, alkyl, haloalkyl or —CO-alkyl;

$R^c$ is selected from hydrogen or alkyl;

$R^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

$R^e$ is selected from hydrogen, alkyl, cycloalkyl, aryl, heterocyclyl or heteroaryl;

$R^f$ and $R^g$ are each independently selected from hydrogen or an optionally substituted group selected from alkyl, cycloalkyl, alkoxy, aryl, heteroaryl or heterocyclyl, wherein one or more optional substituents on $R^f$ and $R^g$ are each independently selected from halogen, hydroxyl or alkyl;

$R^h$ is selected from alkyl, cycloalkyl, aryl, heterocyclyl or heteroaryl;

n is an integer selected from 1 or 2; and r is an integer from 0 to 3.

Another embodiment of the invention comprises compounds of formula (IV), wherein:

$R^d$ is —COOH;

$R^a$ and $R^b$ combine with the nitrogen atom, to which they are attached, to form an optionally substituted morpholinyl, piperidinyl, pyrrolidinyl, piperazinyl, thiomorpholinyl, dioxo-thiomorpholinyl, wherein one or more optional substituents on the heterocyclic ring formed may be selected from halogen, hydroxy, alkoxy, alkyl or —CO-alkyl.

In some embodiments, the invention includes compounds of formula (I), which are represented by:

1-[4-(2-Cyclopentyl-6,7-dihydro-5H-cyclopentapyrimidin-4-ylamino)-phenyl]-cyclopentanecarboxylic acid, 1-[4-(2-Cyclopentylmethyl-6,7-dihydro-5H-cyclopentapyrimidin-4-ylamino)-phenyl]-cyclopentanecarboxylic acid, 1-[4-(2-Cyclopentyl-6,7-dihydro-5H-cyclopentapyrimidin-4-ylamino)-phenyl]-cyclobutanecarboxylic acid, 1-[4-(2-Morpholin-4-yl-6,7-dihydro-5H-cyclopentapyrimidin-4-ylamino)-phenyl]-cyclobutanecarboxylic acid, 1-{4-[2-(4-Hydroxy-piperidin-1-yl)-6,7-dihydro-5H-cyclopentapyrimidin-4-ylamino]-phenyl}-cyclobutanecarboxylic acid, 1-[4-(2-Pyrrolidin-1-yl-6,7-dihydro-5H-cyclopentapyrimidin-4-ylamino)-phenyl]-cyclobutanecarboxylic acid, 1-{4-[2-(1-Methyl-1H-pyrazol-4-yl)-6,7-dihydro-5H-cyclopentapyrimidin-4-ylamino]-phenyl}-cyclobutanecarboxylic acid, 1-{4-[2-(4-Fluoro-phenyl)-6,7-dihydro-5H-cyclopentapyrimidin-4-ylamino]-phenyl}-cyclopentanecarboxylic acid, 1-{4-[2-(4-Acetyl-phenyl)-6,7-dihydro-5H-cyclopentapyrimidin-4-ylamino]-phenyl}-cyclobutanecarboxylic acid, 1-[4-(4-tert-Butylamino-6,7-dihydro-5H-cyclopentapyrimidin-2-ylamino)-phenyl]-cyclopentanecarboxylic acid, 1-[4-(4-Cyclopentylamino-6,7-dihydro-5H-cyclopentapyrimidin-2-ylamino)-phenyl]-cyclobutanecarboxylic acid, 1-{4-[2-(3-Fluoro-phenylamino)-6,7-dihydro-5H-cyclopentapyrimidin-4-ylamino]-phenyl}-cyclobutanecarboxylic acid, 1-[4-(2-Cyclopentylamino-6,7-dihydro-5H-cyclopentapyrimidin-4-ylamino)-phenyl]-cyclobutanecarboxylic acid, 1-{4-[2-(Cyclopropylmethyl-amino)-6,7-dihydro-5H-cyclopentapyrimidin-4-ylamino]-phenyl}-cyclobutanecarboxylic acid, 1-{4-[2-(Bis-cyclopropylmethyl-amino)-6,7-dihydro-5H-cyclopentapyrimidin-4-ylamino]-phenyl}-cyclobutanecarboxylic acid, 1-{4-[2-(4-Methanesulfonyl-phenyl)-6,7-dihydro-5H-cyclopentapyrimidin-4-ylamino]-phenyl}-cyclobutanecarboxylic acid, 1-[4-(2-p-Tolyl-6,7-dihydro-5H-cyclopentapyrimidin-4-ylamino)-phenyl]-cyclobutanecarboxylic acid, 1-[4-(2-Phenyl-6,7-dihydro-5H-cyclopentapyrimidin-4-ylamino)-phenyl]-cyclobutanecarboxylic acid, 1-{4-[2-(2-Oxo-pyrrolidin-1-yl)-6,7-dihydro-5H-cyclopentapyrimidin-4-ylamino]-phenyl}-cyclobutanecarboxylic acid methyl ester, 1-{4-[2-(6-Methyl-pyridin-3-yl)-6,7-dihydro-5H-cyclopentapyrimidin-4-ylamino]-phenyl}-cyclobutanecarboxylic acid, {1-[4-(2-Morpholin-4-yl-6,7-dihydro-5H-cyclopentapyrimidin-4-ylamino)-phenyl]-cyclobutyl}-methanol, 1-[4-(2-Morpholin-4-yl-6,7-dihydro-5H-cyclopentapyrimidin-4-ylamino)-phenyl]-cyclopentanecarboxylic acid, {1-[4-(2-Morpholin-4-yl-6,7-dihydro-5H-cyclopentapyrimidin-4-ylamino)-phenyl]-cyclopentyl}-methanol, 1-[4-(4-Morpholin-4-yl-6,7-dihydro-5H-cyclopentapyrimidin-2-ylamino)-phenyl]-cyclobutanecarboxylic acid, Sodium 1-[4-(2-morpholin-4-yl-6,7-dihydro-5H-cyclopentapyrimidin-4-ylamino)-phenyl]-cyclobutanecarboxylate, 1-{4-[2-(4,4-Difluoro-piperidin-1-yl)-6,7-dihydro-5H-cyclopentapyrimidin-4-ylamino]-phenyl}-cyclobutanecarboxylic acid 1-[4-(2-Morpholin-4-yl-5,6,7,8-tetrahydro-quinazolin-4-ylamino)-phenyl]-cyclobutanecarboxylic acid, 1-{4-[4-(3,5-Dimethyl-isoxazol-4-yl)-6,7-dihydro-5H-cyclopentapyrimidin-2-ylamino]-phenyl}-cyclobutanecarboxylic acid, 1-[4-(2-Phenoxy-6,7-dihydro-5H-cyclopentapyrimidin-4-ylamino)-phenyl]-cyclobutanecarboxylic acid, 1-[4-(2-Morpholin-4-yl-6,7-dihydro-5H-cyclopentapyrimidin-4-ylamino)-phenyl]-cyclobutanecarboxylic acid cyclopentylamide, 1-(4-{2-[4-(Pyrrolidine-1-sulfonyl)-phenylamino]-6,7-dihydro-5H-cyclopentapyrimidin-4-ylamino}-phenyl)-cyclobutanecarboxylic acid, 1-[4-(2-Morpholin-4-yl-6,7-dihydro-5H-cyclopentapyrimidin-4-ylamino)-phenyl]-cyclobutanecarbonitrile, 1-[4-(4-Phenoxy-6,7-dihydro-5H-cyclopentapyrimidin-2-ylamino)-phenyl]-cyclobutanecarboxylic acid methyl ester, 1-{4-[4-(Benzyl-ethyl-amino)-6,7-dihydro-5H-cyclopentapyrimidin-2-ylamino]-phenyl}-cyclobutanecarboxylic acid, Sodium 1-{4-[ethyl-(2-morpholin-4-yl-6,7-dihydro-5H-cyclopentapyrimidin-4-yl)-amino]-phenyl}-cyclobutanecarboxylate, stereoisomers thereof and/or pharmaceutically acceptable salts of the compounds and/or pharmaceutically acceptable salts of the stereoisomers of the compounds.

In some embodiments, the invention includes one or more compounds of formula (I), which may be represented by:

1-[4-(2-Cyclopentyl-6,7-dihydro-5H-cyclopentapyrimidin-4-ylamino)-phenyl]-cyclopentanecarboxylic acid, 1-[4-(2-Cyclopentylmethyl-6,7-dihydro-5H-cyclopentapyrimidin-4-ylamino)-phenyl]-cyclopentanecarboxylic acid, 1-[4-(2-Cyclopentyl-6,7-dihydro-5H-cyclopentapyrimidin-4-ylamino)-phenyl]-cyclobutanecarboxylic acid, 1-{4-[2-(4-Fluoro-phenyl)-6,7-dihydro-5H-cyclopentapyrimidin-4-ylamino]-phenyl}-cyclopentanecarboxylic acid, 1-{4-[2-(4-Acetyl-phenyl)-6,7-dihydro-5H-cyclopentapyrimidin-4-ylamino]-phenyl}-cyclobutanecarboxylic acid, 1-{4-[2-(4-Methanesulfonyl-phenyl)-6,7-dihydro-5H-cyclopentapyrimidin-4-ylamino]-phenyl}-cyclobutanecarboxylic acid,
1-[4-(2-p-Tolyl-6,7-dihydro-5H-cyclopentapyrimidin-4-ylamino)-phenyl]-cyclobutanecarboxylic acid,
1-[4-(2-Phenyl-6,7-dihydro-5H-cyclopentapyrimidin-4-ylamino)-phenyl]-cyclobutanecarboxylic acid.

stereoisomers thereof and/or pharmaceutically acceptable salts of the compounds and/or pharmaceutically acceptable salts of the stereoisomers of the compounds.

In some embodiments, the invention includes one or more compounds of formula (I), which may be represented by:
1-[4-(2-Morpholin-4-yl-6,7-dihydro-5H-cyclopentapyrimidin-4-ylamino)-phenyl]-cyclobutanecarboxylic acid,
1-{4-[2-(4-Hydroxy-piperidin-1-yl)-6,7-dihydro-5H-cyclopentapyrimidin-4-ylamino]-phenyl}-cyclobutanecarboxylic acid,
1-[4-(2-Pyrrolidin-1-yl-6,7-dihydro-5H-cyclopentapyrimidin-4-ylamino)-phenyl]-cyclobutanecarboxylic acid,
1-{4-[2-(1-Methyl-1H-pyrazol-4-yl)-6,7-dihydro-5H-cyclopentapyrimidin-4-ylamino]-phenyl}-cyclobutanecarboxylic acid,
1-{4-[2-(2-Oxo-pyrrolidin-1-yl)-6,7-dihydro-5H-cyclopentapyrimidin-4-ylamino]-phenyl}-cyclobutanecarboxylic acid methyl ester,
1-{4-[2-(6-Methyl-pyridin-3-yl)-6,7-dihydro-5H-cyclopentapyrimidin-4-ylamino]-phenyl}-cyclobutanecarboxylic acid,
{1-[4-(2-Morpholin-4-yl-6,7-dihydro-5H-cyclopentapyrimidin-4-ylamino)-phenyl]-cyclobutyl}-methanol,
1-[4-(2-Morpholin-4-yl-6,7-dihydro-5H-cyclopentapyrimidin-4-ylamino)-phenyl]-cyclopentanecarboxylic acid,
{1-[4-(2-Morpholin-4-yl-6,7-dihydro-5H-cyclopentapyrimidin-4-ylamino)-phenyl]-cyclopentyl}-methanol,
Sodium 1-[4-(2-morpholin-4-yl-6,7-dihydro-5H-cyclopentapyrimidin-4-ylamino)-phenyl]-cyclobutanecarboxylate,
1-{4-[2-(4,4-Difluoro-piperidin-1-yl)-6,7-dihydro-5H-cyclopentapyrimidin-4-ylamino]-phenyl}-cyclobutanecarboxylic acid,
1-[4-(2-Morpholin-4-yl-5,6,7,8-tetrahydro-quinazolin-4-ylamino)-phenyl]-cyclobutanecarboxylic acid,
1-[4-(2-Morpholin-4-yl-6,7-dihydro-5H-cyclopentapyrimidin-4-ylamino)-phenyl]-cyclobutanecarboxylic acid cyclopentylamide,
Sodium 1-{4-[ethyl-(2-morpholin-4-yl-6,7-dihydro-5H-cyclopentapyrimidin-4-yl)-amino]-phenyl}-cyclobutanecarboxylate.

stereoisomers thereof and/or pharmaceutically acceptable salts of the compounds and/or pharmaceutically acceptable salts of the stereoisomers of the compounds.

In some embodiments, the invention includes one or more compounds of formula (I), which may be represented by:
1-{4-[2-(3-Fluoro-phenylamino)-6,7-dihydro-5H-cyclopentapyrimidin-4-ylamino]-phenyl}-cyclobutanecarboxylic acid,
1-[4-(2-Cyclopentylamino-6,7-dihydro-5H-cyclopentapyrimidin-4-ylamino)-phenyl]-cyclobutanecarboxylic acid,
1-{4-[2-(Cyclopropylmethyl-amino)-6,7-dihydro-5H-cyclopentapyrimidin-4-ylamino]-phenyl}-cyclobutanecarboxylic acid,
1-{4-[2-(Bis-cyclopropylmethyl-amino)-6,7-dihydro-5H-cyclopentapyrimidin-4-ylamino]-phenyl}-cyclobutanecarboxylic acid,
1-(4-{2-[4-(Pyrrolidine-1-sulfonyl)-phenylamino]-6,7-dihydro-5H-cyclopentapyrimidin-4-ylamino}-phenyl)-cyclobutanecarboxylic acid.

stereoisomers thereof and/or pharmaceutically acceptable salts of the compounds and/or pharmaceutically acceptable salts of the stereoisomers of the compounds.

In some embodiments, the invention includes one or more compounds of formula (I), which may be represented by:
1-[4-(4-Morpholin-4-yl-6,7-dihydro-5H-cyclopentapyrimidin-2-ylamino)-phenyl]-cyclobutanecarboxylic acid,
1-{4-[4-(3,5-Dimethyl-isoxazol-4-yl)-6,7-dihydro-5H-cyclopentapyrimidin-2-ylamino]-phenyl}-cyclobutanecarboxylic acid,
1-[4-(2-Phenoxy-6,7-dihydro-5H-cyclopentapyrimidin-4-ylamino)-phenyl]-cyclobutanecarboxylic acid,
1-[4-(2-Morpholin-4-yl-6,7-dihydro-5H-cyclopentapyrimidin-4-ylamino)-phenyl]-cyclobutanecarbonitrile,
1-{4-[4-(Benzyl-ethyl-amino)-6,7-dihydro-5H-cyclopentapyrimidin-2-ylamino]-phenyl}-cyclobutanecarboxylic acid.

stereoisomers thereof and/or pharmaceutically acceptable salts of the compounds and/or pharmaceutically acceptable salts of the stereoisomers of the compounds.

In some embodiments, the invention includes one or more compounds of formula (I), which may be represented by:
1-{4-[2-(2-Oxo-pyrrolidin-1-yl)-6,7-dihydro-5H-cyclopentapyrimidin-4-ylamino]-phenyl}-cyclobutanecarboxylic acid methyl ester,
{1-[4-(2-Morpholin-4-yl-6,7-dihydro-5H-cyclopentapyrimidin-4-ylamino)-phenyl]-cyclobutyl}-methanol,
1-[4-(2-Morpholin-4-yl-6,7-dihydro-5H-cyclopentapyrimidin-4-ylamino)-phenyl]-cyclopentanecarboxylic acid,
{1-[4-(2-Morpholin-4-yl-6,7-dihydro-5H-cyclopentapyrimidin-4-ylamino)-phenyl]-cyclopentyl}-methanol,
Sodium 1-[4-(2-morpholin-4-yl-6,7-dihydro-5H-cyclopentapyrimidin-4-ylamino)-phenyl]-cyclobutanecarboxylate,
1-{4-[2-(4,4-Difluoro-piperidin-1-yl)-6,7-dihydro-5H-cyclopentapyrimidin-4-ylamino]-phenyl}-cyclobutanecarboxylic acid,
1-[4-(2-Morpholin-4-yl-5,6,7,8-tetrahydro-quinazolin-4-ylamino)-phenyl]-cyclobutanecarboxylic acid,
Sodium 1-{4-[ethyl-(2-morpholin-4-yl-6,7-dihydro-5H-cyclopentapyrimidin-4-yl)-amino]-phenyl}-cyclobutanecarboxylate.

stereoisomers thereof and/or pharmaceutically acceptable salts of the compounds and/or pharmaceutically acceptable salts of the stereoisomers of the compounds.

In one embodiment, the invention is directed to novel compounds of formula (I), stereoisomers thereof and/or pharmaceutically acceptable salts of compounds of formula (I) and/or pharmaceutically acceptable salts of the stereoisomers of compounds of formula (I) as GATA modulators.

In another embodiment, the invention is directed to novel compounds of formula (I), stereoisomers thereof and/or pharmaceutically acceptable salts of compounds of formula (I) and/or pharmaceutically acceptable salts of the stereoisomers of compounds of formula (I) and its stereoisomers as RCT enhancers.

In another embodiment, the invention is directed to a method for the treatment of atherosclerosis, diabetes and its associated complications in a subject, which comprises administering to the subject a therapeutically effective amount of a compound of formula (I), stereoisomers thereof and/or pharmaceutically acceptable salts of compounds of formula (I) and/or pharmaceutically acceptable salts of the stereoisomers of compounds of formula (I) and its stereoisomers.

In another embodiment, the invention is directed to a method for the treatment of diabetic dyslipidemia, Alzheimer's disease and cardiovascular disease in a subject, which comprises administering to the subject a therapeutically effective amount of a compound of formula (I), stereoisomers thereof and/or pharmaceutically acceptable salts of compounds of formula (I) and/or pharmaceutically acceptable salts of the stereoisomers of compounds of formula (I) and its stereoisomers.

In another embodiment, the diabetic-associated complications are those complications known in the art as likely resulting from the diabetic condition. Additionally, diabetic-associated complications are those complications known in the art that are exacerbated by the diabetic condition.

In one embodiment compounds of formula (I), stereoisomers thereof and/or pharmaceutically acceptable salts of compounds of formula (I) and/or pharmaceutically acceptable salts of the stereoisomers of compounds of formula (I) are useful for the treatment of hyperlipidemia, hypercholesterolemia, coronary heart disease, atherosclerosis, diabetes and its associated complications and Alzheimer's disease. The compounds of formula (I) may influence one or more lipid parameters such as increasing the HDL levels, lowering plasma levels of LDL, lowering plasma glucose, and/or lowering triglycerides.

As used herein throughout, the following definitions apply.

The groups defined for various symbols of the compounds of formulae (I)-(V) and optional substituents defined on those groups are defined as follows:

'Halogen or Halo' represents one or more of fluorine, chlorine, bromine, or iodine.

'Alkyl' group refers to linear or branched alkyl groups. Exemplary alkyl groups include one or more of, but are not limited to, methyl, ethyl, n-propyl, iso-propyl, n-butyl, iso-butyl, t-butyl, n-pentyl, iso-pentyl, hexyl, heptyl, octyl and the like. Unless otherwise specified, an alkyl group typically has from 1 to 10 carbon atoms but the invention is not limited in that respect.

'Haloalkyl' means at least one halogen atom is substituted on an alkyl group. Both halogen and alkyl have the meaning as defined above. Representative examples of haloalkyl group include one or more of, but are not limited to, fluoromethyl, chloromethyl, fluoroethyl, chloroethyl, difluoromethyl, trifluoromethyl, dichloroethyl, dichloroethyl and the like. Unless otherwise specified, a halolkyl group typically has from 1 to 10 carbon atoms but the invention is not limited in that respect.

'Cycloalkyl' group refers to a cyclic alkyl group which may be mono, bicyclic, polycyclic or fused bridged ring systems. Exemplary cycloalkyl groups include one or more of, but are not limited to, cyclopropyl, cyclobutyl, cyclopentyl, cyclohexyl, cycloheptyl, cyclooctyl and the like. Unless otherwise specified, a cycloalkyl group typically has from 3 to about 10 carbon atoms but the invention is not limited in that respect. Typical bridged cycloalkyls include, but are not limited to, adamantyl, noradamantyl, bicyclo[1.1.0]butanyl, norboranyl (bicyclo[2.2.1]heptanyl), norbornenyl (bicyclo[2.2.1]heptanyl), norbornadienyl(bicyclo[2.2.1]heptadienyl), bicyclo [2.2.1]heptanyl, bicyclo[3.2.1]octanyl, bicyclo[3.2.1] octanyl, bicyclo[3.2.1]octadienyl, bicyclo[2.2.2]octanyl, bicyclo[2.2.2]octenyl, bicycl0[2.2.2]octadienyl, bicyclo [5.2.0]nonanyl, bicyclo[4.3.2]undecanyl, tricyclo[5.3.1.1] dodecanyl, and the like.

'3 to 7 membered cycloalkyl' group refers to a mono cyclic alkyl group having 3 to 7 carbon atoms. '3- to 7-membered cycloalkyl' groups include one or more of, but are not limited to, cyclopropyl, cyclobutyl, cyclopentyl, cyclohexyl and cycloheptyl.

'Alkoxy' refers to an —O-alkyl group, where alkyl is as defined above. Exemplary alkoxy groups include one or more of, but are not limited to, methoxy, ethoxy, propoxy, butoxy, iso-propoxy, iso-butoxy and the like. Unless otherwise specified, an alkoxy group typically has from 1 to about 10 carbon atoms but the invention is not limited in that respect.

'Aryl' is optionally substituted monocylic or polycyclic aromatic ring system. Exemplary aryl groups include one or more of, but are not limited to, phenyl, naphthyl, and the like. Unless otherwise specified, an aryl group typically has from 6 to about 14 carbon atoms but the invention is not limited in that respect.

'Heteroaryl' is an aromatic monocyclic or polycyclic ring system, having at least one heteroatom or heterogroup selected from —O—, —N—, —S—, —SO$_2$, or —CO but the invention is not limited in that respect. Exemplary heteroaryl groups include one or more of, but are not limited to, pyrazinyl, isothiazolyl, oxazolyl, isooxazolyl, pyrazolyl, pyrrolyl, pyridazinyl, thienopyrimidyl, furanyl, indolyl, isoindolyl, benzo[1,3]dioxolyl, 1,3-benzoxathiole, pyrrolidine 2,4-dione, quinazolinyl, pyridyl, thiophenyl, and the like. Unless otherwise specified, a heteroaryl group typically has from 4 to about 10 carbon atoms but the invention is not limited in that respect.

'Heterocyclyl' is a non-aromatic saturated monocyclic or polycyclic ring system of 3 to 10 member having at least one heteroatom or heterogroup selected from one or more of —O—, —N—, —S—, —SO$_2$, or —CO but the invention is not limited in that respect. Exemplary heterocyclyl groups include one or more of, but not limited to, pyrrolidinyl, piperidinyl, piperazinyl, morpholinyl, thiomorpholinyl, thiomorpholine 1,1-dioxide, thiazolidinyl, 1,3-dioxolanyl, 1,4-dioxanyl, and the like. Unless otherwise specified, a heterocyclyl group typically has from 3 to about 10 carbon atoms but the invention is not limited in that respect.

'5- to 6-Membered heterocyclic ring' is a saturated monocyclic ring system of with 5 or 6 ring atoms, having at least one heteroatom selected from nitrogen atom. The said rings may optionally contain additional 1 to 2 heteroatoms or heterogroups selected from one or more of —O—, —N—, —S—, —SO$_2$, or —CO but the invention is not limited in that respect. Exemplary '5- to 6-membered heterocyclyl' groups include one or more of, but are not limited to, pyrrolidinyl, piperdinyl, piperazinyl, morpholinyl, thiomorpholinyl, thiomorpholine 1,1-dioxide and the like.

'Optionally substituted' means that substitution is optional and, therefore, it is possible for the designated atom or molecule to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is keto (i.e., =O), then 2 hydrogens on the atom are replaced and when the substitution is fluoro, then 1 hydrogen on the atom is replaced and the like.

The one or more compounds of formula (I) can be supplied in the form of a novel therapeutic composition that is within the scope of the present invention.

'Salts' refer to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the invention. The preparation of salts can be carried out using known methods.

For example, pharmaceutically acceptable salts of compounds contemplated herein may be synthesized by conventional chemical methods using a parent compound containing a base or an acid residue. Generally, such salts may be prepared, for example, by making free acid or base forms of the compounds and reacting with a stoichiometric quantity of the appropriate base or acid in water or in an organic solvent, or in a mixture of the two. Generally, non-aqueous media such as one or more of ether, ethyl acetate, ethanol, isopropanol or acetonitrile may be utilized. Examples of acid addition salts include one or more of, but are not limited to, mineral acid addition salts such as hydrochloride, hydrobromide, hydroiodide, sulphate, nitrate, phosphate, and organic acid addition salts such as acetate, maleate, fumarate, citrate, oxalate, succinate, tartrate, malate, mandelate, methanesulphonate and p-toluenesulphonate. Examples of base addition salts include one or more of, but are not limited to, inorganic salts such as sodium, potassium, calcium, ammonium, magnesium, and lithium salts, and organic base salts such as ethylenediamine, ethanolamine, N,N-dialkyl-ethanolamine, triethanolamine, glucamine and basic amino acid salts.

Also included in present invention are the isomeric forms and tautomers and the pharmaceutically-acceptable salts of compounds of formula (I). Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, $\beta$-hydroxybutyric, galactaric and galacturonic acids.

Suitable pharmaceutically-acceptable base addition salts of compounds of the present invention include metallic ion salts and organic ion salts. Commonly used metallic ion salts include one or more of, but are not limited to, appropriate alkali metal (Group IA) salts, alkaline earth metal (Group IIA) salts, and other physiological acceptable metal ions. Such salts can be made from one or more of the ions of aluminum, calcium, lithium, magnesium, potassium, sodium and zinc. Exemplary organic salts can be made from one or more of tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts may be prepared by those skilled in the art by conventional means from the corresponding compound of the present invention.

For any particular compound disclosed herein, any general structure presented also encompasses all conformational isomers, regioisomers, stereoisomers and tautomers that may arise from a particular set of substituents.

Compounds of formula (I) contain more than one asymmetric carbons. It is to be understood accordingly that the stereoisomers arising from such asymmetry (e.g., all enantiomers and diastereomers) are included within the scope of this invention, unless explicitly indicated otherwise. Such isomers can be obtained in substantially pure form by classical separation techniques and by stereochemically controlled synthesis.

Contemplated derivatives are those that increase the bioavailability of the compounds of this invention when such compounds are administered to a subject e.g., by making an orally administered compound more easily absorbed. Formulae (I)-(V) compounds can be amorphous, semi-crystalline, or crystalline and may be given as parent compounds, its salts, and/or in solvated form. The solvate may be part of a crystalline lattice or superficially associated. It is intended that all of these forms should be within the scope of the present invention. Methods of solvation are generally known within the art. Suitable solvates are pharmaceutically acceptable solvates. In one embodiment, the solvate is a hydrate.

The GATA family of transcription factors is known to include GATA1, GATA2, GATA3, GATA4, GATA5, and GATA6. As used herein, the term GATA shall be interpreted as including one or more of the GATA family of transcription factors unless explicitly stated otherwise.

As used herein, the term 'subject' means mammals, such as humans and other animals, including horses, dogs, cats, rats, mice, sheep, pigs, etc. In exemplary embodiments, the subject may include subjects for which treatment and/or prevention of the conditions described herein would be beneficial.

For ease of reference, the present invention will be described in terms of administration to human subjects. It will be understood, however, that such descriptions are not limited to administration to humans, but will also include administration to other animals unless explicitly stated otherwise.

The phrase 'therapeutically effective' indicates the capability of an agent to prevent, or improve the severity of, the disorder, while avoiding adverse side effects typically associated with alternative therapies.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. Besides being useful for human treatment, these combinations are also useful for treatment of other mammals, including horses, dogs, cats, rats, mice, sheep, pigs, etc.

The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful or potentially useful in producing at least one physiological response in a subject to which such pharmaceutical composition is administered.

The pharmaceutical compositions of compounds of formulae (I)-(V) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present invention may be administered in a wide variety of different dosage forms. For example, they may be combined with various pharmaceutically acceptable inert carriers in the form of one or more of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include one or more of solid diluents or fillers, sterile aqueous media, and various nontoxic organic solvents, etc. Moreover, oral pharmaceutical compositions may be sweetened and/or flavored. In general, the compounds of the invention may be present in such dosage forms at concentration levels ranging from about 0.1% to about 90% by weight.

For oral administration, tablets may contain various excipients such as one or more of microcrystalline cellulose, sodium citrate, calcium carbonate, dicalcium phosphate and glycine may be employed along with various disintegrants such as starch (such as corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulphate and talc may be employed. Solid compositions of a similar type may also be employed as fillers in gelatin capsules; exemplary materials in this connection may also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents, together with diluents such as water, ethanol, propylene glycol, glycerin and various combinations thereof.

For parenteral administration (including intraperitoneal subcutaneous, intravenous, intradermal or intramuscular injection), solutions of compounds of the present invention in, for example, either sesame or peanut oil or in aqueous propylene glycol may be employed. The aqueous solutions may be buffered, if necessary or desirable, and the liquid diluent first rendered isotonic. These aqueous solutions may be suitable for intravenous injection purposes. The oily solutions may be suitable for intraarticular, intramuscular, and/or subcutaneous injection purposes. The preparation of such solutions under sterile conditions may be accomplished by standard pharmaceutical techniques known to those having ordinary skill in the art. For parenteral administration, examples of suitable preparations may include solutions, such as oily or aqueous or non-aqueous solutions, as well as suspensions, emulsions, and/or implants, including suppositories. Compounds of the present invention may be formulated in sterile form in multiple or single dose formats. For example, the compounds of the present invention may be dispersed in a fluid carrier such as sterile saline and/or 5% saline dextrose solutions commonly used with injectables.

In another embodiment, the compounds of the present invention may be administered topically. For example, it may be desirable to administer the compounds of the present invention topically when treating inflammatory conditions of the skin. Non-limiting examples of methods of topical administration include transdermal, buccal, or sublingual application. For topical applications, therapeutic compounds may be suitably admixed in a pharmacologically inert topical carrier such as a gel, an ointment, a lotion, and/or a cream. Such topical carriers may include water, glycerol, alcohol, propylene glycol, fatty alcohols, triglycerides, fatty acid esters, and/or mineral oils. Other possible topical carriers may include liquid petrolatum, isopropylpalmitate, polyethylene glycol, ethanol 95%, polyoxyethylene monolaurate 5% in water, sodium lauryl sulphate 5% in water, and the like, and combinations thereof. In addition, materials such as surfactants, anti-oxidants, humectants, viscosity stabilizers, and the like, and combinations thereof, also may be added if desired.

It will be appreciated by those having ordinary skill in the art that the exemplary amounts of active compounds used in a given therapy will vary according to the specific compound being utilized, the particular compositions formulated, the mode of application, the particular site of administration, etc. Optimal administration rates for a given protocol of administration may be ascertained by those having ordinary skill in the art using conventional dosage determination tests conducted with regard to the foregoing guidelines.

In general, compounds of the present invention for treatment may be administered to a subject in a suitable effective dose of one or more compounds of the present invention may be in the range of from about 0.01 to about 100 milligrams per kilogram of body weight of recipient per day, in some embodiments, in the range of from about 0.5 to about 50 milligrams per kilogram body weight of recipient per day, in still other embodiments, in the range of from about 0.1 to about 20 milligrams per kilogram body weight of recipient per day. The exemplary dose may be suitably administered once daily, or several sub-doses, e.g. 2 to 5 sub-doses, may be administered at appropriate intervals through the day, or other appropriate schedule.

EXAMPLES

An embodiment of the present invention provides preparation of the novel compounds of formulae (I)-(V) according to the procedure of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention claimed herein. All temperatures are in degrees Celsius unless otherwise noted.

The following acronyms, abbreviations, terms and definitions have been used throughout the reaction scheme and experimental section.

Acronyms or Abbreviations:

DMF (N,N-dimethylformamide), DMSO (dimethyl sulfoxide), MeOH (methanol), EtOH (ethanol), EtOAc (Ethyl Acetate), $CD_3OD$ (deuterated Methanol), $Na_2SO_4$ (sodium sulfate), $K_2CO_3$ (potassium carbonate), $CDCl_3$ (deuterated chloroform), mmol (milli mole), mL (milliliters), MP (melting point), min (minute), g (grams), µL (micro liter), MS (mass spectroscopy/spectrometry), IR (infrared), NMR (nuclear magnetic resonance), TLC (thin layer chromatography), HPLC (high performance liquid chromatography).

NMR abbreviations: br (broad), bs (broad singlet), apt (apparent), s (singlet), d (doublet), t (triplet), q (quartet), dd (doublet of doublets), m (multiplet).

The compounds of formula (I) can be synthesized by following any of the processes explained in following schemes, wherein all symbols are as defined earlier:

The following general schemes describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

The compound of formula (I) can be synthesized by following any of the process explained in following General Scheme A to E, wherein all symbols/variables are as defined earlier:

Preparation A

General Synthesis of Amidines

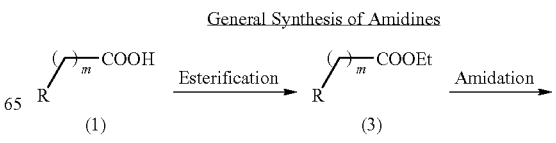

-continued

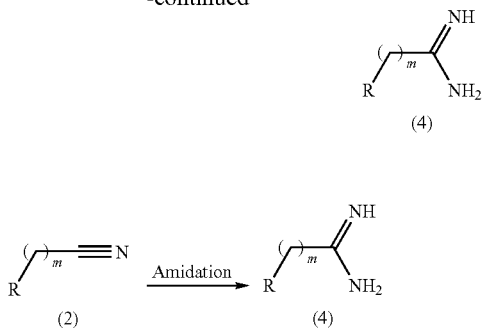

An amidine of general formula (4) cab be synthesized according to general preparation A from commercially available carboxylic acid of general formula (1) or carbonitrile of general formula (2), wherein R and m are the same as defined in compound of formula (I).

In general, an alkyl ester of general formula (3) such as methyl ester, ethyl ester and the like, or an alkyl or aryl carbonitrile of general formula (2) can be treated with methylchloroaluminum amide (MeAl(Cl)NH$_2$), (ref: Gielen, H. et. al *Tetrahedron Letters,* 2002, 43, 419-421) freshly prepared from ammonium chloride and commercially available trimethylaluminum in an organic solvent such as toluene and the like, at a temperature ranging from about 0° C. to 25° C. After heating the reaction mixture at a temperature of about 50° C. to 120° C. for about 4-20 hours followed by work up, the product (amidine) of general formula (4) can be isolated as either a base or a hydrochloride salt.

Preparation B

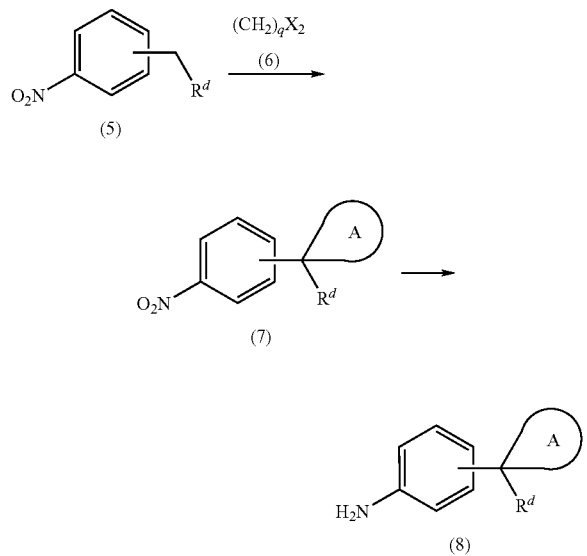

Spiroamines of general formula (8) can be synthesized according to general preparation B from a compound of general formula (5), wherein $R^d$ represents carboxylic esters and carbonitriles.

In general, a nitroarylacetic acid ester of general formula (5), wherein $R^d$ is —COOR$^e$, R$^e$ is the same as defined in compound of formula (I), can be treated with a dihaloalkane of general formula (6), wherein q is 2-6, inclusive and X represents a halogen; such as dibromoethane, dibromopropane, dibromobutane, dibromopentane, diiodoethane, diiodopropane, diiodobutane, diiodopentane and the like, in the presence of a base such as sodium hydride, potassium hydride, sodium tert-butoxide, sodium methoxide, lithium diisopropylamine and the like; and in a polar aprotic solvent such as dimethyl formamide, dimethylacetamide and the like, at a temperature ranging from about 0 to 5° C. followed by stirring at about 20 to 35° C. for about 6-18 hours. Thereafter, aqueous work-up followed by chromatography purification or crystallization can afford nitroarylcycloalkylester of general formula (7), wherein A is the same as defined in compound of formula (I), which can be subsequently reduced by metal halides such as tin chloride or hydrogenation in the presence of a metal catalyst such as palladium-carbon to produce a spiroamine of general formula (8), wherein A is the same as defined in compound of formula (I), $R^d$ represents —COOR$^e$, wherein R$^e$ is the same as defined in compound of formula (I).

Alternatively, a solution of nitroarylacetic acid ester of general formula (5), wherein $R^d$ represents —COOR$^e$ and R$^e$ is the same as defined in compound of formula (I), can be treated with a dihaloalkane of general formula (6), wherein q is 2-6, inclusive and X represents a halogen; such as dibromoethane, dibromopropane, dibromobutane, dibromopentane, diiodoethane, diiodopropane, diiodobutane, diiodopentane and the like; in the presence of a base such as potassium carbonate, sodium carbonate, cesium carbonate and the like; and a phase transfer catalyst such as tetrabutylammoniumhydrogen sulfate, in a polar solvent such as acetonitrile and the like, at about the reflux temperature of the solvent for about 8-20 hours. Thereafter, aqueous work-up followed by column chromatography purification or crystallization could afford nitroarylcycloalkylester of general formula (7), wherein A is the same as defined in compound of formula (I). Subsequent reduction by metal halides such as tin chloride or hydrogenation in the presence of a metal catalyst such as palladium-carbon can produce a spiroamine of general formula (8), wherein A is the same as defined in compound of formula (I), wherein $R^d$ represents —COOR$^e$ and R$^e$ is the same as defined in compound of formula (I).

Similarly, a solution of nitrophenylacetonitrile of general formula (5), wherein $R^d$ represents a cyano group, could be treated with a dihaloalkane of general formula (6), wherein p=2 to 6, inclusive and X represents a halogen; such as dibromoethane, dibromopropane, dibromobutane, dibromopentane, diiodoethane, diiodopropane, diiodobutane, diiodopentane and the like; in the presence of a base such as potassium carbonate, sodium carbonate, cesium carbonate and the like; and a phase transfer catalyst such as tetrabutylammoniumhydrogen sulfate and the like, in a polar solvent such as acetonitrile and the like, at about the reflux temperature of the solvent for about 8-20 hours. Thereafter, aqueous work up followed by column chromatography purification could afford nitroarylcycloalkylnitrile of general formula (7), wherein A is the same as defined in compound of formula (I) and $R^d$ represents a cyano group. Reduction of nitroarylcycloalkylnitrile of general formula (7), by a metal halide such as tin chloride can afford a spiroamine of general formula (8), wherein A is the same as defined in compound of formula (I) and $R^d$ represents a cyano group.

Scheme I

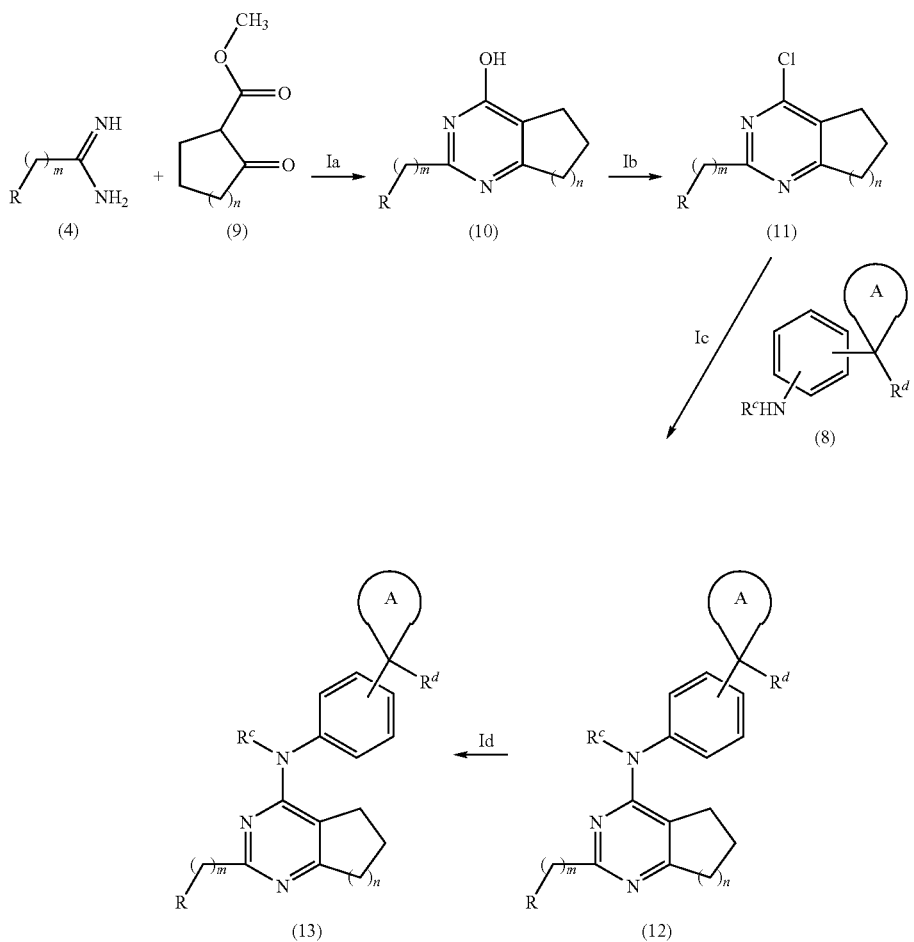

Pathway Ia: A compound of general formula (4), wherein R and m are same the as defined in compound of formula (I), can be condensed with commercially available methyl-2-oxo-cycloalkanecarboxylate of general formula (9), wherein n is the same as defined in compound of formula (I), by heating in a polar solvent such as ethanol and the like, at a temperature ranging from about 15 to 100° C. for about 6-20 hours. After aqueous work up, the compound of general formula (10) can be obtained.

Pathway Ib: Chlorination of a compound of general formula (10), wherein R, m and n are same the as defined in compound of formula (I), using phosphorus oxychloride can yield a compound of general formula (11).

Pathway Ic: Reacting a compound of general formula (11), wherein R, m and n are the same as defined in compound of formula (I), with a spiroamine of general formula (8), wherein $R^c$ and A are the same as defined in compound of formula (I), wherein $R^d$ represents —COOR$^e$, $R^e$ is the same as defined in compound of formula (I), in the presence of a polar solvent such as 2-propanol, 1-butanol and the like, at a temperature ranging from about 50 to 120° C. for about 6-18 hours followed by work up can yield a compound of general formula (12).

Pathway Id: Base catalyzed hydrolysis of a compound of general formula (12) wherein A, R, $R^c$, m and n are the same as defined in compound of formula (I), $R^d$ represents —COOR$^e$, wherein $R^e$ is the same as defined in compound of formula (I), using alkali metal hydroxides such as sodium hydroxide, potassium hydroxide and the like, in a polar solvent such as methanol, ethanol, 2-propanol, tetrahydrofuran and the like, and often in the presence of water as a co-solvent at a temperature ranging from about 20 to 100° C. followed by acid work up could afford the corresponding acid (13), wherein $R^d$ represents —COOH.

Scheme II

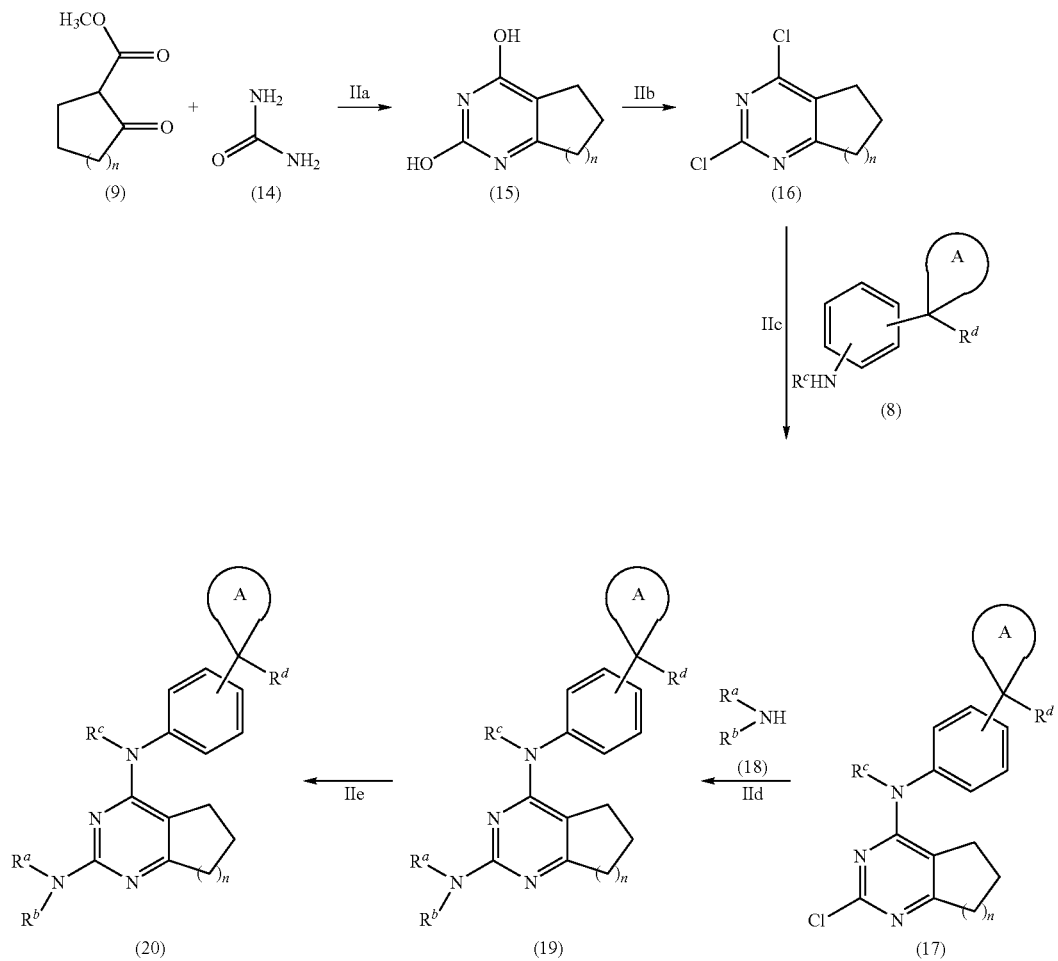

Pathway IIa: A compound of general formula (9), wherein n is the same as defined as defined in compound of formula (I), can be treated with urea (14) in the presence of an activating agent such as chlorotrimethylsilane in a polar solvent such as dimethylformamide and the like, at a temperature of about 0 to 45° C. in an inert atmosphere followed by stirring at a temperature in the range of about 15 to 40° C. for about 24-48 hours. After an aqueous work up, a solid could be isolated, which, without further purification, could be treated with an alkaline solution at an elevated temperature of about 50° C.-100° C. for about 2-6 hours, followed by an acidic work up to yield the compound of general formula (15).

Pathway IIb: Chlorination of a compound of general formula (15) using phosphorus oxychloride at an elevated temperature of about 50-110° C. can afford a compound of general formula (16).

Pathway IIc: Reacting a compound of general formula (16), wherein n is the same as defined in compound of formula (I), with a spiroamine of general formula (8), wherein $R^c$ and A are the same as defined in compound of formula (I), $R^d$ represents —COOR$^e$, wherein $R^e$ is the same as defined in compound of formula (I), in a polar solvent such 2-propanol, 1-butanol and the like, at a temperature ranging from about 10 to 120° C. for about 6-18 hours followed by work up can afford a compound of general formula (17).

Pathway IId: Amination of a compound of general formula (17), wherein A, $R^c$, n are the same as defined in compound of formula (I), $R^d$ represents —COOR$^e$, wherein $R^e$ is the same as defined in compound of formula (I), with an amine of general formula (18), wherein $R^a$ and $R^b$ are the same as defined in compound of formula (I), followed by work up can afford a compound of general formula (19).

Pathway IIe: Base catalyzed hydrolysis of compound (19), wherein A, $R^a$, $R^b$, and $R^c$ are the same as defined in compound of formula (I), $R^d$ represents —COOR$^e$, wherein $R^e$ is the same as defined in compound of formula (I); using a procedure as described in Pathway Id, can afford the compound of formula (20) wherein $R^d$ represents —COOH.

Scheme III

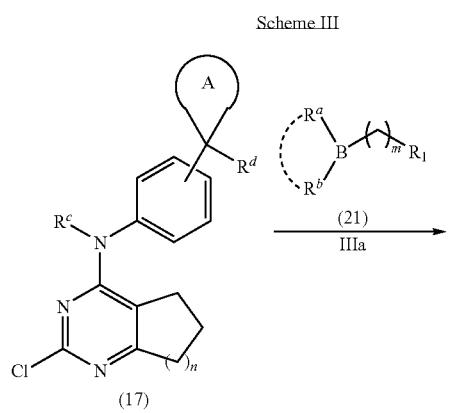

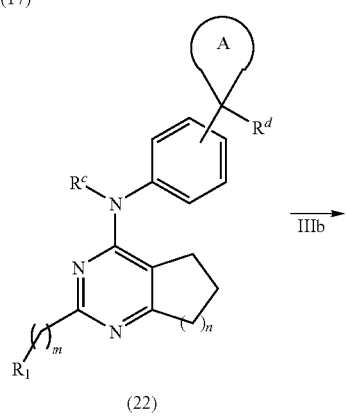

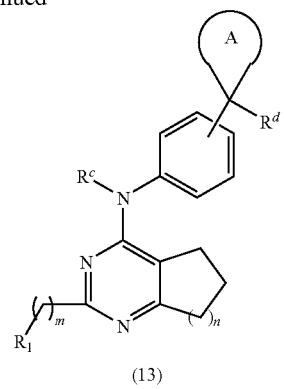

Pathway IIIa: Palladium catalyzed reaction of a compound of general formula (17), wherein A, $R^c$, n are same as in the description of compound of general formula (I), $R^d$ represents —$COOR^e$ wherein $R^e$ represents an alkyl group; with boron compound of general formula (21), wherein $R_1$ and m are same as in the description of compound of general formula (I), $R^a$, $R^b$ represent aryl, heterocyclyl or heteroaryl group, in the presence of a base such as sodium carbonate, potassium carbonate, cesium carbonate and the like, in an inert atmosphere, followed by work up and chromatography purification can afford a compound of general formula (22), wherein $R_1$ and m are the same as defined in compound of formula (I).

Pathway IIIb: Base catalyzed hydrolysis of a compound of general formula (22) using a procedure as described in Pathway Id, can afford a compound of general formula (13), wherein $R^d$ is —COOH.

Scheme IV

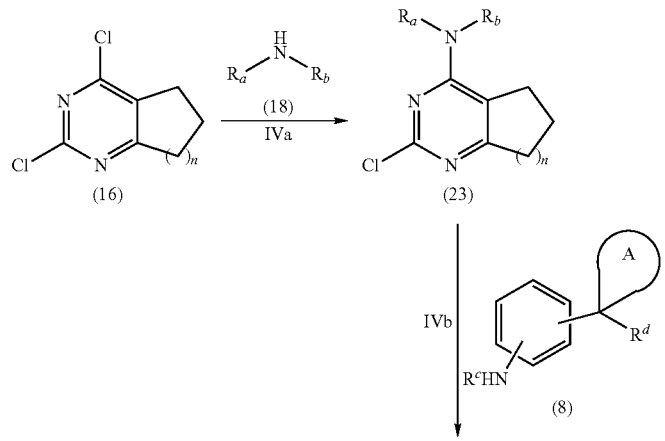

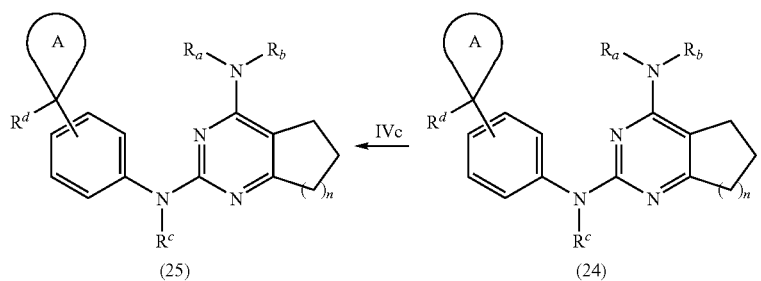

Pathway IVa: Condensation of a compound of general formula (16), wherein n is the same as defined in compound of general formula (I), with a compound of general formula (18), wherein $R^a$ and $R^b$ are the same as defined in compound of formula (I) at an elevated temperature followed by work up and chromatography purification can afford a compound of general formula (23) wherein $R_a$, $R_b$ and n are the same as defined in compound of formula (I).

Pathway IVb: Reacting a compound of general formula (23), wherein $R^a$, $R^b$ and n are the same as defined in compound of formula (I), with a spiroamine of general formula (8), wherein $R^c$ and A are the same as defined in compound of formula (I), $R^d$ represents —COOR$^e$, wherein $R^e$ is the same as defined in compound of formula (I), in a polar solvent such 2-propanol, 1-butanol and the like, at a temperature of about 50-120° C. for about 6-18 hours followed by work up, can afford a compound of general formula (24).

Pathway IVc: Base catalyzed hydrolysis of a compound of general formula (24), wherein A, $R^a$, $R^b$, $R^c$ and n are the same as defined in compound of formula (I), $R^d$ represents —COOR$^e$, wherein $R^e$ is the same as defined in compound of formula (I), using a procedure as described in Pathway Id, can afford a compound of general formula (25), wherein $R^d$ is —COOH.

Scheme V

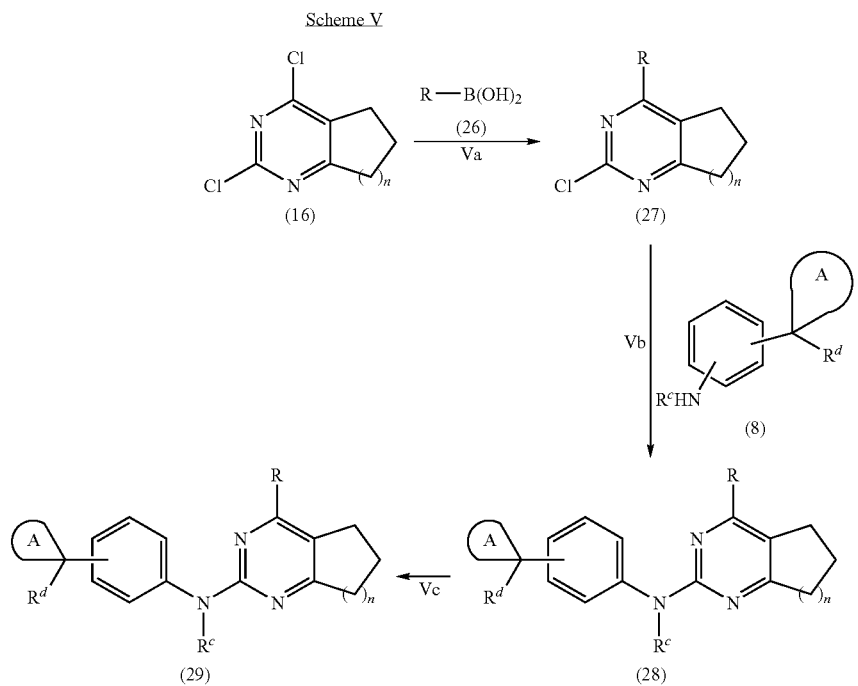

Pathway Va: A compound of general formula (16), wherein n is the same as defined in compound of formula (I), treated with a boron compound of the general formula (26), wherein R is the same as defined in compound of formula (I); in the presence of a palladium catalyst, a base such as sodium carbonate, potassium carbonate, cesium carbonate and the like, in an inert atmosphere followed by work up and chromatography purification can afford a compound of general formula (27).

Pathway Vb: Condensing a compound of general formula (27) wherein R and n are the same as defined in compound of formula (I), with a compound of general formula (8), wherein $R^c$ and A are the same as in defined in compound of formula (I), $R^d$ represents —COOR$^e$, wherein $R^e$ is the same as defined in compound of formula (I), in a polar solvent such as ethanol, 2-propanol, 1-butanol and the like, at a temperature ranging from about 20 to 120° C. for about 6-20 hours followed by work up can afford a compound of general formula (28).

Pathway Vc: Base catalyzed hydrolysis of a compound of general formula (28), wherein R, $R^c$, A and n are the same as defined in compound of formula (I), $R^d$ represents —COOR$^e$, $R^e$ is the same as defined in compound of formula (I), using a procedure as described in Pathway Id, can afford a compound of general formula (29), wherein $R^d$ represents —COOH.

Scheme VI

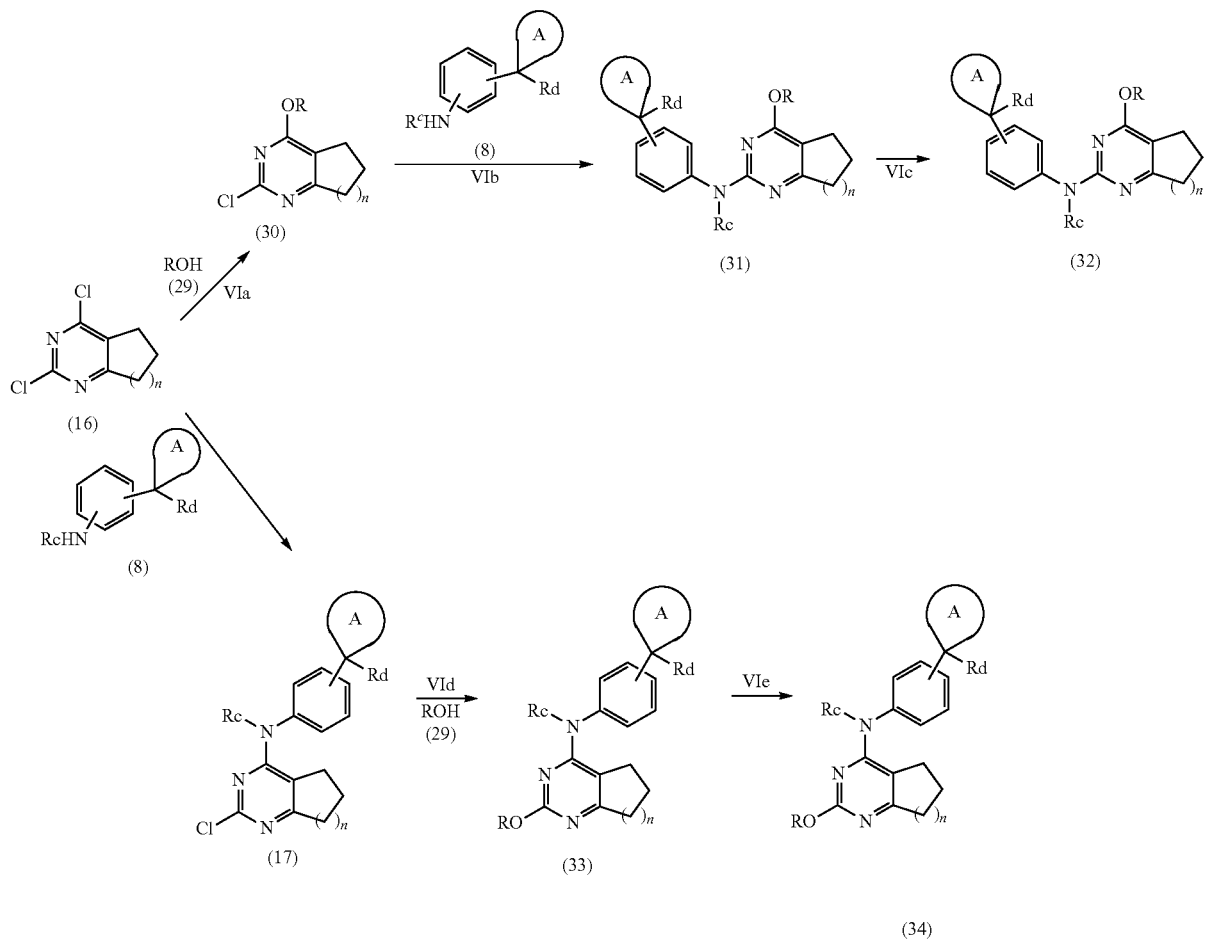

Pathway VIa: Condensation of a compound of general formula (16) with an alcohol of general formula (29), wherein R is the same as defined in compound of formula (I), in the presence of a base such as potassium carbonate, cesium carbonate and the like, in the presence of a polar aprotic solvent such as dimethylformamide and the like, at a temperature in the range of about 20 to 100° C. followed by work up and chromatography purification, can afford a compound of general formula (30).

Pathway VIb: Reacting a compound of general formula (30), wherein R and n are the same as defined in compound of formula (I), with a compound of general formula (8), wherein $R^c$ and A are the same as defined in compound of formula (I), $R^d$ represents —$COOR^e$, $R^e$ is the same as defined in compound of formula (I), in a polar solvent such as 2-propanol, 1-butanol and the like, at a temperature in the range of about 40 to 120° C. followed by work up can afford a compound of general formula (31).

Pathway VIc: Base catalyzed hydrolysis of a compound of general formula (31), wherein R, $R^c$, A and n are the same as defined in compound of formula (I), $R^d$ represents —$COOR^e$, $R^e$ is the same as defined in compound of formula (I), using a procedure as described in Pathway Id, can afford a compound of general formula (32), wherein $R^d$ represents —COOH.

Pathway VId: Reacting a compound of formula with compound of formula (8), to obtain a compound of formula (17). Condensation of a compound of general formula (17) wherein $R^c$, A and n are the same as defined in compound of formula (I), $R^d$ represents —$COOR^e$, $R^e$ is the same as defined in compound of formula (I), with an alcohol of general formula (29), wherein R is the same as defined in compound of formula (I), using a procedure as described in Pathway VIa can afford a compound of general formula (33).

Pathway VIe: Base catalyzed hydrolysis of a compound of general formula (33) using a procedure as described in Pathway Id, can afford a compound of general formula (34), wherein $R^d$ represents —COOH.

The novel compounds of the present invention were prepared according to the procedure of the following schemes and examples, using appropriate materials and are further exemplified by the following specific examples. Exemplary compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention.

Those skilled in the art will readily understand that known variations of the conditions and processes of the following preparative procedures can be used to prepare these compounds.

Example 1

Synthesis of 1-[4-(2-cyclopentyl-6,7-dihydro-5H-cyclopentapyrimidin-4-ylamino)-phenyl]-cyclopentanecarboxylic acid

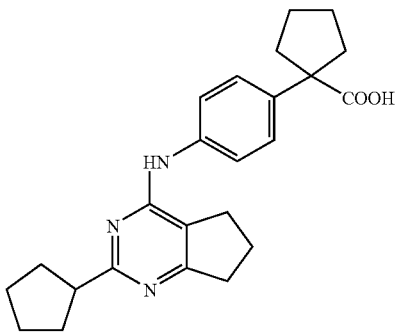

Step (i): Synthesis of 2-cyclopentyl-6,7-dihydro-5H-cyclopentapyrimidin-4-ol

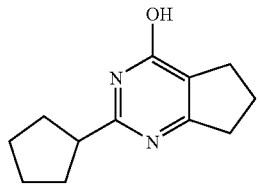

A solution of trimethylaluminum in toluene (2M, 25 mL, 50 mmol) was added slowly under nitrogen to a suspension of ammonium chloride (2.9 g, 54 mmol) in anhydrous toluene at 0° C.-5° C. The mixture was then stirred at a temperature in the range of 15° C. to 40° C. for 20 min before addition of a solution of cyclopentanecarbonitrile (3.13 mL, 30 mmol) in toluene. The resulting mixture was then heated at 80° C. under stirring for 10 hours. Thereafter, the mixture was cooled to a temperature in the range of 15° C. to 40° C. MeOH was slowly added to quench the reaction and stirred at a temperature in the range of 15° C. to 40° C. for 1 hour. Thereafter, the precipitate was filtered and washed with MeOH (3×30 mL). The filtrate and the washings were combined and concentrated under reduced pressure. After drying under vacuum, the crude solid (3.5 g) was dissolved in anhydrous EtOH (20 mL). Methyl-2-oxo-cyclopentanecarboxylate (3.1 mL, 25 mmol) and $K_2CO_3$ (4.14 g, 30 mmol) were added sequentially to this solution and the mixture was heated to reflux for a period over 6-15 hours. Thereafter, volatiles were evaporated under reduced pressure and the mixture was diluted with ice-water under stirring. The resultant precipitate was filtered, washed thoroughly with water followed by ether and dried under vacuum (4.6 g, 95.4% yield).

$^1$H NMR (CDCl$_3$, 300 MHz): δ 11.58 (bs, 1H), 3.08-2.96 (m, 1H), 2.90-2.76 (m, 4H), 2.14-2.02 (m, 4H), 1.92-1.78 (m, 4H), 1.64-1.74 (m, 2H).

LC-MSD (ES+): (m/z) 205 [(M+H)$^+$, 100].

Step (ii): Synthesis of 4-chloro-2-cyclopentyl-6,7-dihydro-5H-cyclopentapyrimidine

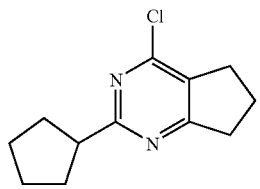

A mixture of 2-cyclopentyl-6,7-dihydro-5H-cyclopentapyrimidin-4-ol (4.5 g, 22 mmol) and phosphorus oxychloride (13 mL, 130 mmol) was heated to reflux for 4 hours. Thereafter, volatiles were evaporated under reduced pressure and the mixture was poured over ice-water. After stirring for 1 hour, the product was extracted with dichloromethane (3×50 mL). The combined organic extracts were washed with water, treated with activated charcoal, dried over anhydrous Na$_2$SO$_4$, filtered, and the filtrate was concentrated under reduced pressure to afford the title compound as a light yellow solid (4.2 g, 86% yield)

$^1$H NMR (CDCl$_3$, 300 MHz): δ 3.22-3.34 (m, 1H), 3.8-2.92 (m, 4H), 2.2-2.03 (m, 4H), 1.88-1.78 (m, 4H), 1.72-1.60 (m, 2H).

LC-MSD (ES+): (m/z) 223 [(M+H)$^+$, 100].

Step (iii): Synthesis of 1-(4-amino-phenyl)cyclopentanecarboxylic acid methyl ester

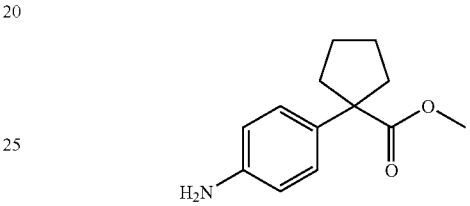

Step (iii-a): Synthesis of (4-nitro-phenyl)-acetic acid methyl ester

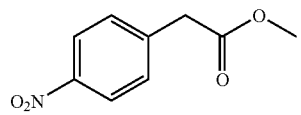

Concentrated sulfuric acid (1 mL) was added to a solution of 4-nitrophenylacetic acid (10.0 g, 55.2 mmol) in anhydrous MeOH and heated under reflux for 3 hours. After evaporation of solvent under reduced pressure the mixture was dissolved in ethyl acetate and washed sequentially with 5% sodium bicarbonate, water, and brine. The organic phase was dried over Na$_2$SO$_4$, filtered, and the filtrate was concentrated under reduced pressure. The residue was solidified on standing at a temperature in the range of 15° C. to 40° C. to afford the title compound as a white solid.

$^1$HNMR (CDCl$_3$, 300 MHz): δ 8.40 (d, J=9 Hz, 2H), 7.48 (d, J=9 Hz, 2H), 3.52 (s, 2H), 3.42 (s, 3H).

LC-MSD (ES+): (m/z) 196 [(M+H)$^+$, 100].

Step (iii-b): Synthesis of 1-(4-amino-phenyl)cyclopentanecarboxylic acid methyl ester

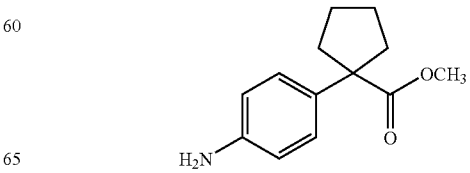

Sodium hydride (2.8 g, 60% dispersion in mineral oil) was added slowly to a solution of (4-nitro-phenyl)-acetic acid methyl ester (6.0 g, 30.7 mmol) in anhydrous DMF (30 mL) under nitrogen at a temperature in the range of 0° C. to 10° C. After stirring at a temperature in the range of 0° C. to 10° C. for 20 min, diiodobutane (7.86 mL, 61 mmol) was added drop-wise under stirring. After complete addition, the reaction mixture was warmed to a temperature in the range of 15° C. to 40° C. and stirring continued for an additional 3 hours. The reaction was quenched by adding water slowly. The mixture was extracted by ethyl acetate (3×40 mL). The combined organic extracts were washed with water, brine, dried over $Na_2SO_4$, filtered, and concentrated under reduced pressure. The resultant gummy material was purified by column chromatography over silica gel to afford a pale yellow thick liquid which solidified on standing at a temperature in the range of 15° C. to 40° C. (4.1 g, 54% yield). The solid (3.4 g, 13.6 mmol) was dissolved in anhydrous EtOH and tin chloride dihydrate (13.86 g, 61 mmol) was added slowly under nitrogen. Thereafter, the mixture was heated at 90° C. for 3 hours. After evaporation of volatiles under reduced pressure, the resultant mixture was diluted with ice-water and aqueous sodium hydroxide was added to adjust pH ~11. The mixture was extracted with ethyl acetate (3×50 mL). The combined organic extracts were washed with water, brine, dried over $Na_2SO_4$, filtered, and the filtrate was concentrated under reduced pressure to afford the title compound as a granular light yellow solid (2.67 g, 88% yield).

$^1$HNMR ($CDCl_3$, 300 MHz): δ 7.16 (dd, J=8.4, 1.8 Hz, 2H), 6.63 (dd, J=8.4, 1.8 Hz, 2H), 3.59 (s, 3H), 2.60-2.55 (m, 2H), 1.87-1.67 (m, 6H).

LC-MSD (ES+): (m/z) 220 [(M+H)$^+$, 100].

Step (iv): Synthesis of 1-[4-(2-cyclopentyl-6,7-dihydro-5H-cyclopentapyrimidin-4-ylamino)-phenyl]-cyclopentanecarboxylic acid methyl ester

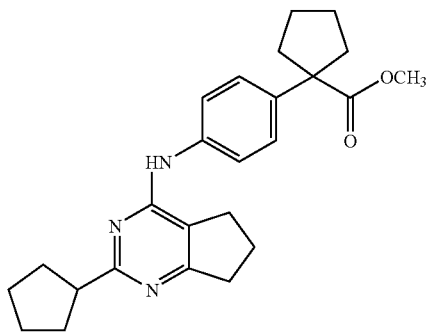

A mixture of 4-chloro-2-cyclopentyl-6,7-dihydro-5H-cyclopentapyrimidine (4.2 g, 18.91 mmol) and 1-(4-amino-phenyl)-cyclopentanecarboxylic acid methyl ester (4.2 g, 19.1 mmol) in anhydrous isopropanol (50 mL) was heated at reflux in a nitrogen atmosphere for 8 to 18 hours. Thereafter, volatiles were evaporated under reduced pressure. The mixture was triturated with ether and filtered. The solid was dissolved in ethyl acetate and washed with 5% sodium bicarbonate and brine. The organic phase was dried over $Na_2SO_4$, filtered, and the filtrate was concentrated under reduced pressure to afford the title compound as a light yellow powder (7.1 g, 93.4% yield).

$^1$H NMR ($CDCl_3$, 300 MHz): δ 7.67 (dd, J=6.6, 1.8 Hz, 2H), 7.34 (dd, J=6.6, 1.8 Hz, 2H), 6.17 (bs, 1H), 3.61 (s, 3H), 3.28-3.18 (m, 1H), 2.96 (t, J=7.5 Hz, 2H), 2.75 (t, J=6.9 Hz, 2H), 2.68-2.60 (m, 2H), 2.18-2.04 (m, 4H), 1.88-1.80 (m, 6H), 1.78-1.66 (m, 6H).

LC-MSD (ES+): (m/z) 406 [(M+H)$^+$, 100].

HPLC: Inertsil ODS-3V C18, 80:20 [$KH_2PO_4$ (0.01 M, pH 3.2): $CH_3CN$], gradient, PDA 280 nm, $R_t$ 14.19 min, purity 99.75%.

Step (v): Synthesis of 1-[4-(2-cyclopentyl-6,7-dihydro-5H-cyclopentapyrimidin-4-ylamino)-phenyl]-cyclopentanecarboxylic acid

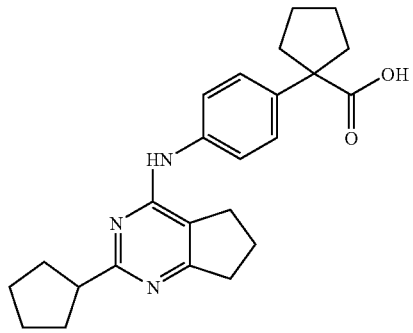

A solution of sodium hydroxide (4.14 g, 100 mmol) in water (100 mL) was added to a solution of 1-[4-(2-cyclopentyl-6,7-dihydro-5H-cyclopentapyrimidin-4-ylamino)-phenyl]-cyclopentanecarboxylic acid methyl ester (7.0 g, 17.2 mmol) in MeOH (100 mL) and the mixture was heated at 90° C. for 8 hours. After evaporation of MeOH under reduced pressure, the mixture was cooled to a temperature in the range of 15° C. to 40° C., and acidified with hydrochloric acid to adjust pH to 3-4. The precipitate formed after standing at a temperature in the range of 15° C. to 40° C. was filtered and washed several times with water, and dried under vacuum. The solid was recrystallized from MeOH to afford the title compound as a white powder (6.3 g, 94% yield).

MP: 321° C.-325° C.

$^1$HNMR ($CDCl_3$+$CD_3OD$, 300 MHz): δ 7.55 (d, J=8.1 Hz, 2H), 7.33 (d, J=8.1 Hz, 2H), 3.43 (m, 1H), 3.1 (t, J=7.8 Hz, 2H), 2.83 (m, 2H), 2.58-2.54 (m, 2H), 2.17-2.10 (m, 2H), 2.06-2.01 (m, 2H), 1.84-1.58 (m, 12H).

LC-MSD (ES+): (m/z) 392 [(M+H)$^+$, 100].

HPLC: Inertsil ODS-3V C18, 80:20 [$KH_2PO_4$ (0.01 M, pH 3.2): $CH_3CN$], gradient, PDA 280 nm, $R_t$ 11.97 min, purity 99.86%.

Example 2

Synthesis of 1-[4-(2-cyclopentylmethyl-6,7-dihydro-5H-cyclopentapyrimidin-4-ylamino)-phenyl]-cyclopentanecarboxylic acid

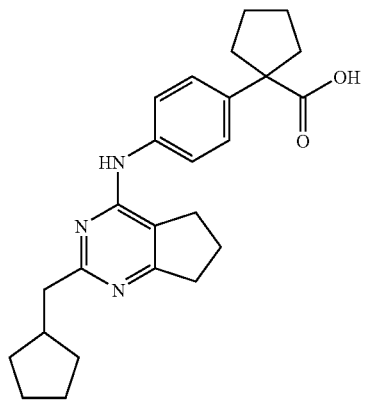

Step (i): Synthesis of 4-chloro-2-cyclopentylmethyl-6,7-dihydro-5H-cyclopentapyrimidine

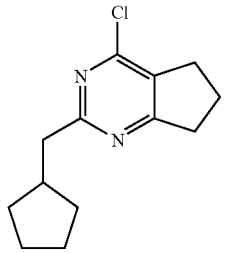

Concentrated sulfuric acid (1 mL) was added to a solution of cyclopentylacetic acid (5.8 mL, 46 mmol) in anhydrous EtOH (15 mL) and heated to reflux for 3 hours. Thereafter, volatiles were removed under reduced pressure and the residue was diluted with water and ethyl acetate. The organic layer was separated, washed with 5% sodium bicarbonate, brine, dried over $Na_2SO_4$, and filtered. After evaporation of solvent under reduced pressure, a syrupy cyclopentylacetic acid ethyl ester was obtained and used in the next step without further purification.

A solution of trimethylaluminum in toluene (2M, 50 mL, 100 mmol) was added slowly under nitrogen to a suspension of ammonium chloride (6.42 g, 120 mmol) in anhydrous toluene (50 mL) at 0° C.-5° C. The mixture was then warmed to a temperature in the range of 15° C. to 40° C. and stirred for 20 min before addition of a solution of cyclopentyl-acetic acid ethyl ester (7.0 g, 45 mmol) in toluene. The resulting mixture was then heated at 80° C.-100° C. under stirring for 10 hours. Thereafter, the mixture was cooled to a temperature in the range of 15° C. to 40° C. MeOH was added slowly to quench the reaction and stirred at a temperature in the range of 15° C. to 40° C. for 1 hour. Thereafter, the precipitate was filtered and washed with MeOH (3×30 mL). The filtrate and the washings were combined and solvent was evaporated under reduced pressure. The resultant semi-solid was dried under vacuum. The material (4.2 g) was dissolved in anhydrous EtOH (30 mL) and methyl-2-oxo-cyclopentanecarboxylate (3.30 mL, 26 mmol) and potassium carbonate (4.14 g, 30 mmol) were added sequentially under stirring at a temperature in the range of 15° C. to 40° C. The resultant mixture was then heated to reflux for a period over 6-15 hours. Thereafter, volatiles were evaporated under reduced pressure, cooled to a temperature in the range of 15° C. to 40° C. and diluted with water. The resultant precipitate was filtered, washed thoroughly with water followed by ether and dried in vacuum to afford 2-cyclopentylmethyl-6,7-dihydro-5H-cyclopentapyrimidin-4-ol (3.7 g, 66% yield).

LC-MSD (ES+): (m/z) 219 [(M+H)+, 100].

Phosphorus oxychloride (4.6 mL, 51 mmol) was added to 2-cyclopentylmethyl-6,7-dihydro-5H-cyclopentapyrimidin-4-ol (3.7 g, 17 mmol) and the mixture was heated at reflux for 2 hours. Thereafter, volatiles were evaporated under reduced pressure and the mixture was poured over ice-water. The mixture was extracted with dichloromethane (3×60 mL). The combined organic extracts were washed with water, treated with activated charcoal, dried over anhydrous $Na_2SO_4$, filtered, and the filtrate was concentrated under reduced pressure to afford the title compound as a light yellow solid (3.1 g, 78% yield).

$^1$H NMR (CDCl$_3$, 300 MHz): δ 3.15-2.82 (m, 6H), 2.38-2.28 (m, 3H), 2.2-2.08 (m, 2H), 1.80-1.51 (m, 6H).

LC-MSD (ES+): (m/z) 237 [(M+H)+, 100].

Step (ii): Synthesis of 1-[4-(2-cyclopentylmethyl-6,7-dihydro-5H-cyclopentapyrimidin-4-ylamino)-phenyl]-cyclopentanecarboxylic acid methyl ester

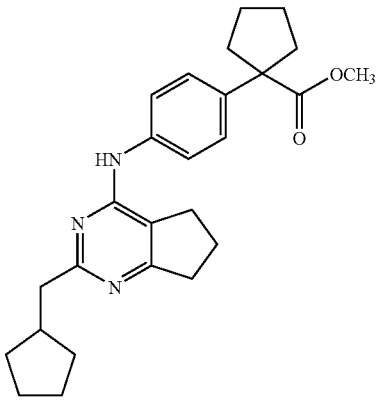

A mixture of 4-chloro-2-cyclopentylmethyl-6,7-dihydro-5H-cyclopentapyrimidine (0.38 g, 1.6 mmol) and 1-(4-amino-phenyl)-cyclopentane carboxylic acid methyl ester (0.35 g, 1.6 mmol) in anhydrous isopropanol (8 mL) was heated at reflux under nitrogen for 8 to 18 hours. Thereafter, volatiles were evaporated under reduced pressure. The residue was triturated with ether and filtered. The solid was dissolved in ethyl acetate, washed with 5% sodium bicarbonate, dried over $Na_2SO_4$, filtered, and the filtrate was concentrated under reduced pressure to afford the title compound as a light yellow powder (0.42 g, 63% yield).

$^1$H NMR (CDCl$_3$, 300 MHz): δ 7.62 (dd, J=6.6, 1.8 Hz, 2H), 7.33 (dd, J=6.6, 1.8 Hz, 2H), 6.80 (bs, 1H), 3.61 (s, 3H), 2.93 (t, J=7.8 Hz, 2H), 2.81-2.62 (m, 6H), 2.47-2.42 (m, 1H), 2.18-2.10 (m, 2H), 1.93-1.86 (m, 2H), 1.75-1.49 (m, 10H), 1.34-1.30 (m, 2H).

LC-MSD (ES+): (m/z) 420 [(M+H)+, 100].

HPLC: Inertsil ODS-3V C18, 30:70 [KH$_2$PO$_4$ (0.01 M, pH 3.2): CH$_3$CN], PDA 264 nm, R$_t$ 4.77 min, purity 96.99%.

Step (iii): Synthesis of 1-[4-(2-cyclopentylmethyl-6,7-dihydro-5H-cyclopentapyrimidin-4-ylamino)-phenyl]-cyclopentanecarboxylic acid

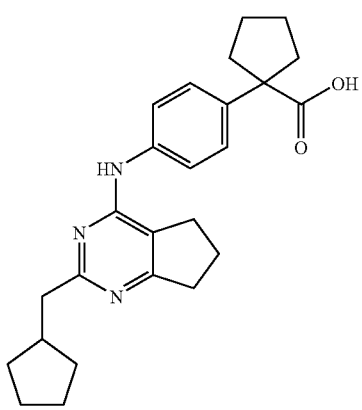

The title compound was obtained as a white solid after hydrolysis of 1-[4-(2-cyclopentylmethyl-6,7-dihydro-5H-cyclopentapyrimidin-4-ylamino)-phenyl]-cyclopentanecarboxylic acid methyl ester following the procedure as described in Example 1, step (v) (77% yield).

$^1$H NMR (CDCl$_3$+CD$_3$OD, 300 MHz): δ 7.54 (d, J=8.7 Hz, 2H), 7.31 (d, J=8.7 Hz, 2H), 2.85 (t, J=7.8 Hz, 2H), 2.69-2.54 (m, 6H), 2.35-2.29 (m, 1H), 2.10-1.99 (m, 2H), 1.87-1.79 (m, 2H), 1.69-1.46 (m, 10H), 1.25-1.13 (m, 2H).

LC-MSD (ES+): (m/z) 406 [(M+H)$^+$, 100].

HPLC: Inertsil ODS-3V C18, 20:80 [KH$_2$PO$_4$ (0.01 M, pH 3.2): CH$_3$CN], gradient, PDA 264 nm, R$_t$ 12.10 min, purity 94.36%.

Example 3

Synthesis of 1-[4-(2-cyclopentyl-6,7-dihydro-5H-cyclopentapyrimidin-4-ylamino)-phenyl]-cyclobutanecarboxylic acid

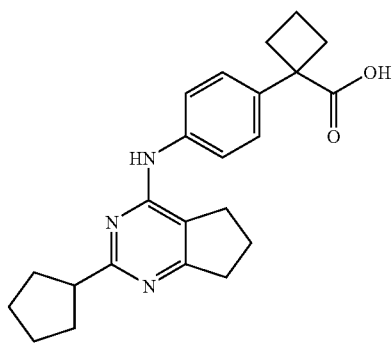

Step (i): Synthesis of 1-(4-amino-phenyl)-cyclobutanecarboxylic acid methyl ester

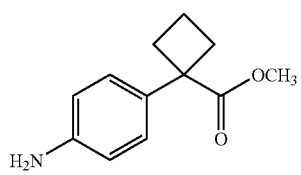

The title compound was prepared following the procedure as described in Example 1, step (iii) except diiodopropane was used instead of diiodobutane in step (iii-b) (90% yield).

$^1$HNMR (CDCl$_3$, 300 MHz): δ 7.12-7.07 (m, 2H), 6.68-6.63 (m, 2H), 3.71 (s, 2H), 3.62 (s, 3H), 2.82-2.72 (m, 2H), 2.49-2.38 (m, 2H), 2.05-1.79 (m, 2H).

LC-MSD (ES+): (m/z) 206 [(M+H)$^+$, 100].

Step (ii): Synthesis of 1-[4-(2-cyclopentyl-6,7-dihydro-5H-cyclopentapyrimidin-4-ylamino)-phenyl]-cyclobutanecarboxylic acid methyl ester

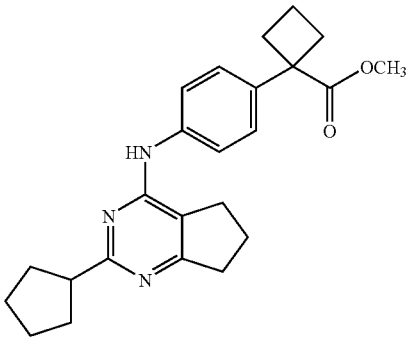

The title compound was prepared following the procedure as described in Example 1, step (iv) (53% yield).

$^1$H NMR (CDCl$_3$, 300 MHz): δ 7.67 (d, J=8.4 Hz, 2H), 7.34 (d, J=8.4 Hz, 2H), 6.18 (bs, 1H), 3.65 (s, 3H), 3.25-3.18 (m, 1H), 2.96 (t, J=7.4 Hz, 2H), 2.87-2.78 (m, 2H), 2.75 (t, J=7.4 Hz, 2H), 2.55-2.46 (m, 2H), 2.16-1.84 (m, 10H), 1.70-1.66 (m, 2H).

LC-MSD (ES+): (m/z) 392 [(M+H)$^+$, 100].

HPLC: Inertsil ODS-3V C18, 20:80 [KH$_2$PO$_4$ (0.01 M, pH 3.2): CH$_3$CN], gradient, PDA 264 nm, R$_t$ 12.74 min, purity 99.75%.

Step (iii): Synthesis of 1-[4-(2-cyclopentyl-6,7-dihydro-5H-cyclopentapyrimidin-4-ylamino)-phenyl]-cyclobutanecarboxylic acid

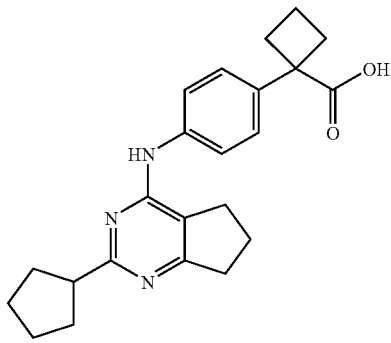

The title compound was prepared following the procedure as described in Example 1, step (v) (90% yield).

$^1$H NMR (CDCl$_3$+CD$_3$OD, 300 MHz): δ 7.59 (d, J=8.7 Hz, 2H), 7.24 (d, J=8.7 Hz, 2H), 3.29-3.24 (m, 1H), 3.0 (t, J=7.8 Hz, 2H), 2.80-2.73 (m, 4H), 2.45-2.42 (m, 2H), 2.11-1.84 (m, 6H), 1.83-1.60 (m, 6H).

LC-MSD (ES+): (m/z) 378 [(M+H)$^+$, 100].

HPLC: Inertsil ODS-3V C18, 20:80 [KH$_2$PO$_4$ (0.01 M, pH 3.2): CH$_3$CN], gradient, PDA 264 nm, R$_t$ 10.82 min, purity 99.17%.

6 mm, R$_t$ 10.82 min).

Example 4

Synthesis of 1-[4-(2-morpholin-4-yl-6,7-dihydro-5H-cyclopentapyrimidin-4-ylamino)-phenyl]-cyclobutanecarboxylic acid

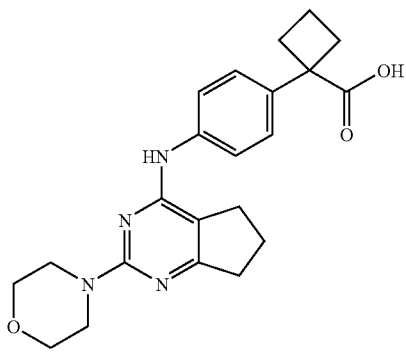

Step (i): Synthesis of 6,7-dihydro-5H-cyclopentapyrimidine-2,4-diol

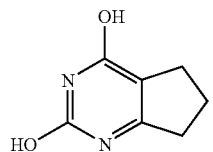

Chlorotrimethylsilane (20.9 g, 193.6 mmol) was added drop wise under nitrogen to a solution of 2-oxo-cyclopentanecarboxylic acid methyl ester (25 g, 176 mmol) and urea (19.01 g, 316 mmol) in anhydrous DMF (200 mL) at 0° C. After addition, the mixture was warmed to a temperature in the range of 15° C. to 40° C. and stirred for 48 hours. Water was added to the mixture and the resultant precipitate was filtered, washed with water followed by petroleum ether and dried in vacuo. The solid was suspended to a solution of sodium hydroxide (19.9 g, 499 mmol) in water (280 mL) and stirred at 70° C. for 1 hour. After cooling to a temperature in the range of 15° C. to 40° C., concentrated hydrochloric acid was added drop wise to adjust the pH to ~2. The resultant precipitate was filtered, washed with water and dried in vacuo to afford the title compound as a white solid (21.2 g, 79% yield).

$^1$HNMR (DMSO-d$_6$, 400 MHz): δ 11.15 (s, 1H), 10.75 (s, 1H), 2.71-2.32 (m, 4H), 2.1-1.80 (m, 2H).
LC-MSD (ES+): (m/z) 153 [(M+H)$^+$, 100].
IR (KBr): 3531, 3140, 3028, 2812, 2676, 1678 cm$^{-1}$.

Step (ii): Synthesis of 2,4-dichloro-6,7-dihydro-5H-cyclopentapyrimidine

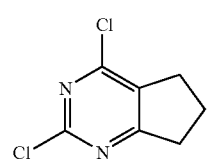

Phosphorus oxychloride (70.59 g, 460.5 mmol) was added to 6,7-dihydro-5H-cyclopentapyrimidine-2,4-diol (20 g, 131.5 mmol) and the mixture was stirred at a temperature in the range of 20° C. to 60° C. for 3 hours. Thereafter, volatiles were evaporated under reduced pressure and the residue was poured over ice-water. After stirring for 30 min, the mixture was extracted with dichloromethane (3×100 mL). The combined organic extracts were collected, washed with brine, dried over Na$_2$SO$_4$, filtered, and the filtrate was concentrated under reduced pressure. The residue was purified by column chromatography (silica gel) to afford the title compound as a white solid (22.4 g, 90% yield).

MP: 77° C.-79° C.
$^1$HNMR (CDCl$_3$, 400 MHz): δ 3.18-2.85 (m, 4H), 2.31-2.16 (m, 2H).
LC-MSD (ES+): (m/z) 189 [(M+H)$^+$, 100].

Step (iii): Synthesis of 1-[4-(2-chloro-6,7-dihydro-5H-cyclopentapyrimidin-4-ylamino)-phenyl]-cyclobutanecarboxylic acid methyl ester

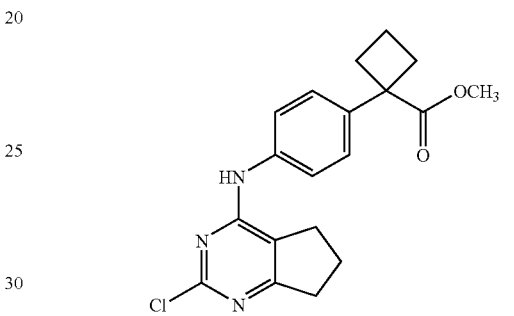

Diisopropylethylamine (45.9 mL, 264.55 mmol) was added slowly to a solution of 2,4-dichloro-6,7-dihydro-5H-cyclopentapyrimidine (10 g, 52.91 mmol) and 1-(4-aminophenyl)-cyclobutanecarboxylic acid methyl ester (13.015 g, 63.49 mmol) in anhydrous ethanol (100 mL) under stirring at 10° C. Thereafter, the mixture was heated at reflux for 48 hours and then concentrated under reduced pressure. The residue was purified by chromatography (silica gel) to afford the title compound as a light yellow solid (11.7 g, 62% yield).

$^1$H NMR (CDCl$_3$, 400 MHz,): δ 7.51 (dd, J=6.3, 1.9 Hz, 2H), 7.30 (dd, J=6.3, 1.9 Hz, 2H), 3.65 (s, 3H), 2.93 (t, 2H, J=7.8 Hz, 2H), 2.86-2.79 (m, 2H), 2.70-2.65 (m, 2H), 2.52-2.45 (m, 2H), 2.20-2.12 (m, 2H), 2.08-1.98 (m, 1H), 1.90-1.84 (m, 1H).
LC-MSD (ES+): (m/z) 358 [(M+H)$^+$, 100].
IR (KBr): 3360, 2980, 2949, 1711, 1618, 1571, 1514, 1441 cm$^{-1}$.

Step (iv): Synthesis of 1-[4-(2-morpholin-4-yl-6,7-dihydro-5H-cyclopentapyrimidin-4-ylamino)-phenyl]-cyclobutanecarboxylic acid methyl ester

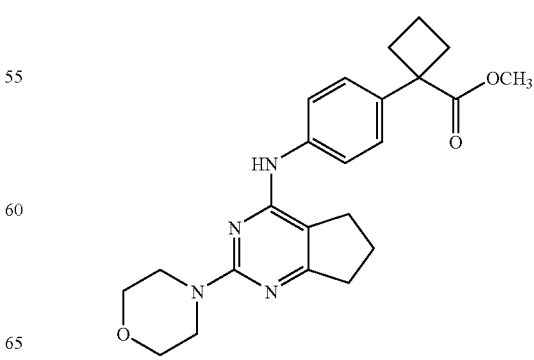

A mixture of 1-[4-(2-chloro-6,7-dihydro-5H-cyclopentapyrimidin-4-ylamino)-phenyl]-cyclobutanecarboxylic acid methyl ester (2 g, 5.594 mmol), morpholine (0.64 mL, 7.27 mmol) and diisopropylethylamine (1.46 mL, 8.392 mmol) in isopropanol (25 mL) was heated at reflux for 50 hours. After cooling to a temperature in the range of 15° C. to 40° C., the precipitated solid was filtered, washed with hexane and dried. The solid was dissolved in ethyl acetate, washed with water, brine, dried over $Na_2SO_4$, filtered, and the filtrate was concentrated under reduced pressure to afford the title compound as a light yellow solid (1.9 g, 83% yield).

$^1$H NMR (CDCl$_3$, 400 MHz): δ 7.55 (dd, J=6.6, 2.2 Hz, 2H), 7.26 (dd, J=6.6, 2.2 Hz, 2H), 3.80 to 3.76 (m, 8H), 3.65 (s, 3H), 2.85-2.78 (m, 4H), 2.67 (t, J=7.3 Hz, 2H), 2.52-2.45 (m, 2H), 2.12-2.06 (m, 2H), 2.06-1.96 (m, 1H), 1.92-1.84 (m, 1H).

LC-MSD (ES+): (m/z) 409 [(M+H)$^+$, 100].

IR (KBr): 3381, 2854, 1711, 1624, 1560 cm$^{-1}$.

HPLC: Symmetry shield RP 18, 20:80 [KH$_2$PO$_4$ (0.01 M, pH 6.5): CH$_3$CN], gradient, PDA 258 nm, R$_t$ 15.82 min, purity 98.20%.

Step (v): Synthesis of 1-[4-(2-morpholin-4-yl-6,7-dihydro-5H-cyclopentapyrimidin-4-ylamino)-phenyl]-cyclobutanecarboxylic acid

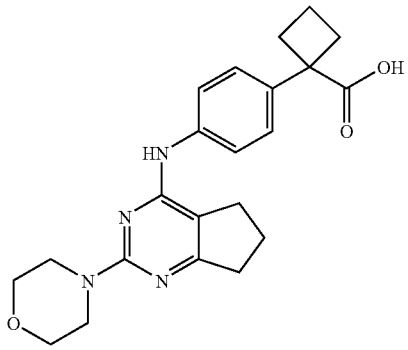

A solution of sodium hydroxide (0.588 g, 14.7 mmol) in water (15 mL) was added to a solution of 1-[4-(2-morpholin-4-yl-6,7-dihydro-5H-cyclopentapyrimidin-4-ylamino)-phenyl]-cyclobutanecarboxylic acid methyl ester (1.0 g, 2.45 mmol) in MeOH (15 mL) and stirred at a temperature in the range of 15° C. to 40° C. for 3 hours. Thereafter, MeOH was evaporated under reduced pressure and pH of the solution was adjusted to ~4 by adding concentrated hydrochloric acid. The precipitated solid was filtered, washed with water and dried in vacuo to afford the title compound as a white solid (0.9 g, 93.2% yield).

MP: 279° C.-281° C.

$^1$H NMR (DMSO-d$_6$, 400 MHz): δ 7.70 (dd, J=8.2, 1.9 Hz, 2H), 7.19 (dd, J=8.2, 1.9 Hz, 2H), 3.63-3.59 (m, 8H), 2.73-2.60 (m, 6H), 2.40-2.32 (m, 2H), 2.00-1.92 (m, 2H), 1.92-1.85 (m, 1H), 1.82-1.70 (m, 1H).

LC-MSD (ES+): (m/z) 395 [(M+H)$^+$, 100].

IR (KBr): 3329, 2982, 2853, 1589, 1570, 1514, 1435 cm$^{-1}$.

HPLC: Symmetry shield RP 18, 20:80 [KH$_2$PO$_4$ (0.01 M, pH 6.5): CH$_3$CN], gradient, PDA 210 nm, R$_t$ 10.81 min, purity 97.20%.

Example 5

Synthesis of 1-{4-[2-(4-hydroxy-piperidin-1-yl)-6,7-dihydro-5H-cyclopentapyrimidin-4-ylamino]-phenyl}-cyclobutanecarboxylic acid

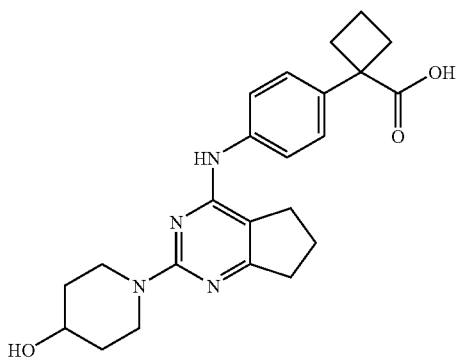

The title compound was prepared following the procedure as described in Example 4 except 4-hydroxypiperidine was used instead of morpholine in step (iv) (93% yield).

MP: 165° C.-167° C.

$^1$H NMR (DMSO-d$_6$, 400 MHz): δ 12.20 (bs, 1H), 8.32 (s, 1H), 7.74 (d, J=8.2 Hz, 2H), 7.18 (d, J=8.2 Hz, 2H), 4.60 (bs, 1H), 4.32-4.27 (m, 4H), 3.72-3.61 (m, 1H), 3.05-3.16 (m, 2H), 2.68-2.60 (m, 4H), 2.42-2.32 (m, 2H), 2.0-1.64 (m, 6H), 1.40-1.21 (m, 2H).

LC-MSD (ES+): (m/z) 409 [(M+H)$^+$, 100].

HPLC: Symmetry shield RP 18, 30:70 [KH$_2$PO$_4$ (0.01 M, pH 6.5): CH$_3$CN], PDA 210 nm, R$_t$ 4.87 min, purity 96.07%.

Example 6

Synthesis of 1-[4-(2-pyrrolidin-1-yl-6,7-dihydro-5H-cyclopentapyrimidin-4-ylamino)-phenyl]-cyclobutanecarboxylic acid

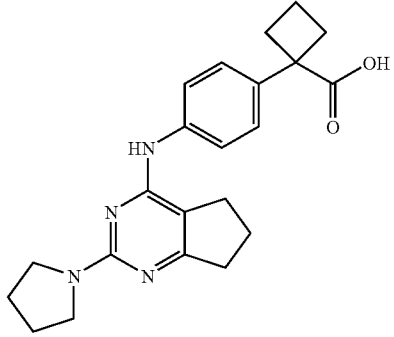

The title compound was prepared following the procedure as described in Example 4 except pyrrolidine was used instead of morpholine in step (iv) (80% yield).

MP: 245° C.-247° C.

$^1$H NMR (DMSO-d$_6$, 400 MHz): δ 12.02 (s, 1H), 8.28 (s, 1H), 7.82 (dd, J=1.8, 8.2 Hz, 2H), 7.20 (dd, J=1.8, 8.2 Hz, 2H), 2.74-2.62 (m, 10H), 2.31-2.41 (m, 2H), 2.00-1.64 (m, 8H).

LC-MSD (ES+): (m/z) 379 [(M+H)$^+$, 100].

HPLC: Symmetry shield RP 18, 30:70 [KH$_2$PO$_4$ (0.01 M, pH 6.5): CH$_3$CN], PDA 210 nm, R$_t$ 7.13 min, purity 99.06%.

Example 7

Synthesis of 1-{4-[2-(1-methyl-1H-pyrazol-4-yl)-6,7-dihydro-5H-cyclopentapyrimidin-4-ylamino]-phenyl}-cyclobutanecarboxylic acid

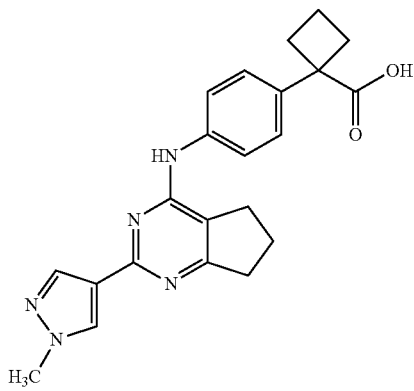

Step (i): Synthesis of 1-{4-[2-(1-methyl-1H-pyrazol-4-yl)-6,7-dihydro-5H-cyclopentapyrimidin-4-ylamino]-phenyl}-cyclobutanecarboxylic acid methyl ester

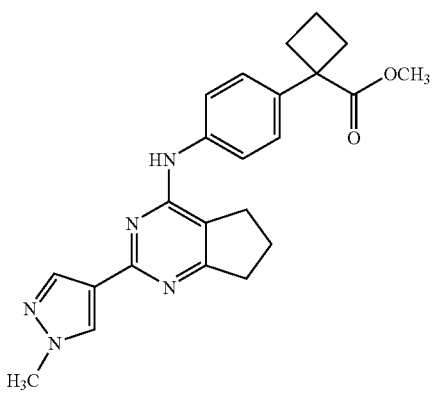

A glass tube was charged with 1-[4-(2-chloro-6,7-dihydro-5H-cyclopentapyrimidin-4-ylamino)-phenyl]-cyclobutanecarboxylic acid methyl ester (0.5 g, 1.4 mmol), 1-methyl-1H-pyrazole-5-boronic acid pinacol ester (0.42 g, 2 mmol), dichloro[1,1'-bis(diphenylphosphino)ferrocene]palladium (II) (0.081 g, 0.1 mmol) and alternatively purged and backfilled with nitrogen. After addition of anhydrous toluene (10 mL), EtOH (5 mL), and sodium carbonate (2M, 2 mL) the glass tube was sealed and heated at 100° C. under stirring until the reaction was complete as evidenced by the disappearance of starting chloro compound (TLC). The resulting mixture was cooled to a temperature in the range of 15° C. to 40° C., diluted with ethyl acetate (20 mL), filtered through Celite, washed with ethyl acetate, and the combined filtrate was concentrated under reduced pressure. The residue was purified by flash chromatography over silica gel to afford the title compound as a light yellow solid (0.27 g, 48%).

$^1$H NMR (CDCl$_3$, 300 MHz): δ8.14 (s, 1H), 8.02 (s, 1H), 7.67 (dd, J=6.6, 1.8 Hz, 2H), 7.32 (dd, J=6.6, 1.8 Hz, 2H), 6.21 (bs, 1H), 3.95 (s, 3H), 3.66 (s, 3H), 3.02-2.74 (m, 6H), 2.58-2.46 (m, 2H), 2.21-1.84 (m, 4H).

LC-MSD (ES+): (m/z) 404 [(M+H)$^+$, 100].

HPLC: Inertsil ODS-3V C18, 20:80 [KH$_2$PO$_4$ (0.01 M, pH 3.2): CH$_3$CN], gradient, PDA 280 nm, R$_t$ 12.82 min, purity 99.75%.

Step (ii): Synthesis of 1-{4-[2-(1-methyl-1H-pyrazol-4-yl)-6,7-dihydro-5H-cyclopentapyrimidin-4-ylamino]-phenyl}-cyclobutanecarboxylic acid

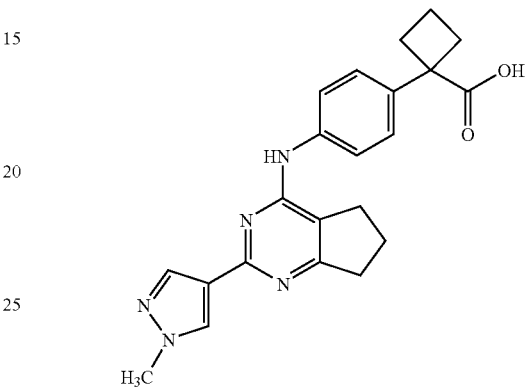

The title compound was obtained as a white powder after hydrolysis of 1-{4-[2-(1-methyl-1H-pyrazol-4-yl)-6,7-dihydro-5H-cyclopentapyrimidin-4-ylamino]-phenyl}-cyclobutanecarboxylic acid methyl ester following the procedure as described in Example 1, step (v) (98% yield).

$^1$H NMR (CDCl$_3$+CD$_3$OD, 300 MHz): δ8.74 (s, 1H), 8.05 (s, 1H), 7.51 (d, J=7.8 Hz, 2H), 7.28 (d, J=7.8 Hz, 2H), 3.88 (s, 3H), 3.24 (t, J=6.9 Hz, 2H), 2.82-2.70 (m, 4H), 2.47-2.37 (m, 2H), 2.19-2.07 (m, 2H), 2.02-1.75 (m, 2H).

LC-MSD (ES+): (m/z) 390 [(M+H)$^+$, 100].

HPLC: Inertsil ODS-3V C18, 20:80 [KH$_2$PO$_4$ (0.01 M, pH 3.2): CH$_3$CN], gradient, PDA 280 nm, R$_t$ 10.55 min, purity 98.48%.

Example 8

Synthesis of 1-{4-[2-(4-fluoro-phenyl)-6,7-dihydro-5H-cyclopentapyrimidin-4-ylamino]-phenyl}-cyclopentanecarboxylic acid

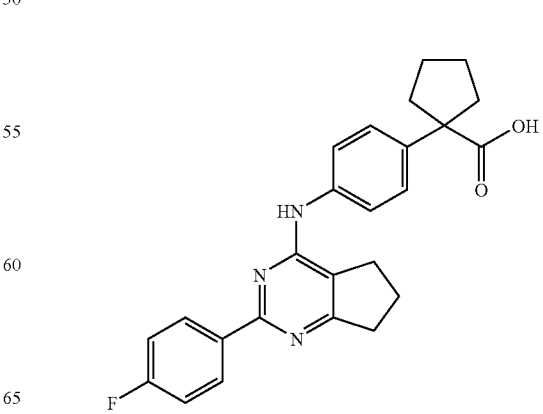

Step (i): Synthesis of 4-chloro-2-(4-fluoro-phenyl)-6,7-dihydro-5H-cyclopentapyrimidine

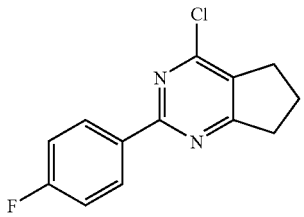

Hexamethyldisilazane (52.13 mL, 250 mmol) was added drop-wise to a solution of n-butyllithium in hexane (2.5 M, 100 mL, 250 mmol) in anhydrous ether (250 mL) at 0° C. under nitrogen. After stirring for 30 min a solution of 4-fluorobenzonitrile (15.10 g, 125 mmol) in anhydrous ether (50 mL) was added slowly and stirred at the same temperature for 1 hour. Thereafter, the mixture was warmed to a temperature in the range of 15° C. to 40° C. and stirred for an additional 3 hours. The mixture was then cooled to 0° C. to 5° C. and the reaction was quenched with drop-wise addition of hydrochloric acid (3N, 200 mL). After stirring at a temperature in the range of 15° C. to 40° C. for 1 hour the aqueous phase was separated from the organic mixture and made basic (pH ~11) by addition of 3N sodium hydroxide. The aqueous solution was extracted with dichloromethane (3×75 mL) and the combined organic extracts was washed with brine, dried over $Na_2SO_4$, filtered and the filtrate was concentrated under reduced pressure to afford crude amidine (13.2 g, 78%). A mixture of amidine (13.2 g, 96 mmol) and methyl-2-oxo-cyclopentanecarboxylate (12.15 mL, 96 mmol) in anhydrous EtOH (100 mL) was heated at reflux for 16 hours and then cooled to a temperature in the range of 15° C. to 40° C. The precipitated solid was filtered, washed with ether and dried in vacuo (yield 19.45 g, 88%). A mixture of this solid material and phosphorus oxychloride (19.0 g) was heated at reflux for 2 hours. After evaporation of volatiles under reduced pressure the dark brown mixture was poured over ice-water and stirred for ~2 hours. After adjusting pH to ~7 the aqueous mixture was extracted with dichloromethane (3×100 mL). The combined organic extracts were washed with brine, dried over $Na_2SO_4$, filtered and the filtrate was concentrated under reduced pressure to afford the title compound as a white solid (yield 17.1 g, 84%).

$^1$H NMR (CDCl$_3$, 300 MHz): δ 8.44-8.39 (m, 2H), 7.25-7.10 (m, 2H), 3.14 (t, J=7.8 Hz, 2H), 3.04 (t, J=7.8 Hz, 2H), 2.25-2.15 (m, 2H).

LC-MSD (ES+): (m/z) 249 [(M+H)$^+$, 100].

Step (ii): Synthesis of 1-{4-[2-(4-fluoro-phenyl)-6,7-dihydro-5H-cyclopentapyrimidin-4-ylamino]-phenyl}-cyclopentanecarboxylic acid methyl ester The title compound was afforded as a white solid following the procedure as described in Example 1, step (iv) except 4-chloro-2-(4-fluoro-phenyl)-6,7-dihydro-5H-cyclopentapyrimidine was used instead of 4-chloro-2-cyclopentyl-6,7-dihydro-5H-cyclopentapyrimidine. (50% yield).

$^1$H NMR (CDCl$_3$, 300 MHz): δ8.41-8.36 (m, 2H), 7.68 (dd, J=6.6, 1.8 Hz, 2H), 7.40 (dd, J=6.6, 1.8 Hz, 2H), 7.16-7.10 (m, 2H), 6.25 (s, 1H), 3.63 (s, 3H), 3.05 (t, J=7.8 Hz, 2H), 2.83 (t, J=7.8 Hz, 2H), 2.70-2.63 (m, 2H), 2.25-2.17 (m, 2H), 1.96-1.92 (m, 2H), 1.79-1.73 (m, 4H).

LC-MSD (ES+): (m/z) 432 [(M+H)$^+$, 100].

HPLC: Inertsil ODS-3V C18, 30:70 [KH$_2$PO$_4$ (0.01 M, pH 3.2): CH$_3$CN], PDA 264 nm, R$_t$ 24.82 min, purity 93.45%.

Step (iii): Synthesis of 1-{4-[2-(4-fluoro-phenyl)-6,7-dihydro-5H-cyclopentapyrimidin-4-ylamino]-phenyl}-cyclopentanecarboxylic acid

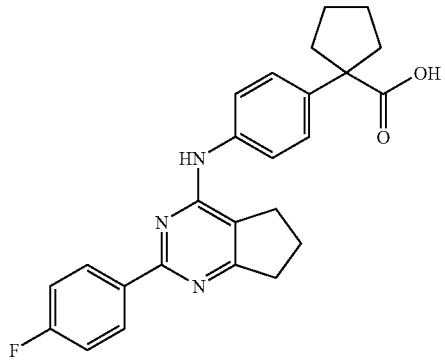

Hydrolysis of 1-{4-[2-(4-fluoro-phenyl)-6,7-dihydro-5H-cyclopentapyrimidin-4-ylamino]-phenyl}-cyclopentanecarboxylic acid methyl ester following the procedure as described in Example 1, step (v) afforded the title compound as a white solid (88% yield).

$^1$H NMR (CDCl$_3$+CD$_3$OD, 300 MHz): δ8.34-8.30 (m, 2H), 7.52 (d, J=6.9 Hz, 2H), 7.39 (d, J=6.9 Hz, 2H), 7.18-7.13 (m, 2H), 3.31-3.21 (m, 2H), 2.92-2.83 (m, 2H), 2.63-2.54 (m, 2H), 2.24-2.18 (m, 2H), 1.86-1.68 (m, 6H).

LC-MSD (ES+): (m/z) 418 [(M+H)$^+$, 100].

HPLC: Inertsil ODS-3V C18, 30:70 [KH$_2$PO$_4$ (0.01 M, pH 3.2): CH$_3$CN], PDA 264 nm, R$_t$ 10.49 min, purity 99.75%.

Example 9

Synthesis of 1-{4-[2-(4-acetyl-phenyl)-6,7-dihydro-5H-cyclopentapyrimidin-4-ylamino]-phenyl}-cyclobutanecarboxylic acid

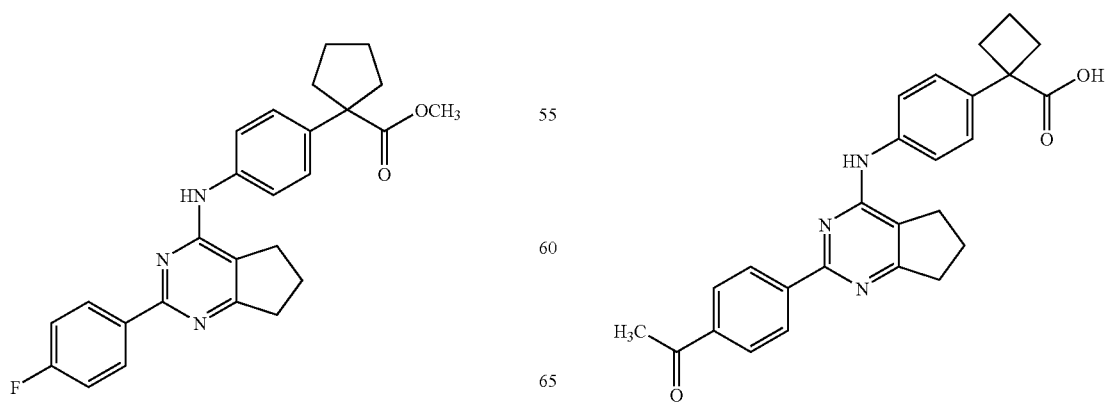

Step (i): Synthesis of 1-{4-[2-(4-acetyl-phenyl)-6,7-dihydro-5H-cyclopentapyrimidin-4-ylamino]-phenyl}-cyclobutanecarboxylic acid methyl ester

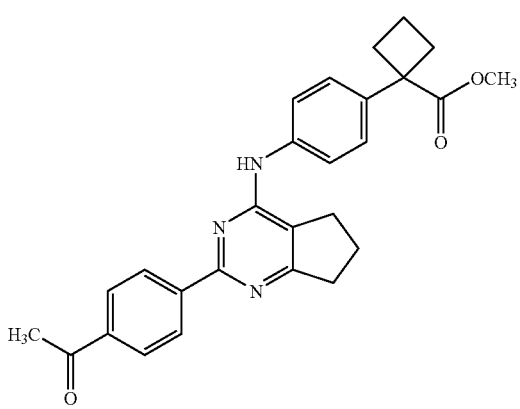

The title compound was afforded as a white solid following the procedure as described in Example 7, step (i) except 4-acetylphenylboronic acid was used instead of 1-methyl-1H-pyrazole-5-boronic acid pinacol ester (23% yield).

$^1$H NMR (CDCl$_3$, 300 MHz): δ8.50 (d, J=8.4 Hz, 2H), 8.06 (d, J=8.4 Hz, 2H), 7.71 (d, J=8.7 Hz, 2H), 7.36 (d, J=8.7 Hz, 2H), 6.31 (s, 1H), 3.67 (s, 3H), 3.08 (t, J=7.8 Hz, 2H), 2.90-2.81 (m, 4H), 2.65 (s, 3H), 2.58-2.49 (m, 2H), 2.27-2.20 (m, 2H), 2.06-1.92 (m, 2H).

LC-MSD (ES+): (m/z) 442 [(M+H)$^+$, 100].

Step (ii): Synthesis of 1-{4-[2-(4-acetyl-phenyl)-6,7-dihydro-5H-cyclopentapyrimidin-4-ylamino]-phenyl}-cyclobutanecarboxylic acid

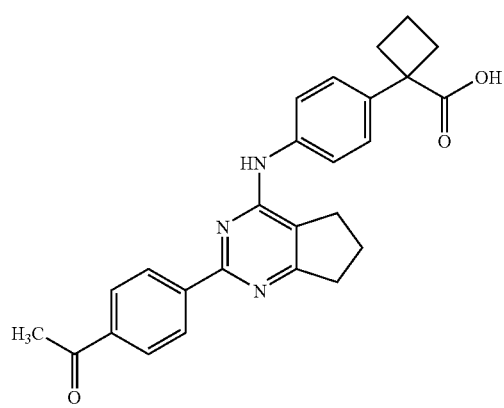

The title compound was prepared following the procedure as described in Example 7, step (ii) (95% yield).

$^1$H NMR (CDCl$_3$+CD$_3$OD, 300 MHz): δ8.40 (d, J=8.4 Hz, 2H), 8.04 (d, J=8.1 Hz, 2H), 7.58 (d, J=8.4 Hz, 2H), 7.33 (d, J=8.1 Hz, 2H), 3.28-3.20 (m, 2H), 2.87-2.72 (m, 4H), 2.58 (s, 3H), 2.47-2.40 (m, 2H), 2.25-2.20 (m, 2H), 2.03-1.82 (m, 2H).

LC-MSD (ES+): (m/z) 428 [(M+H)$^+$, 100].

HPLC: Inertsil ODS-3V C18, 30:70 [KH$_2$PO$_4$ (0.01 M, pH 3.2): CH$_3$CN], PDA 264 nm, R$_t$ 6.89 min, purity 96.44%.

Example 10

Synthesis of 1-[4-(4-tert-butylamino-6,7-dihydro-5H-cyclopentapyrimidin-2-ylamino)-phenyl]-cyclopentanecarboxylic acid

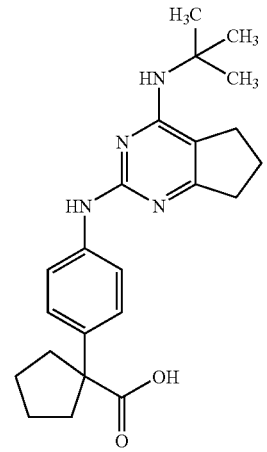

Step (i): Synthesis of tert-butyl-(2-chloro-6,7-dihydro-5H-cyclopentapyrimidin-4-yl)-amine

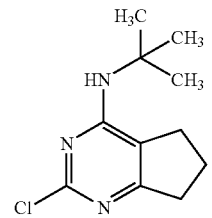

A mixture of 2,4-dichloro-6,7-dihydro-5H-cyclopentapyrimidine (0.47 g, 2.5 mmol), tert-butylamine (1.25 ml, 11.8 mmol) and isopropanol (5 ml) was heated at reflux for 8 to 18 hours. After evaporation of volatiles the mixture was purified by flash chromatography over silica gel to afford the title compound as a white solid (0.36 g, 64% yield).

$^1$HNMR (CDCl$_3$, 300 MHz) δ 4.43 (bs, 1H), 2.87 (t, J=7.8 Hz, 2H), 2.58 (t, J=7.8 Hz, 2H), 2.15-2.07 (m, 2H), 1.47 (s, 9H).

LC-MSD (ES+): (m/z) 226 [(M+H)$^+$, 100].

Step (ii): Synthesis of 1-[4-(4-tert-butylamino-6,7-dihydro-5H-cyclopentapyrimidin-2-ylamino)-phenyl]-cyclopentanecarboxylic acid methyl ester

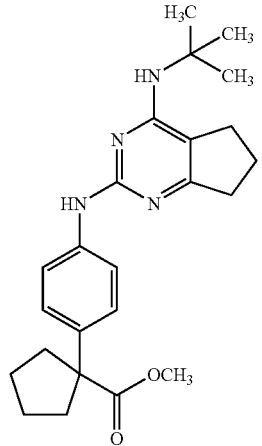

The title compound was afforded as a white solid following the procedure as described in Example 1, step (iv) (0.5 g, 80% yield).

$^1$H NMR (CDCl$_3$, 300 MHz) δ10.29 (bs, 1H), 7.52 (d, J=9 Hz, 2H), 7.33 (d, J=9 Hz, 2H), 5.05 (bs, 1H), 3.59 (s, 3H), 3.02 (t, J=7.5 Hz, 2H), 2.64-2.57 (m, 4H), 2.21-2.16 (m, 2H), 1.91-1.82 (m, 2H), 1.73-1.70 (m, 4H), 1.50 (s, 9H).

LC-MSD (ES+): (m/z) 409 [(M+H)$^+$, 100].

Step (iii): Synthesis of 1-[4-(4-tert-butylaminono-6,7-dihydro-5H-cyclopentapyrimidin-2-ylamino)-phenyl]-cyclopentanecarboxylic acid

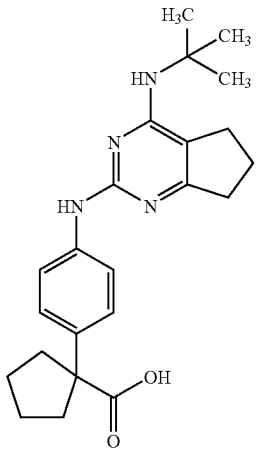

The title compound was afforded as a white solid following the procedure as described in Example 1, step (v) (0.35 g, 73% yield).

$^1$H NMR (CDCl$_3$+CD$_3$OD, 300 MHz), δ7.38-7.28 (m, 4H), 2.86 (t, J=7.5 Hz, 2H), 2.52-2.47 (m, 4H), 2.08-2.02 (m, 2H), 1.80-1.72 (m, 2H), 1.69-1.58 (m, 4H), 1.28 (s, 9H).

LC-MSD (ES+): (m/z) 395 [(M+H)$^+$, 100].

HPLC: Inertsil ODS-3V C18, 20:80 [KH$_2$PO$_4$ (0.01 M, pH 3.2): CH$_3$CN], gradient, PDA 260 nm, R$_t$ 12.25 min, purity 98.69%.

Example 11

Synthesis of 1-[4-(4-cyclopentylamino-6,7-dihydro-5H-cyclopentapyrimidin-2-ylamino)-phenyl]-cyclobutanecarboxylic acid

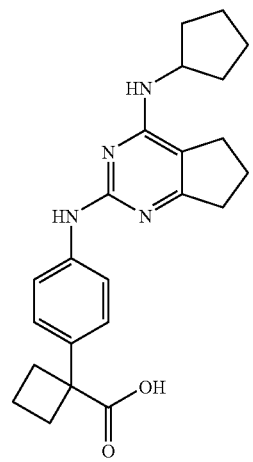

The title compound was afforded as a white solid following the procedure as described in Example 10 except in step (i) cyclopentylamine was used instead of tert-butylamine. (0.45 g, 79% yield).

$^1$H NMR (CDCl$_3$, 300 MHz), δ10.18 (s, 1H), 7.60 (d, J=8.7 Hz, 2H), 7.24 (d, J=8.7 Hz, 2H), 5.91 (bs, 1H), 4.38 (bs, 1H), 2.92-2.80 (m, 3H), 2.66-2.45 (m, 4H), 2.11-2.02 (m, 6H), 1.90-1.61 (m, 8H).

LC-MSD (ES+): (m/z) 393 [(M+H)$^+$, 100].

HPLC: Inertsil ODS-3V C18, 20:80 [KH$_2$PO$_4$ (0.01 M, pH 3.2): CH$_3$CN], gradient, PDA 264 nm, R$_t$ 12.07 min, purity 98.72%.

Example 12

Synthesis of 1-{4-[2-(3-fluoro-phenylamino)-6,7-dihydro-5H-cyclopentapyrimidin-4-ylamino]-phenyl}-cyclobutanecarboxylic acid

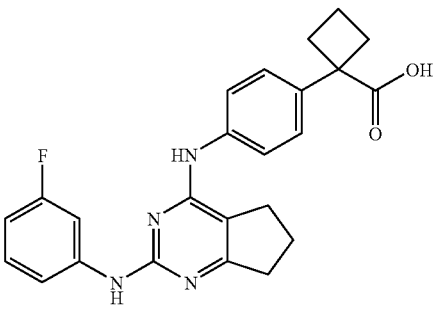

The title compound was obtained as a white solid following the procedure as described in Example 4 except in step (iv) 3-fluoroaniline was used instead of morpholine (58% yield).

$^1$H NMR (DMSO-d$_6$, 400 MHz): δ 12.20 (bs, 1H), 9.80 (bs, 1H), 9.20 (bs, 1H), 7.71-7.62 (m, 3H), 7.39-7.20 (m, 4H), 6.74-6.68 (m, 1H), 2.92-2.72 (m, 6H), 2.40-2.34 (m, 2H), 2.15-1.82 (m, 4H).

LC-MSD (ES+): (m/z) 419 [(M+H)$^+$, 100].

HPLC: ACE5 C18, 20:80 [KH$_2$PO$_4$ (0.01 M, pH 3.2): CH$_3$CN], gradient, PDA 269 nm, R$_t$ 9.95 min, purity 99.70%.

Example 13

Synthesis of 1-[4-(2-cyclopentylamino-6,7-dihydro-5H-cyclopentapyrimidin-4-ylamino)-phenyl]-cyclobutanecarboxylic acid

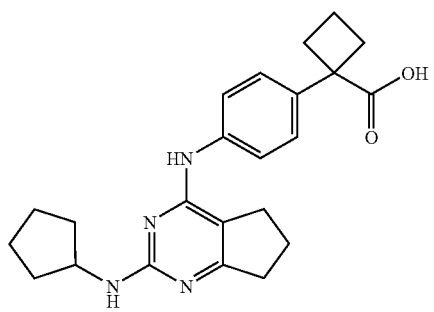

Step (i): Synthesis of 1-[4-(2-cyclopentylamino-6,7-dihydro-5H-cyclopentapyrimidin-4-ylamino)-phenyl]-cyclobutanecarboxylic acid methyl ester

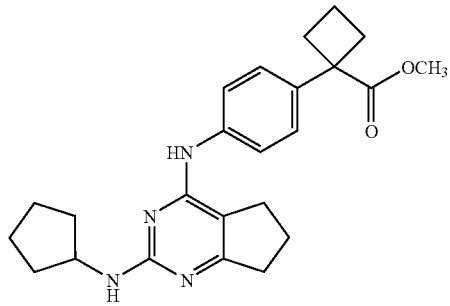

The title compound was obtained as a light brown solid following the procedure as described in Example 4, step (iv) except cyclopentylamine was used instead of morpholine, diisopropylethylamine and isopropanol (98% yield).

$^1$H NMR (CDCl$_3$, 300 MHz): δ 7.62 (d, J=8.2 Hz, 2H), 7.26 (d, J=8.2 Hz, 2H), 6.26 (bs, 1H), 4.28-4.04 (m, 1H), 3.62 (s, 3H), 2.88-2.78 (m, 4H), 2.74-2.62 (m, 2H), 2.56-2.42 (m, 2H), 2.19-2.01 (m, 6H), 1.78-1.46 (m, 6H).

LC-MSD (ES+): (m/z) 407 [(M+H)$^+$, 100].

Step (ii): Synthesis of 1-[4-(2-cyclopentylamino-6,7-dihydro-5H-cyclopentapyrimidin-4-ylamino)-phenyl]-cyclobutanecarboxylic acid

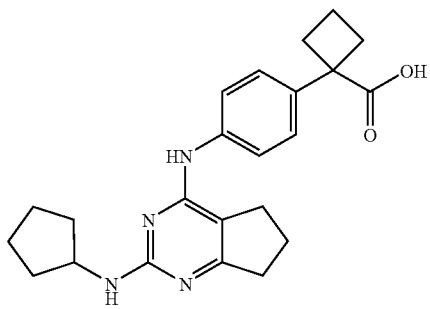

The title compound was obtained as a white solid following the procedure as described in Example 4, step (v) (58% yield).

$^1$H NMR (CDCl$_3$+CD$_3$OD, 300 MHz): δ 7.58 (d, J=8.1 Hz, 2H), 7.25 (d, J=8.1 Hz, 2H), 4.14-4.06 (m, 1H), 2.89 (t, J=7.8 Hz, 2H), 2.82-2.67 (m, 4H), 2.47-2.36 (m, 2H), 2.14-1.53 (m, 12H).

LC-MSD (ES+): (m/z) 393 [(M+H)$^+$, 100].

HPLC: Inertsil ODS-3V C18, 20:80 [KH$_2$PO$_4$ (0.01 M, pH 3.2): CH$_3$CN], gradient, PDA 220 nm, R$_t$ 12.29 min, purity 97.57%.

Example 14

Synthesis of 1-{4-[2-(cyclopropylmethyl-amino)-6,7-dihydro-5H-cyclopentapyrimidin-4-ylamino]-phenyl}-cyclobutanecarboxylic acid

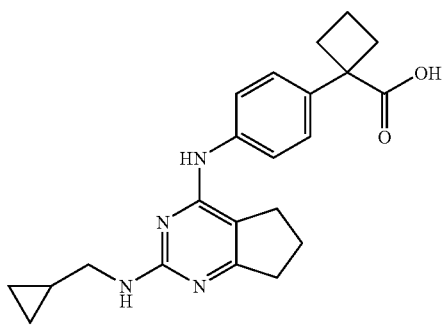

The title compound was obtained as a white solid following the procedure as described in Example 13, except cyclopropylmethylamine was used instead of cyclopentylamine.

$^1$H NMR (DMSO-d$_6$, 400 MHz): δ 12.2 (bs 1H), 8.22 (bs, 1H), 7.81 (d, J=8.2 Hz, 2H), 7.19 (d, J=8.2 Hz, 2H), 6.41 (bs, 1H), 3.19-3.09 (m, 2H), 2.74-2.32 (m, 8H), 2.01-1.72 (m, 4H), 1.01-1.07 (m, 1H), 0.51-0.40 (m, 2H), 0.35-0.22 (m, 2H).

LC-MSD (ES+): (m/z) 379 [(M+H)$^+$, 100].

HPLC: Inertsil ODS-3V C18, 20:80 [KH$_2$PO$_4$ (0.01 M, pH 3.2): CH$_3$CN], gradient, PDA 210 nm, R$_t$ 6.10 min, purity 97.60%.

Example 15

Synthesis of 1-{4-[2-(bis-cyclopropylmethyl-amino)-6,7-dihydro-5H-cyclopentapyrimidin-4-ylamino]-phenyl}-cyclobutane-carboxylic acid

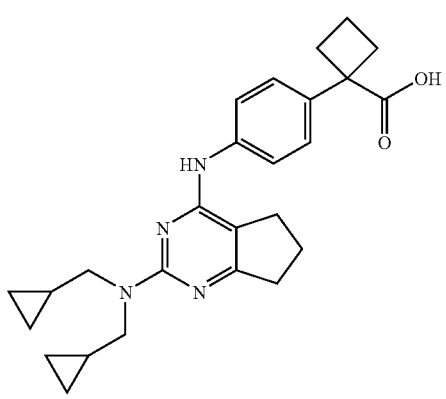

Step (i): Synthesis of 1-{4-[2-(bis-cyclopropylmethyl-amino)-6,7-dihydro-5H-cyclopentapyrimidin-4-ylamino]-phenyl}-cyclobutanecarboxylic acid methyl ester

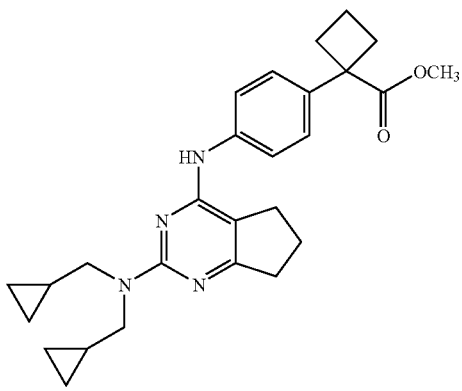

The title compound was obtained as a light yellow solid following the procedure as described in Example 4, step (iv), except bis-cyclopropylmethyl-amine (prepared following the literature method disclosed in U.S. Pat. No. 3,546,295) was used instead of morpholine, diisopropylethylamine and isopropanol (51% yield).
$^1$H NMR (CDCl$_3$, 300 MHz): δ 7.59 (d, J=6.9 Hz, 2H), 7.27 (d, J=6.9 Hz, 2H), 3.65-3.63 (m, 7H), 2.88-2.47 (m, 6H), 2.11-1.88 (m, 6H), 1.23-1.14 (m, 2H), 0.48-0.29 (m, 8H).
LC-MSD (ES+): (m/z) 447 [(M+H)$^+$, 100].
HPLC: Inertsil ODS-3V C18, 20:80 [KH$_2$PO$_4$ (0.01 M, pH 3.2): CH$_3$CN], gradient, PDA 264 nm, R$_t$ 15.49 min, purity 98.37%.

Step (ii): Synthesis of 1-{4-[2-(bis-cyclopropylmethyl-amino)-6,7-dihydro-5H-cyclopentapyrimidin-4-ylamino]-phenyl}-cyclobutane-carboxylic acid

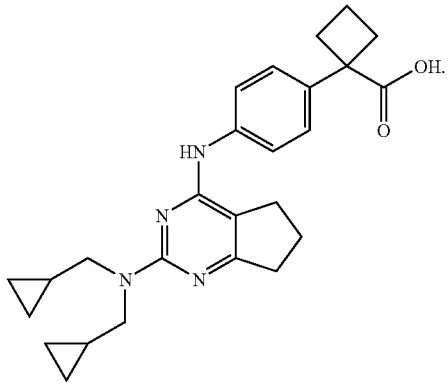

The title compound was obtained as a white solid following the procedure as described in Example 4, step (v) (50% yield).
$^1$H NMR (CDCl$_3$+CD$_3$OD, 300 MHz): δ 7.52 (d, J=8.7 Hz, 2H), 7.29 (d, J=8.7 Hz, 2H), 3.64-3.58 (m, 4H) 3.20 (t, J=7.5 Hz, 2H), 2.85-2.72 (m, 4H), 2.48-2.40 (m, 2H), 2.15-1.82 (m, 4H), 1.08-1.02 (m, 2H), 0.48-0.25 (m, 8H).
LC-MSD (ES+): (m/z) 433 [(M+H)$^-$, 100].
HPLC: Inertsil ODS-3V C18, 20:80 [KH$_2$PO$_4$ (0.01 M, pH 3.2): CH$_3$CN], gradient, PDA 264 nm, R$_t$ 12.99 min, purity 98.28%.

Example 16

Synthesis of 1-{4-[2-(4-methanesulfonyl-phenyl)-6,7-dihydro-5H-cyclopentapyrimidin-4-ylamino]-phenyl}-cyclobutanecarboxylic acid

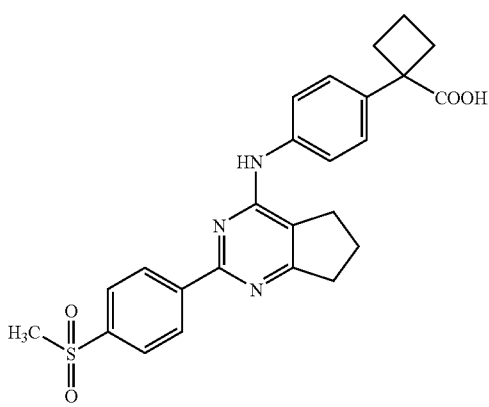

Step (i): Synthesis of 4-chloro-2-(4-methanesulfonyl-phenyl)-6,7-dihydro-5H-cyclopentapyrimidine

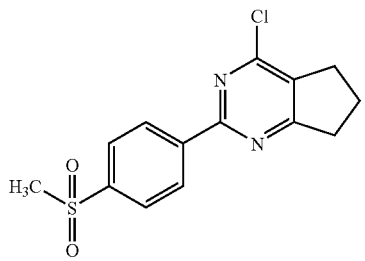

A solution of trimethylaluminum in toluene (2M, 26 mL, 52 mmol) was added slowly under nitrogen to a suspension of ammonium chloride (3.0 g, 55 mmol) in anhydrous toluene at 0° C.-5° C. The mixture was then stirred at a temperature in the range of 15° C. to 40° C. for 20 min before addition of a solution of 4-methanesulfonyl-benzonitrile (5.4 g, 30 mmol) in toluene. The resulting mixture was then heated at 80° C. under stirring for 10 hours. Thereafter, the mixture was cooled to a temperature in the range of 15° C. to 40° C. MeOH was added slowly to quench the reaction and stirred at a temperature in the range of 15° C. to 40° C. for 1 hour. Thereafter, the precipitate was filtered and washed with MeOH (3×30 mL). The filtrate and the washings were combined and concentrated under reduced pressure. The resultant semi-solid was dried under vacuum. The material was dissolved in anhydrous ethanol (20 mL) before addition of methyl-2-oxo-cyclopentanecarboxylate (1.3 mL, 10 mmol) and K$_2$CO$_3$ (2.06 g, 15 mmol) and then the mixture was heated to reflux for a period over 6-15 hours. Thereafter, volatiles were evaporated under reduced pressure, cooled to a temperature in the range of 15° C. to 40° C. and diluted with water. The resulting precipitate was filtered and washed thoroughly with water followed by ether and dried in vacuum. The solid was mixed with phosphorus oxychloride (4 mL) and heated to reflux for 3 hours. Thereafter, volatiles were evaporated under reduced pressure and the mixture was poured over ice-water. The product was extracted with dichloromethane (3×60 mL). The combined organic extracts were washed with brine, dried over anhydrous Na$_2$SO$_4$, filtered, and the filtrate was evaporated under reduced pressure to afford the title compound as a light yellow solid (0.71 g, 79% yield).

$^1$H NMR (CDCl$_3$, 300 MHz): δ 8.64 (dd, J=6.9, 1.8 Hz, 2H), 8.04 (dd, J=6.9, 1.8 Hz, 2H), 3.19-3.03 (m, 7H), 2.26-2.21 (m, 2H);

LC-MSD (ES+): (m/z) 309 [(M+H)$^+$, 100].

Step (ii): Synthesis of 1-{4-[2-(4-methanesulfonyl-phenyl)-6,7-dihydro-5H-cyclopentapyrimidin-4-ylamino]-phenyl}-cyclobutanecarboxylic acid methyl ester

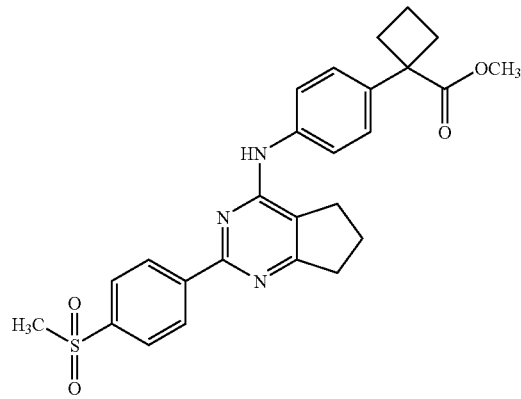

The title compound was obtained as a light yellow solid following the procedure as described in Example 1, step (iv), except 1-(4-amino-phenyl)-cyclobutanecarboxylic acid methyl ester was used instead of 1-(4-amino-phenyl)-cyclopentanecarboxylic acid methyl ester (53% yield).

$^1$H NMR (CDCl$_3$, 300 MHz): δ 8.61 (d, J=8.4 Hz, 2H), 8.04 (d, J=8.4 Hz, 2H), 7.67 (d, J=8.5 Hz, 2H), 7.37 (d, J=8.5 Hz, 2H), 6.58 (bs, 1H), 3.67 (s, 3H), 3.20-3.00 (m, 5H), 2.94-2.81 (m, 4H), 2.68-2.51 (m, 2H), 2.40-2.22 (m, 2H), 2.16-1.84 (m, 2H).

LC-MSD (ES+): (m/z) 478 [(M+H)$^+$, 100].

Step (iii): Synthesis of 1-{4-[2-(4-methanesulfonyl-phenyl)-6,7-dihydro-5H-cyclopentapyrimidin-4-ylamino]-phenyl}-cyclobutanecarboxylic acid

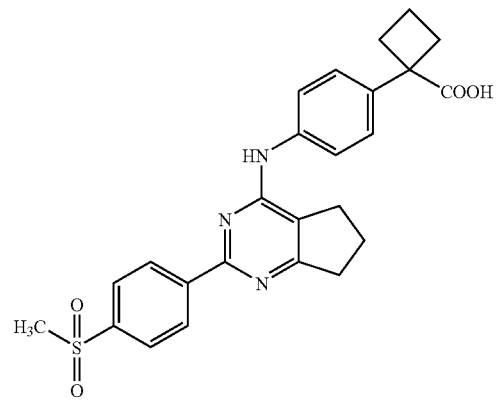

The title compound was afforded as a white solid following the procedure as described in Example 1, step (v) (91% yield).

$^1$H NMR (CDCl$_3$+CD$_3$OD, 300 MHz): δ 8.54 (d, J=8.4 Hz, 2H), 8.04 (d, J=8.4 Hz, 2H), 7.57 (d, J=6.9 Hz, 2H), 7.34 (d, J=6.9 Hz, 2H), 3.35-3.08 (m, 2H), 3.05 (s, 3H), 2.84-2.51 (m, 4H), 2.51-2.42 (m, 2H), 2.38-2.26 (m, 2H), 2.16-1.82 (m, 2H).

LC-MSD (ES+): (m/z) 464 [(M+H)$^+$, 100].

HPLC: Inertsil ODS-3V C18, 20:80 [KH$_2$PO$_4$ (0.01 M, pH 3.2): CH$_3$CN], gradient, PDA 264 nm, R$_t$ 15.0 min, purity 95.46%.

Example 17

Synthesis of 1-[4-(2-p-tolyl-6,7-dihydro-5H-cyclopentapyrimidin-4-ylamino)-phenyl]-cyclobutanecarboxylic acid

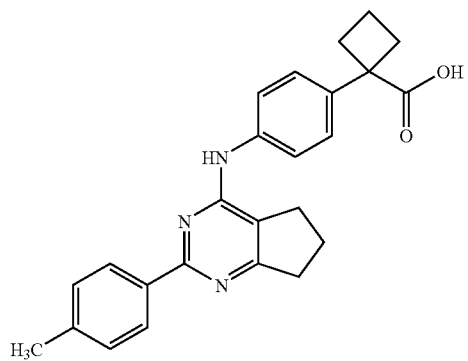

Step (i): Synthesis of 1-[4-(2-p-tolyl-6,7-dihydro-5H-cyclopentapyrimidin-4-ylamino)-phenyl]-cyclobutanecarboxylic acid methyl ester

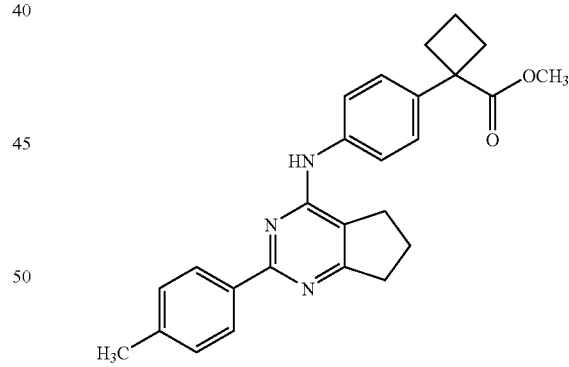

The title compound was obtained as a light yellow solid following the procedure as described in Example 1, step (iv), except 4-chloro-2-p-tolyl-6,7-dihydro-5H-cyclopentapyrimidine and 1-(4-amino-phenyl)-cyclobutanecarboxylic acid methyl ester were used instead of 4-chloro-2-cyclopentyl-6,7-dihydro-5H-cyclopentapyrimidine and 1-(4-amino-phenyl)-cyclopentanecarboxylic acid methyl ester, respectively (99% yield).

$^1$H NMR (CDCl$_3$, 300 MHz): δ 8.28 (d, J=8.4 Hz, 2H), 7.66 (bs, 1H), 7.29 (d, J=8.4 Hz, 2H), 7.67 (d, J=8.5 Hz, 4H), 3.64 (s, 3H), 3.41-3.32 (m, 2H), 2.94-2.77 (m, 4H), 2.54-2.44 (m, 2H), 2.38 (s, 3H), 2.25-2.20 (m, 2H), 2.08-1.84 (m, 2H).

LC-MSD (ES+): (m/z) 414 [(M+H)⁺, 100].

HPLC: Inertsil ODS-3V C18, 20:80 [KH$_2$PO$_4$ (0.01 M, pH 3.2): CH$_3$CN], gradient, PDA 264 nm, R$_t$ 21.32 min, purity 95.61%.

Step (ii): Synthesis of 1-[4-(2-p-tolyl-6,7-dihydro-5H-cyclopentapyrimidin-4-ylamino)-phenyl]-cyclobutane-carboxylic acid

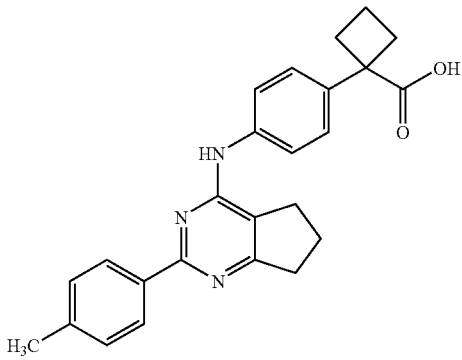

The title compound was obtained as a white solid following the procedure as described in Example 16, except p-tolunitrile was used instead of 4-methanesulfonyl-benzonitrile in step (i) (40% yield).

$^1$H NMR (CDCl$_3$+CD$_3$OD, 300 MHz): δ 8.16 (d, J=8.1 Hz, 2H), 7.64 (d, J=8.4 Hz, 2H), 7.30-7.18 (m, 4H), 3.06 (t, J=7.5 Hz, 2H), 2.77-2.50 (m, 4H), 2.56-2.43 (m, 2H), 2.40 (s, 3H), 2.28-2.19 (m, 2H), 2.15-1.82 (m, 2H).

LC-MSD (ES+): (m/z) 400 [(M+H)⁺, 100].

HPLC: Inertsil ODS-3V C18, 20:80 [KH$_2$PO$_4$ (0.01 M, pH 3.2): CH$_3$CN], gradient, PDA 264 nm, R$_t$ 15.70 min, purity 98.98%.

Example 18

Synthesis of 1-[4-(2-phenyl-6,7-dihydro-5H-cyclopentapyrimidin-4-ylamino)-phenyl]-cyclobutanecarboxylic acid

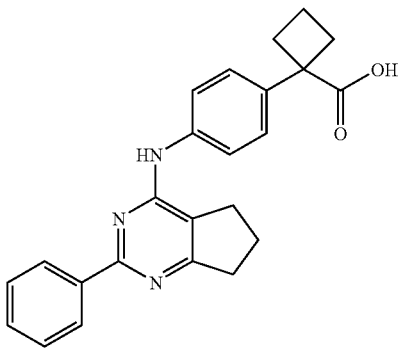

Step (i): Synthesis of 1-[4-(2-Phenyl-6,7-dihydro-5H-cyclopentapyrimidin-4-ylamino)-phenyl]-cyclobutanecarboxylic acid methyl ester

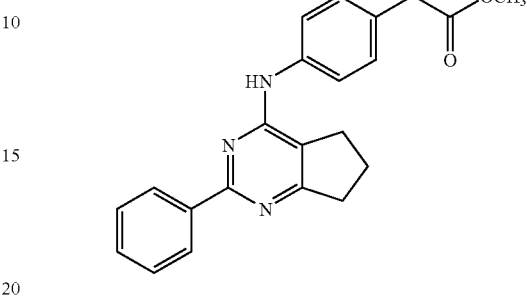

The title compound was obtained as a white solid following the procedure as described in Example 1, step (iv), except 4-chloro-2-phenyl-6,7-dihydro-5H-cyclopentapyrimidine and 1-(4-amino-phenyl)-cyclobutanecarboxylic acid methyl ester were used instead of 4-chloro-2-cyclopentyl-6,7-dihydro-5H-cyclopentapyrimidine and 1-(4-amino-phenyl)-cyclopentanecarboxylic acid methyl ester, respectively (98% yield).

$^1$H NMR (CDCl$_3$, 300 MHz): δ 9.5 (bs, 1H), 8.42 (d, J=8.2 Hz, 2H), 7.81 (d, J=8.2 Hz, 2H), 7.61-7.42 (m, 3H), 7.38-7.27 (m, 2H), 3.60 (s, 3H), 3.51-3.40 (m, 2H), 3.22-3.01 (m, 4H), 2.93-2.78 (m, 2H), 2.58-2.42 (m, 2H), 2.21-1.82 (m, 2H).

LC-MSD (ES+): (m/z) 400 [(M+H)⁺, 100].

Step (ii): Synthesis of 1-[4-(2-phenyl-6,7-dihydro-5H-cyclopentapyrimidin-4-ylamino)-phenyl]-cyclobutanecarboxylic acid

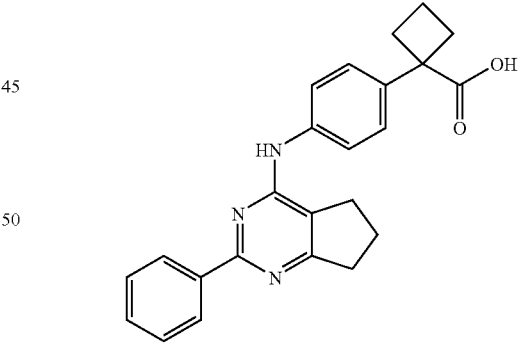

The title compound was afforded following the procedure as described in Example 4, step (v) as a white solid (80% yield).

$^1$H NMR (CDCl$_3$+CD$_3$OD, 300 MHz): δ 8.25 (d, J=7.5 Hz, 2H), 7.63-7.44 (m, 5H), 7.31 (d, J=8.4 Hz, 2H), 3.34-3.22 (m, 2H), 2.94-2.73 (m, 4H), 2.51-2.39 (m, 2H), 2.28-2.19 (m, 2H), 2.18-1.80 (m, 2H).

LC-MSD (ES+): (m/z) 386 [(M+H)⁺, 100].

HPLC: Betasil ODS-3V C18, 20:80 [KH$_2$PO$_4$ (0.01 M, pH 3.2): CH$_3$CN], gradient, PDA 290 nm, R$_t$ 15.24 min, purity 97.01%.

Example 19

Synthesis of 1-{4-[2-(2-oxo-pyrrolidin-1-yl)-6,7-dihydro-5H-cyclopentapyrimidin-4-ylamino]-phenyl}-cyclobutanecarboxylic acid methyl ester

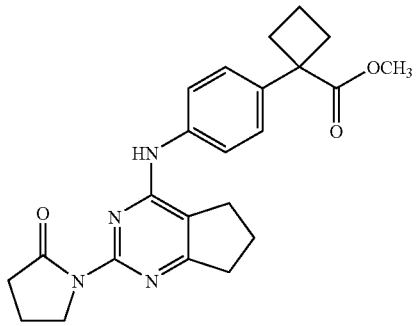

A glass tube was charged with 1-[4-(2-chloro-6,7-dihydro-5H-cyclopentapyrimidin-4-ylamino)-phenyl]-cyclobutanecarboxylic acid methyl ester (0.5 g, 1.4 mmol), 2-pyrrolidinone (0.17 g, 2 mmol) and alternatively purged and backfilled with nitrogen. Thereafter, tris(dibenzylideneacetone)dipalladium(0) (0.05 g), 4,5-bis(diphenylphosphino)-9,9-dimethylxanthine (0.05 g), cesium carbonate (0.7 g, 2.2 mmol) and anhydrous 1,4-dioxane (6 mL) were introduced in the tube and again flushed with nitrogen. The reaction was stirred at a temperature in the range of 40° C. to 100° C. under stirring until complete as evidenced by the disappearance of starting chloro compound (TLC). The resulting mixture was cooled to a temperature in the range of 15° C. to 40° C., diluted with ethyl acetate (20 mL), filtered through Celite, and the filtrate was concentrated under reduced pressure. The residue was purified by flash chromatography over silica gel to afford the title compound as a light yellow solid (0.44 g, 78% yield).

$^1$H NMR (CDCl$_3$, 300 MHz), δ 7.83 (d, J=8.4 Hz, 2H), 7.31 (d, J=8.4 Hz, 2H), 6.85 (bs, 1H), 4.09 (t, J=6.9 Hz, 2H), 3.63 (s, 3H), 2.96 (t, J=7.5 Hz, 2H), 2.86-2.76 (m, 3H), 2.71 (t, J=8.0 Hz, 2H), 2.58-2.44 (m, 2H), 2.19-2.07 (m, 5H), 1.88-1.82 (m, 1H), 1.68-1.59 (m, 1H).

LC-MSD (ES+): (m/z) 407 [(M+H)$^+$, 100].

HPLC: Betasil ODS-3V C18, 20:80 [KH$_2$PO$_4$ (0.01 M, pH 3.2): CH$_3$CN], gradient, PDA 264 nm, R$_t$ 11.87 min, purity 95.97%.

Example 20

Synthesis of 1-{4-[2-(6-methyl-pyridin-3-yl)-6,7-dihydro-5H-cyclopentapyrimidin-4-ylamino]-phenyl}-cyclobutanecarboxylic acid

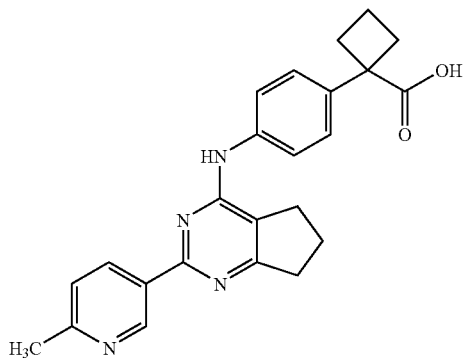

Step (i): Synthesis of 4-chloro-2-(6-methyl-pyridin-3-yl)-6,7-dihydro-5H-cyclopentapyrimidine

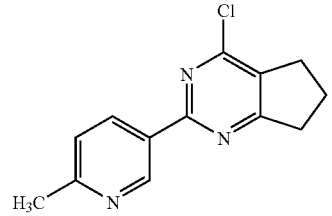

The title compound was afforded as a light yellow solid following the procedure as described in Example 16, step (i) except 5-cyano-2-methylpyridine was used instead of 4-methanesulfonyl-benzonitrile (38% yield).

$^1$H NMR (CDCl$_3$, 300 MHz): δ 9.48 (d, J=2.1 Hz, 1H), 8.59 (dd, J=8.6, 2.1 Hz, 1H), 7.28 (d, J=8.6 Hz, 1H), 3.15-3.0 (m, 4H), 2.65 (s, 3H), 2.63-2.18 (m, 2H).

LC-MSD (ES+): (m/z) 246 [(M+H)$^+$, 100].

Step (ii): Synthesis of 1-{4-[2-(6-methyl-pyridin-3-yl)-6,7-dihydro-5H-cyclopentapyrimidin-4-ylamino]-phenyl}-cyclobutanecarboxylic acid methyl ester

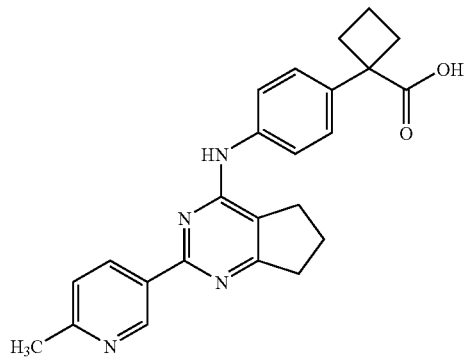

The title compound was afforded as a light yellow solid following the procedure as described in Example 16, step (ii) (77% yield).

$^1$H NMR (CDCl$_3$, 300 MHz): δ 9.56 (s, 1H), 9.42 (d, J=8.6 Hz, 1H), 7.82 (bs, 1H), 7.72 (d, J=8.6 Hz, 2H), 7.59 (d, J=8.4 Hz, 2H), 7.35 (d, J=8.4 Hz, 1H), 3.68 (s, 3H), 3.19 (t, J=7.8 Hz, 2H), 2.97-2.79 (m, 7H), 2.56-2.46 (m, 2H), 2.26-2.21 (m, 2H), 2.07-1.87 (m, 2H).

LC-MSD (ES+): (m/z) 415 [(M+H)$^+$, 100].

HPLC: Betasil ODS-3V C18, 20:80 [KH$_2$PO$_4$ (0.01 M, pH 3.2): CH$_3$CN], gradient, PDA 280 nm, R$_t$ 17.89 min, purity 99.73%.

Step (iii): Synthesis of 1-{4-[2-(6-methyl-pyridin-3-yl)-6,7-dihydro-5H-cyclopentapyrimidin-4-ylamino]-phenyl}-cyclobutanecarboxylic acid

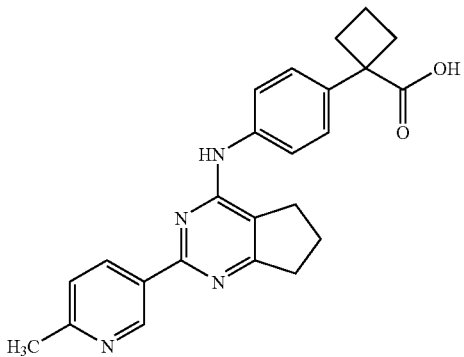

The title compound was afforded as a white solid following the procedure as described in Example 16, step (iii) (63% yield).

¹H NMR (CDCl₃+CD₃OD, 300 MHz): δ 8.16 (d, J=1.8 Hz, 1H), 8.73 (dd, J=8.1, 1.8 Hz, 1H), 7.54 (d, J=8.6, Hz, 2H), 7.40 (d, J=8.1 Hz, 1H), 7.28 (d, J=8.6 Hz, 2H), 3.0 (t, J=7.8 Hz, 2H), 2.81-2.71 (m, 4H), 2.63 (s, 3H), 2.47-2.38 (m, 2H), 2.18-2.08 (m, 2H), 1.99-1.78 (m, 2H).

LC-MSD (ES+): (m/z) 401 [(M+H)⁺, 100].

HPLC: Betasil ODS-3V C18, 20:80 [KH₂PO₄ (0.01 M, pH 3.2): CH₃CN], gradient, PDA 280 nm, R_t 12.76 min, purity 97.34%.

Example 21

Synthesis of {1-[4-(2-morpholin-4-yl-6,7-dihydro-5H-cyclopentapyrimidin-4-ylamino)-phenyl]-cyclobutyl}-methanol

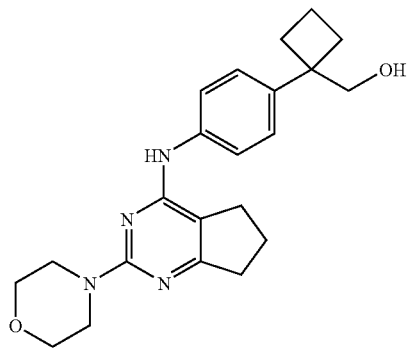

Lithium aluminumhydride (2M solution in tetrahydrofuran, 1.5 mL) was added drop-wise to a solution of 1-[4-(2-morpholin-4-yl-6,7-dihydro-5H-cyclopentapyrimidin-4-ylamino)-phenyl]-cyclobutanecarboxylic acid (0.61 g, 1.52 mmol) in anhydrous tetrahydrofuran (10 mL) at 0° C. to 5° C. After addition, the reaction mixture was warmed to a temperature in the range of 15° C. to 40° C. and stirring continued for an additional 10 hours. The reaction was quenched by addition of aqueous sodium hydroxide. The precipitated solid was filtered and washed with ethyl acetate. The combined filtrates were washed with brine, dried over Na₂SO₄, filtered, and concentrated to yield a white solid. The title compound was afforded following purification by column chromatography (silica gel) as a white solid (0.56 g, 80% yield).

¹H NMR (CDCl₃, 300 MHz): δ 7.56 (d, J=8.7 Hz, 2H), 7.13 (d, J=8.7 Hz, 2H), 6.11 (bs, 1H), 3.84-3.72 (m, 8H), 3.70 (bs, 1H), 2.92-2.79 (m, 2H), 2.67 (t, J=7.2 Hz, 2H), 2.38-2.04 (m, 8H), 1.96-1.84 (m, 2H).

LC-MSD (ES+): (m/z) 381 [(M+H)⁺, 100].

HPLC: Betasil ODS-3V C18, 20:80 [KH₂PO₄ (0.01 M, pH 3.2): CH₃CN], gradient, PDA 230 nm, R_t 10.95 min, purity 95.41%.

Example 22

Synthesis of 1-[4-(2-morpholin-4-yl-6,7-dihydro-5H-cyclopentapyrimidin-4-ylamino)-phenyl]-cyclopentanecarboxylic acid

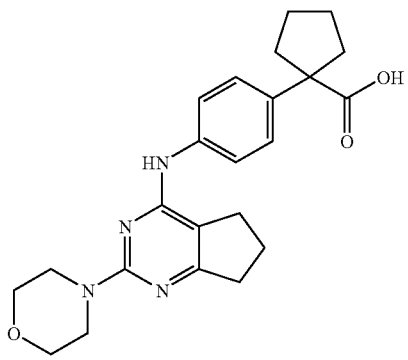

Step (i): Synthesis of 1-[4-(2-Morpholin-4-yl-6,7-dihydro-5H-cyclopentapyrimidin-4-ylamino)-phenyl]-cyclopentanecarboxylic acid methyl ester

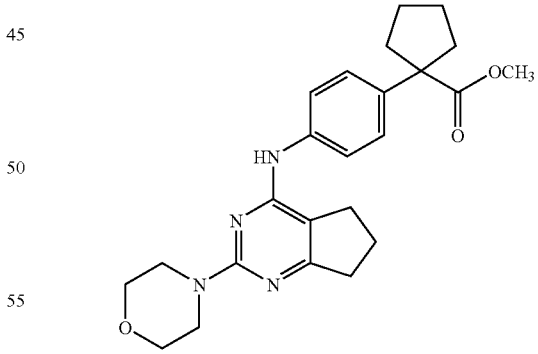

The title compound was prepared following the procedure as described in Example 2, step (ii) except 4-chloro-2-morpholin-4-yl-6,7-dihydro-5H-cyclopentapyrimidine is used instead of 4-chloro-2-cyclopentylmethyl-6,7-dihydro-5H-cyclopentapyrimidine. (96% yield).

¹H NMR (CDCl₃, 300 MHz): δ 7.53 (d, J=8.7 Hz, 2H), 7.33 (d, J=8.7 Hz, 2H), 6.5 (bs, 1H), 4.0 to 3.78 (m, 8H), 3.60 (s, 3H), 2.95-2.89 (m, 2H), 2.70-2.61 (m, 4H), 2.17-2.10 (m, 2H), 1.91-1.71 (m, 6H).

LC-MSD (ES+): (m/z) 423 [(M+H)+, 100].

HPLC: Betasil ODS-3V C18, 20:80 [KH$_2$PO$_4$ (0.01 M, pH 3.2): CH$_3$CN], gradient, PDA 280 nm, R$_t$ 12.62 min, purity 96.27%.

Step (ii): Synthesis of 1-[4-(2-morpholin-4-yl-6,7-dihydro-5H-cyclopentapyrimidin-4-ylamino)-phenyl]-cyclopentanecarboxylic acid

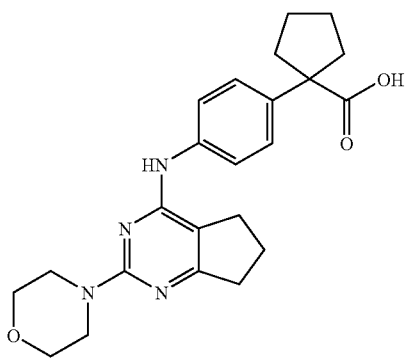

The title compound was prepared following the procedure as described in Example 2, step (iii) (58% yield).

$^1$H NMR (CDCl$_3$+CD$_3$OD, 300 MHz): δ 7.46 (d, J=8.7 Hz, 2H), 7.31 (d, J=8.7 Hz, 2H), 3.70-3.65 (m, 8H), 2.87-2.76 (m, 2H), 2.67-2.51 (m, 4H), 2.10-2.06 (m, 2H), 1.86-1.66 (m, 6H).

LC-MSD (ES+): (m/z) 409 [(M+H)+, 100].

HPLC: Betasil ODS-3V C18, 20:80 [KH$_2$PO$_4$ (0.01 M, pH 3.2): CH$_3$CN], gradient, PDA 280 nm, R$_t$ 10.54 min, purity 99.11%.

Example 23

Synthesis of {1-[4-(2-morpholin-4-yl-6,7-dihydro-5H-cyclopentapyrimidin-4-ylamino)-phenyl]-cyclopentyl}-methanol

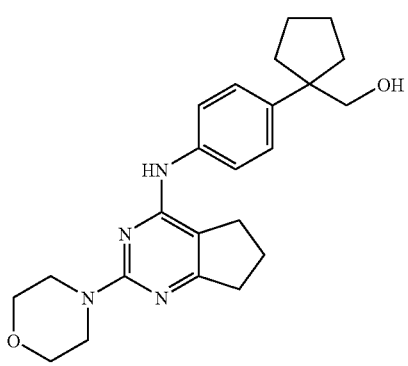

Lithium aluminumhydride (2M solution in tetrahydrofuran, 1.0 mL) was added drop-wise to a solution of 1-[4-(2-morpholin-4-yl-6,7-dihydro-5H-cyclopentapyrimidin-4-ylamino)-phenyl]-cyclopentanecarboxylic acid (0.3 g, 0.73 mmol) prepared using a procedure as described in example 22; in anhydrous tetrahydrofuran (10 mL) at 0° C. to 5° C. After addition, the reaction mixture was warmed to a temperature in the range of 15° C. to 40° C. and stirring continued for an additional 10 hours. The reaction was quenched by addition of aqueous sodium hydroxide. The precipitated solid was filtered and washed with ethyl acetate. The combined filtrates were washed with brine, dried over Na$_2$SO$_4$, filtered, and concentrated. The residue was purified by column chromatography (silica gel) to afford the title compound as a white solid (0.11 g, 39% yield).

$^1$H NMR (CDCl$_3$, 300 MHz): δ 7.55 (d, J=8.7 Hz, 2H), 7.25 (d, J=8.7 Hz, 2H), 6.09 (bs, 1H), 3.76-3.72 (m, 8H), 3.52 (bs, 1H), 2.80 (t, J=7.8 Hz, 2H), 2.66 (t, J=6.9 Hz, 2H), 2.12-1.72 (m, 12H).

LC-MSD (ES+): (m/z) 395 [(M+H)+, 100].

HPLC: Betasil ODS-3V C18, 20:80 [KH$_2$PO$_4$ (0.01 M, pH 3.2): CH$_3$CN], gradient, PDA 290 nm, R$_t$ 10.96 min, purity 96.81%.

Example 24

Synthesis of 1-[4-(4-morpholin-4-yl-6,7-dihydro-5H-cyclopentapyrimidin-2-ylamino)-phenyl]-cyclobutanecarboxylic acid

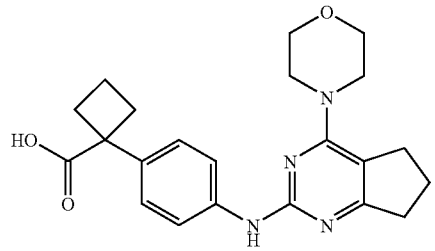

Step (i): Synthesis of 2-Chloro-4-morpholin-4-yl-6,7-dihydro-5H-cyclopentapyrimidine

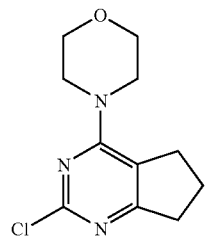

Morpholine (0.32 mL, 3.7 mmol) was added to a solution of 2,4-dichloro-6,7-dihydro-5H-cyclopentapyrimidine (0.5 g, 2.65 mmol) in anhydrous ethanol (5 mL) and stirred at a temperature in the range of 65° C. to 85° C. for 10 to 16 hours. Thereafter, the mixture was concentrated under reduced pressure and the crude was diluted with anhydrous ether. After standing at a temperature in the range of 5° C. to 10° C. for 2 hours, the precipitated solid was filtered and washed with ether. The solid was recrystallized from ethyl acetate to afford the title compound as a pale yellow solid (0.54 g, 86% yield).

$^1$H NMR (CDCl$_3$, 300 MHz): δ 4.10-3.94 (m, 4H), 3.90-3.76 (m, 4H), 3.36-3.20 (m, 2H), 3.10-2.90 (m, 2H), 2.29-2.12 (m, 2H).

LC-MSD (ES+): (m/z) 240 [(M+H)+, 100].

Step (ii): Synthesis of 1-[4-(4-Morpholin-4-yl-6,7-dihydro-5H-cyclopentapyrimidin-2-ylamino)-phenyl]-cyclobutanecarboxylic acid methyl ester

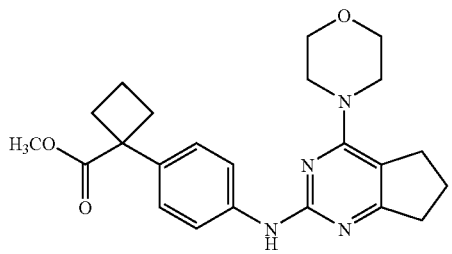

A solution of 2-chloro-4-morpholin-4-yl-6,7-dihydro-5H-cyclopentapyrimidine (0.53 g, 2.8 mmol) and 1-(4-aminophenyl)-cyclobutanecarboxylic acid methyl ester (0.57 g, 2.8 mmol) in anhydrous isopropanol (10 mL) was stirred under reflux for 18 hours. After cooling to a temperature in the range of 25° C. to 40° C., the mixture was concentrated under reduced pressure. The crude residue was purified by column chromatography (silica gel) to afford the title compound as a white solid (0.24 g, 27% yield).

$^1$H NMR (CDCl$_3$, 300 MHz): δ 7.53 (d, J=8.7 Hz, 2H), 7.25 (d, J=8.7 Hz, 2H), 6.96 (bs, 1H), 3.80-3.77 (m, 4H), 3.71-3.66 (m, 4H), 3.63 (s, 3H), 2.94-2.53 (m, 6H), 2.50-2.08 (m, 2H), 2.05-1.84 (m, 4H).

LC-MSD (ES+): (m/z) 409 [(M+H)$^+$, 100].

HPLC: Betasil ODS-3V C18, 20:80 [KH$_2$PO$_4$ (0.01 M, pH 3.2): CH$_3$CN], gradient, PDA 275 nm, R$_t$ 12.68 min, purity 91.43%.

Step (iii): Synthesis of 1-[4-(4-Morpholin-4-yl-6,7-dihydro-5H-cyclopentapyrimidin-2-ylamino)-phenyl]-cyclobutanecarboxylic acid

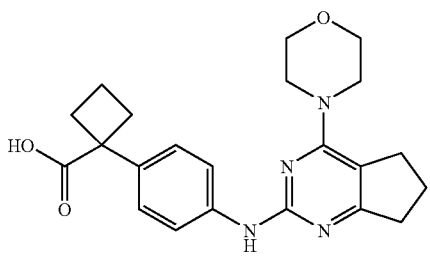

The title compound was prepared following the procedure as described in Example 4, step (v) (50% yield).

$^1$H NMR (CDCl$_3$, 300 MHz): δ 7.25 (d, J=8.7 Hz, 2H), 7.11 (d, J=8.7 Hz, 2H), 3.69-3.61 (m, 4H), 3.59-3.51 (m, 4H), 3.14-3.10 (m, 2H), 2.82-2.60 (m, 6H), 2.30-2.22 (m, 2H), 1.99-1.82 (m, 2H).

LC-MSD (ES+): (m/z) 395 [(M+H)$^+$, 100].

HPLC: Betasil ODS-3V C18, 20:80 [KH$_2$PO$_4$ (0.01 M, pH 3.2): CH$_3$CN], gradient, PDA 275 nm, R$_t$ 10.74 min, purity 95.07%.

Example 25

Synthesis of sodium 1-[4-(2-morpholin-4-yl-6,7-dihydro-5H-cyclopentapyrimidin-4-ylamino)-phenyl]-cyclobutanecarboxylate

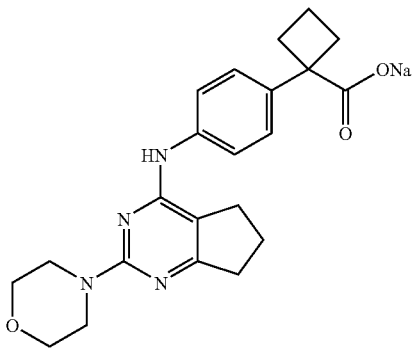

1-[4-(2-morpholin-4-yl-6,7-dihydro-5H-cyclopentapyrimidin-4-ylamino)-phenyl]-cyclobutanecarboxylic acid (0.39 g, 1 mmol) was suspended in anhydrous MeOH (15 mL). The mixture was stirred for 0.5 hours and then sodium tert-butoxide (0.096 g, 1 mmol) was added slowly. The mixture was then heated to reflux for 2 hours. After cooling to about 20 to 35° C., the mixture was filtered and the filtrate was concentrated under reduced pressure. The residue was triturated with acetone. The precipitate was filtered, washed with acetone and then recrystallized from acetone-MeOH to afford white solid (0.4 g, 96% yield).

$^1$H NMR (DMSO-d$_6$, 300 MHz): δ 8.28 (s, 1H), 7.52 (d, J=8.4 Hz, 2H), 7.13 (d, J=8.4 Hz, 2H), 3.61-3.58 (m, 8H), 2.68-2.60 (m, 6H), 2.15-1.59 (m, 6H).

LC-MSD (ES+): (m/z) 395 [(M+H)$^+$, 100].

HPLC: Betasil ODS-3V C18, 20:80 [KH$_2$PO$_4$ (0.01 M, pH 3.2): CH$_3$CN], gradient, PDA 290 nm, R$_t$ 10.07 min, purity 99.26%.

Example 26

Synthesis of 1-{4-[2-(4,4-difluoro-piperidin-1-yl)-6,7-dihydro-5H-cyclopentapyrimidin-4-ylamino]-phenyl}-cyclobutanecarboxylic acid

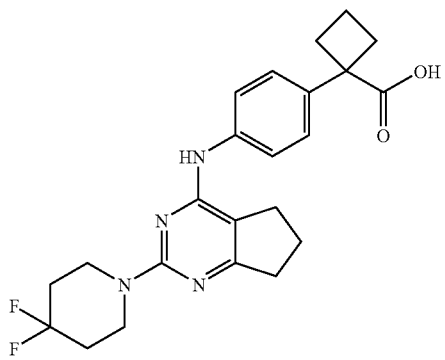

Step (i): Synthesis of 1-{4-[2-(4,4-Difluoro-piperidin-1-yl)-6,7-dihydro-5H-cyclopentapyrimidin-4-ylamino]-phenyl}cyclobutanecarboxylic acid methyl ester

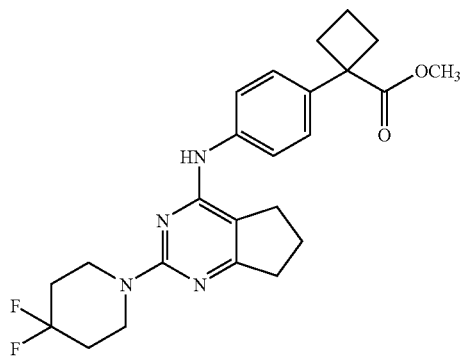

A mixture of 1-[4-(2-chloro-6,7-dihydro-5H-cyclopentapyrimidin-4-ylamino)-phenyl]-cyclobutanecarboxylic acid methyl ester (0.36 g, 1 mmol), 4,4-difluoropiperidine hydrochloride (0.23 g, 1.5 mmol), diisopropylethylamine (0.5 mL, 3 mmol) in anhydrous isopropanol (10 mL) was heated to reflux for 48 hours. Thereafter, the mixture was cooled to a temperature in the range of 40° C. to 60° C. and concentrated under reduced pressure. The residue was diluted with ethyl acetate, washed sequentially with water, brine, dried over sodium sulfate, filtered and concentrated under reduced pressure to yield a semi solid residue. Ether was added to the residue and the precipitates were filtered to afford the title compound as a white solid (0.34 g, 77% yield).
$^1$H NMR (CDCl$_3$, 300 MHz): δ 7.55 (d, J=8.7 Hz, 2H), 7.27 (d, J=8.7 Hz, 2H), 6.10 (bs, 1H), 3.96-3.90 (m, 4H), 3.65 (s, 3H), 2.84-2.76 (m, 4H), 2.70-2.63 (m, 2H), 2.54-2.47 (m, 2H), 2.13-1.93 (m, 8H).
LC-MSD (ES+): (m/z) 443 [(M+H)$^+$, 100].

Step (ii): Synthesis of 1-{4-[2-(4,4-difluoro-piperidin-1-yl)-6,7-dihydro-5H-cyclopentapyrimidin-4-ylamino]-phenyl}-cyclobutanecarboxylic acid

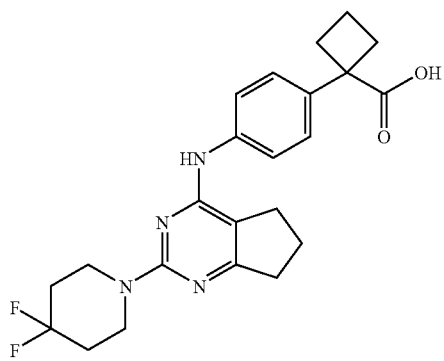

The title compound was prepared following the procedure as described in Example 4, step (v) (94% yield).
$^1$H NMR (CDCl$_3$, 300 MHz): δ 7.39 (d, J=8.7 Hz, 2H), 7.22 (d, J=8.7 Hz, 2H), 3.94-3.88 (m, 4H), 3.05-3.0 (m, 2H), 2.77-2.66 (m, 4H), 2.42-2.32 (m, 2H), 2.13-1.74 (m, 8H).

LC-MSD (ES+): (m/z) 429 [(M+H)$^+$, 100].
HPLC: Betasil ODS-3V C18, 20:80 [KH$_2$PO$_4$ (0.01 M, pH 3.2): CH$_3$CN], gradient, PDA 275 nm, R$_t$ 13.51 min, purity 95.18%.

Example 27

Synthesis of 1-[4-(2-morpholin-4-yl-5,6,7,8-tetrahydro-quinazolin-4-ylamino)-phenyl]-cyclobutanecarboxylic acid

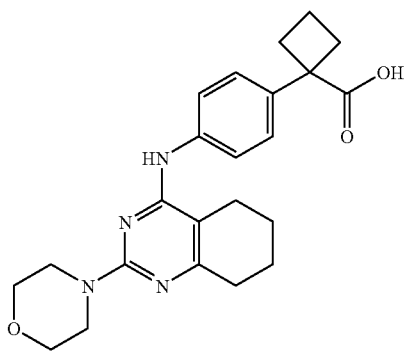

Step (i): Synthesis of 2,4-dichloro-5,6,7,8-tetrahydro-quinazoline

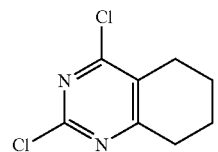

The title compound was prepared following the procedure as described in Example 4, step i-ii except 2-oxo-cyclohexanecarboxylic acid methyl ester was used instead of 2-oxo-cyclopentanecarboxylic acid methyl ester in step (i).
$^1$H NMR (CDCl$_3$, 300 MHz): δ 2.89-2.84 (m, 2H), 2.74-2.70 (m, 2H), 1.89-1.83 (m, 4H).
LC-MSD (ES+): (m/z) 203 [(M+H)$^+$, 100].

Step (ii): Synthesis of 1-[4-(2-Chloro-5,6,7,8-tetrahydro-quinazolin-4-ylamino)-phenyl]-cyclobutanecarboxylic acid methyl ester

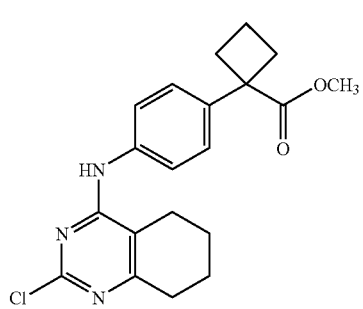

The title compound was prepared following the procedure as described in Example 4, step (iii) (69% yield).

$^1$H NMR (CDCl$_3$, 300 MHz): δ 7.56 (d, J=8.7 Hz, 2H), 7.31 (d, J=8.7 Hz, 2H), 6.44 (bs, 1H), 3.65 (s, 3H), 2.84-2.73 (m, 4H), 2.51-2.43 (m, 4H), 1.93-1.84 (m, 6H).

LC-MSD (ES+): (m/z) 372 [(M+H)$^+$, 100].

Step (iii): Synthesis of 1-[4-(2-morpholin-4-yl-5,6,7,8-tetrahydro-quinazolin-4-ylamino)-phenyl]-cyclobutanecarboxylic acid methyl ester

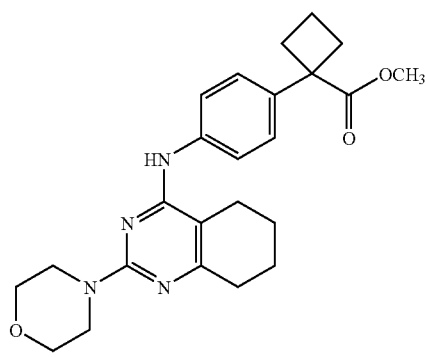

The title compound was prepared following the procedure as described in Example 4, step (iv) (77% yield).

$^1$H NMR (CDCl$_3$, 300 MHz): δ 7.57 (d, J=8.7 Hz, 2H), 7.26 (d, J=8.7 Hz, 2H), 6.26 (bs, 1H), 3.83-3.73 (m, 8H), 3.65 (s, 3H), 2.85-2.77 (m, 2H), 2.62-2.38 (m, 6H), 2.03-1.80 (m, 6H).

LC-MSD (ES+): (m/z) 423 [(M+H)$^+$, 100].

HPLC: Betasil ODS-3V C18, 30:70 [KH$_2$PO$_4$ (0.01 M, pH 3.2): CH$_3$CN], PDA 230 nm, R$_t$ 3.72 min, purity 97.58%.

Step (iv): Synthesis of 1-[4-(2-morpholin-4-yl-5,6,7,8-tetrahydro-quinazolin-4-ylamino)-phenyl]-cyclobutanecarboxylic acid

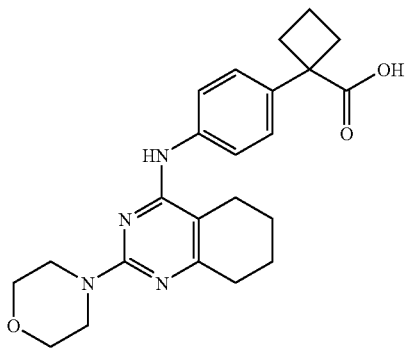

The title compound was prepared following the procedure as described in Example 4, step (v) (35% yield).

$^1$H NMR (CDCl$_3$, 300 MHz): δ 7.37 (d, J=8.7 Hz, 2H), 7.10 (d, J=8.7 Hz, 2H), 3.56-3.47 (m, 8H), 2.70-2.21 (m, 8H), 1.83-1.61 (m, 6H).

LC-MSD (ES+): (m/z) 409 [(M+H)$^+$, 100].

HPLC: Betasil ODS-3V C18, 20:80 [KH$_2$PO$_4$ (0.01 M, pH 3.2): CH$_3$CN], gradient, PDA 290 nm, R$_t$ 11.25 min, purity 93.58%.

Example 28

Synthesis of 1-{4-[4-(3,5-dimethyl-isoxazol-4-yl)-6,7-dihydro-5H-cyclopentapyrimidin-2-ylamino]-phenyl}-cyclobutanecarboxylic acid

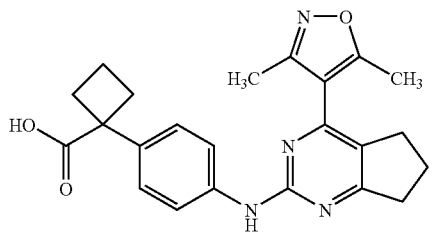

Step (i): Synthesis of 2-chloro-4-(3,5-dimethyl-isoxazol-4-yl)-6,7-dihydro-5H-cyclopentapyrimidine

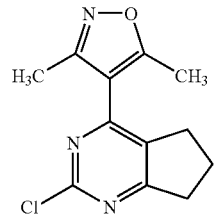

3,5-Dimethylisoxazole boronic acid (0.4 g, 2.8 mmol) was added to a solution of 2,4-dichloro-6,7-dihydro-5H-cyclopentapyrimidine (0.75 g, 4 mmol) in tetrahydrofuran (10 mL). The mixture was flushed with N$_2$ before addition of palladium acetate (0.07 g, 0.28 mmol) and triphenylphosphine (0.14 g, 0.56 mmol). Thereafter, 2M aqueous sodium carbonate solution was added and the mixture was refluxed with N$_2$. The mixture was stirred at a temperature in the range of 20° C. to 50° C. for 8 to 12 hours and then cooled to about 20 to 35° C. The mixture was diluted with water and the organic layer was separated. The aqueous layer was re-extracted with ethyl acetate. The organic extracts were combined, washed with brine, dried over sodium sulfate, filtered and concentrated under reduced pressure. The crude residue was purified by column chromatography (silica gel) to afford the title compound as a light yellow liquid (0.52 g, 53% yield).

$^1$H NMR (CDCl$_3$, 300 MHz): δ 3.08 (t, J=7.8 Hz, 2H), 2.83 (d, J=7.8 Hz, 2H), 2.41 (s, 3H), 2.30 (s, 3H), 2.23-2.16 (m, 2H).

LC-MSD (ES+): (m/z) 250 [(M+H)$^+$, 100].

Step (ii): Synthesis of 1-{4-[4-(3,5-dimethyl-isoxazol-4-yl)-6,7-dihydro-5H-cyclopentapyrimidin-2-ylamino]-phenyl}-cyclobutanecarboxylic acid methyl ester

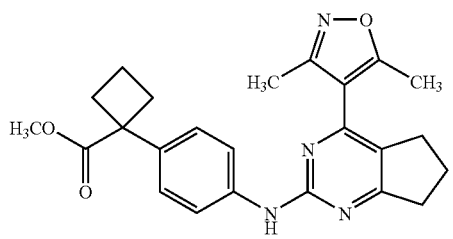

The title compound was prepared following the procedure as described in Example 24, step (ii) except 2-chloro-4-(3,5-dimethyl-isoxazol-4-yl)-6,7-dihydro-5H-cyclopentapyrimidine was used instead of 2-chloro-4-morpholin-4-yl-6,7-dihydro-5H-cyclopentapyrimidine. (42% yield).

$^1$H NMR (CDCl$_3$, 300 MHz): δ 7.60 (d, J=8.7 Hz, 2H), 7.26 (d, J=8.7 Hz, 2H), 7.10 (bs, 1H), 3.63 (s, 3H), 2.97 (t, J=7.5 Hz, 2H), 2.86-2.71 (m, 4H), 2.52-2.46 (m, 2H), 2.40 (s, 3H), 2.32 (s, 3H), 2.16-1.86 (m, 4H).

LC-MSD (ES+): (m/z) 419 [(M+H)$^+$, 100].

Step (iii): Synthesis of 1-{4-[4-(3,5-dimethyl-isoxazol-4-yl)-6,7-dihydro-5H-cyclopentapyrimidin-2-ylamino]-phenyl}-cyclobutanecarboxylic acid

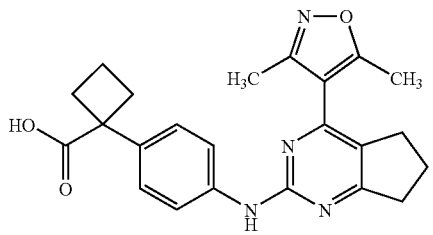

The title compound was prepared following the procedure as described in Example 4, step (v) (79% yield).

$^1$H NMR (CDCl$_3$, 300 MHz): δ 7.50 (d, J=8.7 Hz, 2H), 7.18 (d, J=8.7 Hz, 2H), 2.87 (t, J=7.5 Hz, 2H), 2.73-2.60 (m, 4H), 2.41-2.35 (m, 2H), 2.30 (s, 3H), 2.20 (s, 3H), 2.06-1.73 (m, 4H).

LC-MSD (ES+): (m/z) 405 [(M+H)$^+$, 100].

HPLC: Betasil ODS-3V C18, 20:80 [KH$_2$PO$_4$ (0.01 M, pH 3.2): CH$_3$CN], gradient, PDA 280 nm, R$_t$ 17.52 min, purity 98.08%.

Example 29

Synthesis of 1-[4-(2-phenoxy-6,7-dihydro-5H-cyclopentapyrimidin-4-ylamino)-phenyl]-cyclobutanecarboxylic acid

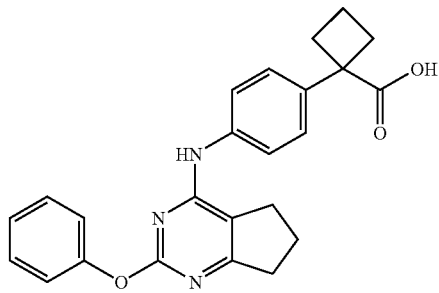

Step (i): Synthesis of 1-[4-(2-phenoxy-6,7-dihydro-5H-cyclopentapyrimidin-4-ylamino)-phenyl]-cyclobutanecarboxylic acid methyl ester

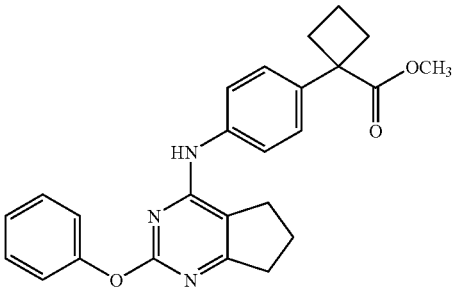

The title compound was prepared following a published procedure in the literature (D'Angelo, N. D. et al. Tetrahedron Letters, 2006, 47, 5045-5048). A mixture of 1-[4-(2-chloro-6,7-dihydro-5H-cyclopentapyrimidin-4-ylamino)-phenyl] cyclobutane carboxylic acid methyl ester (0.45 g, 1.26 mmol), phenol (0.23 g, 2.5 mmol), copper powder (0.010 g) and cesium carbonate (1.25 g, 3.8 mmol) in anhydrous dimethylformamide (3 mL) was stirred at a temperature in the range of 10° C. to 100° C. for 6 to 20 hours. The mixture was cooled to about 20 to 35° C. and diluted with water. The organics were extracted with EtOAc and the organic layer was washed with brine, dried over sodium sulfate, filtered and concentrated under reduced pressure. The crude was purified by column chromatography (silica gel) to afford white solid (43% yield).

$^1$H NMR (CDCl$_3$, 300 MHz): δ 7.44-7.39 (m, 2H), 7.29-7.18 (m, 5H), 7.06 (d, J=9.0 Hz, 2H), 6.20 (bs, 1H), 3.62 (s, 3H), 2.94 (t, J=7.5 Hz, 2H), 2.81-2.69 (m, 4H), 2.47-2.38 (m, 2H), 2.20-2.14 (m, 2H), 2.02-1.18 (m, 2H).

LC-MSD (ES+): (m/z) 416 [(M+H)$^+$, 100].

HPLC: Betasil ODS-3V C18, 30:70 [KH$_2$PO$_4$ (0.01 M, pH 3.2): CH$_3$CN], PDA 264 nm, R$_t$ 11.28 min, purity 97.25%.

Step (ii): Synthesis of 1-[4-(2-Phenoxy-6,7-dihydro-5H-cyclopentapyrimidin-4-ylamino)-phenyl]-cyclobutanecarboxylic acid

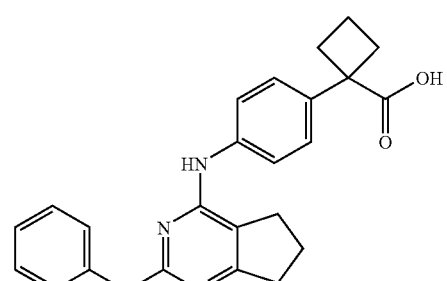

The title compound was prepared following the procedure as described in Example 4, step (v) (58% yield).

$^1$H NMR (CDCl$_3$, 300 MHz): δ 7.33-6.89 (m, 9H), 2.88 (t, J=7.5 Hz, 2H), 2.71-2.62 (m, 4H), 2.33-2.23 (m, 2H), 2.15-2.07 (m, 2H), 1.92-1.68 (m, 2H).

LC-MSD (ES+): (m/z) 402 [(M+H)$^+$, 100].

HPLC: Betasil ODS-3V C18, 30:70 [KH$_2$PO$_4$ (0.01 M, pH 3.2): CH$_3$CN], PDA 290 nm, R$_t$ 6.01 min, purity 95.58%.

Example 30

Synthesis of 1-[4-(2-morpholin-4-yl-6,7-dihydro-5H-cyclopentapyrimidin-4-ylamino)-phenyl]-cyclobutanecarboxylic acid cyclopentylamide

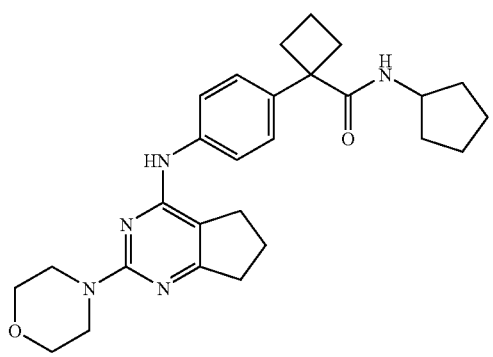

N-(3-Dimethylaminopropyl)-N'-ethylcarbodiimide hydrochloride (0.48 g, 2.5 mmol) was added to a mixture of 1-[4-(2-morpholin-4-yl-6,7-dihydro-5H-cyclopentapyrimidin-4-ylamino)-phenyl]-cyclobutanecarboxylic acid (0.5 g, 1.2 mmol), 1-hydroxybenzotrialzole (0.09 g, 0.65 mmol), diisopropylethylamine (0.43 mL, 2.5 mmol), and cyclopentylamine (0.13 mL, 1.3 mmol) in anhydrous dimethylformamide and stirred at a temperature in the range of 15° C. to 25° C. under $N_2$ for 16 hours. The reaction was quenched by addition of water. The precipitated solid was filtered, washed with water and dried in vacuo. The crude was purified by column chromatography (silica gel) to afford the title compound as a white solid (0.26 g, 45% yield).

$^1$H NMR (CDCl$_3$, 300 MHz): δ 7.60 (d, J=8.7 Hz, 2H), 7.22 (d, J=8.7 Hz, 2H), 6.12 (bs, 1H), 4.99 (bs, 1H), 4.13-4.09 (m, 1H), 3.82-3.70 (m, 8H), 2.84-2.64 (m, 6H), 2.46-2.35 (m, 2H), 2.16-1.83 (m, 6H), 1.52-1.46 (m, 4H), 1.26-1.11 (m, 2H).

LC-MSD (ES+): (m/z) 462 [(M+H)$^+$, 100].

HPLC: Betasil ODS-3V C18, 20:80 [KH$_2$PO$_4$ (0.01 M, pH 3.2): CH$_3$CN], gradient, PDA 228 nm, R$_t$ 11.67 min, purity 95.10%.

Example 31

Synthesis of 1-(4-{2-[4-(pyrrolidine-1-sulfonyl)-phenylamino]-6,7-dihydro-5H-cyclopentapyrimidin-4-ylamino}-phenyl)-cyclobutanecarboxylic acid

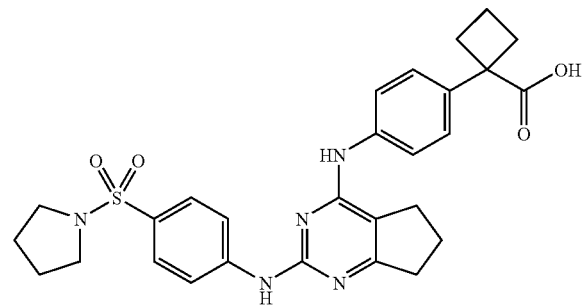

Step (i): Synthesis of 1-(4-{2-[4-(pyrrolidine-1-sulfonyl)-phenylamino]-6,7-dihydro-5H-cyclopentapyrimidin-4-ylamino}-phenyl)-cyclobutanecarboxylic acid methyl ester

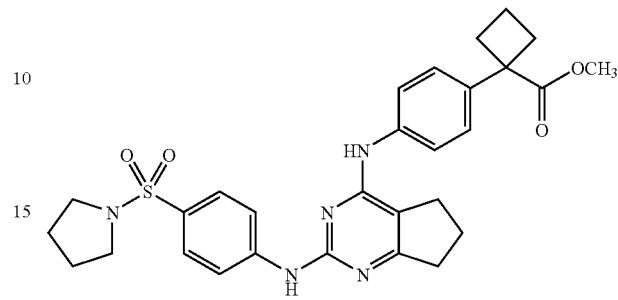

1-[4-(2-chloro-6,7-dihydro-5H-cyclopentapyrimidin-4-ylamino)-phenyl]cyclobutanecarboxylic acid methyl ester (0.36 g, 1 mmol) was added to a solution of 4-(pyrrolidine-1-sulfonyl)-phenylamine (0.24 g, 1.06 mmol) in anhydrous isopropanol (10 mL) and the mixture was stirred at a temperature in the range of 60° C. to 110° C. for 40 to 50 hours. The reaction was cooled to a temperature in the range of 15° C. to 25° C. The precipitated solid was filtered, washed with ether, and dried in vacuo to afford the title compound as a white solid (0.28 g, 54% yield).

$^1$H NMR (CDCl$_3$+CD$_3$OD, 300 MHz): δ 7.71 (d, J=8.7 Hz, 2H), 7.59 (d, J=8.7 Hz, 2H), 7.40 (d, J=8.4 Hz, 2H), 7.29 (d, J=8.4 Hz, 2H), 3.66 (s, 3H), 3.19-3.13 (m, 4H), 3.06 (t, J=7.8 Hz, 2H), 2.86-2.77 (m, 4H), 2.50-2.43 (m, 2H), 2.26-2.14 (m, 2H), 2.06-1.88 (m, 2H), 1.78-1.66 (m, 4H).

LC-MSD (ES+): (m/z) 548 [(M+H)$^+$, 100].

HPLC: Betasil ODS-3V C18, 20:80 [KH$_2$PO$_4$ (0.01 M, pH 3.2): CH$_3$CN], gradient, PDA 290 nm, R$_t$ 17.01 min, purity 97.73%.

Step (ii): Synthesis of 1-(4-{2-[4-(pyrrolidine-1-sulfonyl)-phenylamino]-6,7-dihydro-5H-cyclopentapyrimidin-4-ylamino}-phenyl)-cyclobutanecarboxylic acid

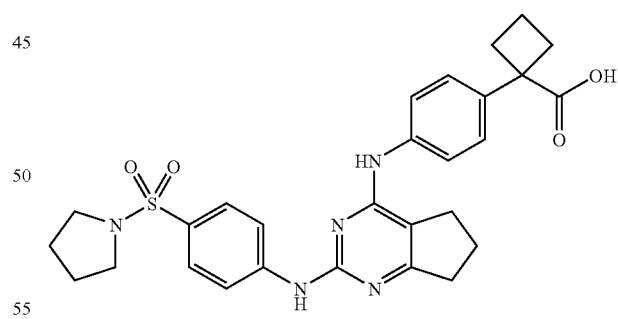

The title compound was prepared following the procedure as described in Example 4, step (v) (92% yield).

$^1$H NMR (CDCl$_3$+CD$_3$OD, 300 MHz): δ 7.54 (d, J=8.7 Hz, 2H), 7.40 (d, J=8.7 Hz, 2H), 7.28 (d, J=8.4 Hz, 2H), 7.15 (d, J=8.4 Hz, 2H), 3.02-2.97 (m, 4H), 2.75-2.58 (m, 6H), 2.36-2.25 (m, 2H), 2.04-1.88 (m, 2H), 1.89-1.70 (m, 2H), 1.57-1.51 (m, 4H).

LC-MSD (ES+): (m/z) 534 [(M+H)$^+$, 100].

HPLC: Betasil ODS-3V C18, 20:80 [KH$_2$PO$_4$ (0.01 M, pH 3.2): CH$_3$CN], gradient, PDA 298 nm, R$_t$ 13.74 min, purity 96.54%.

Example 32

Synthesis of 1-[4-(2-morpholin-4-yl-6,7-dihydro-5H-cyclopentapyrimidin-4-ylamino)-phenyl]-cyclobutanecarbonitrile

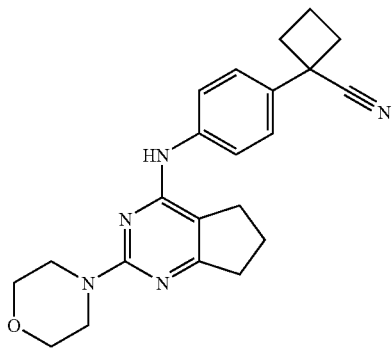

A solution of 2,4-dichloro-6,7-dihydro-5H-cyclopentapyrimidine (0.31 g, 1.7 mmol) and 1-(4-Amino-phenyl)-cyclobutanecarbonitrile (0.32 g, 1.8 mmol) and diisopropylethylamine (0.41 mL, 2.4 mmol) in anhydrous ethanol was heated at reflux for 35 hours. After cooling to a temperature in the range of 20° C. to 25° C., the mixture was concentrated under reduced pressure. The crude was diluted with water and ethyl acetate and stirred for 0.5 hours. The organic layer separated, washed with brine, dried over sodium sulfate, filtered and concentrated under reduced pressure. The semi-solid material was dissolved in anhydrous 1-butanol (4 mL) and morpholine (0.15 mL) was added at about 20 to 35° C. The mixture was stirred at a temperature in the range of 25° C. to 105° C. for 16 hours. After evaporation of volatiles under reduced pressure, the crude was purified by column chromatography (silica gel) to afford a light yellow solid (0.07 g, 39% yield).

$^1$H NMR (CDCl$_3$+CD$_3$OD, 300 MHz): δ 7.63 (d, J=8.4 Hz, 2H), 7.38 (d, J=8.4 Hz, 2H), 6.14 (s, 1H), 3.78-3.76 (m, 8H), 2.84-2.76 (m, 4H), 2.71-2.58 (m, 4H), 2.51-2.38 (m, 2H), 2.31-2.05 (m, 2H).

LC-MSD (ES+): (m/z) 376 [(M+H)$^+$, 100].

HPLC: Betasil ODS-3V C18, 20:80 [KH$_2$PO$_4$ (0.01 M, pH 3.2): CH$_3$CN], gradient, PDA 298 nm, R$_t$ 11.45 min, purity 96.75%.

Example 33

Synthesis of 1-[4-(4-phenoxy-6,7-dihydro-5H-cyclopentapyrimidin-2-ylamino)-phenyl]-cyclobutanecarboxylic acid methyl ester

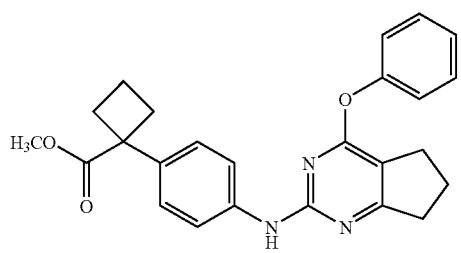

Step (i): Synthesis of 2-chloro-4-phenoxy-6,7-dihydro-5H-cyclopentapyrimidine

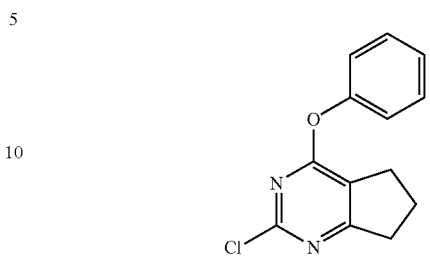

A mixture of 2,4-dichloro-6,7-dihydro-5H-cyclopentapyrimidine (0.45 g, 2.4 mmol), phenol (0.28 g, 3 mmol), cesium carbonate (0.97 g, 3 mmol) and copper powder (0.01 g) in anhydrous dimethylformamide (5 mL) was stirred at about 20 to 35° C. for 6 to 20 hours. The reaction was quenched by addition of water. The organics were extracted with EtOAc and the combined organic extracts were washed with brine, dried over sodium sulfate, filtered, and concentrated under reduced pressure. The crude was purified by column chromatography (silica gel) to afford the title compound as a white solid (0.31 g, 54%).

$^1$H NMR (CDCl$_3$, 300 MHz): δ 7.44-7.39 (m, 2H), 7.28-7.24 (m, 1H), 7.16-7.14 (m, 2H), 3.03-2.91 (m, 4H), 2.25-2.16 (m, 2H).

LC-MSD (ES+): (m/z) 247 [(M+H)$^+$, 100].

Step (ii): Synthesis of 1-[4-(4-phenoxy-6,7-dihydro-5H-cyclopentapyrimidin-2-ylamino)-phenyl]-cyclobutanecarboxylic acid methyl ester

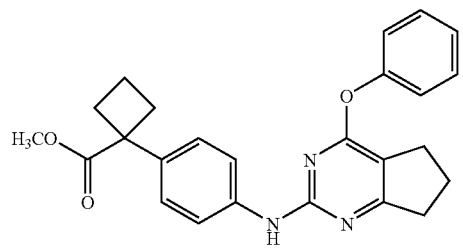

A mixture of 2-chloro-4-phenoxy-6,7-dihydro-5H-cyclopentapyrimidine (0.28 g, 1.1 mmol) and 1-(4-amino-phenyl) cyclobutanecarboxylic acid methyl ester (0.23 g, 1.11 mmol) in 1-butanol (3.0 mL) was stirred at a temperature in the range of 20° C. to 100° C. for 8 to 16 hours. Thereafter, the reaction was cooled to about 20 to 35° C. Anhydrous ether was added and the mixture was stirred for 1 hour at about 20 to 35° C. The separated solid was filtered, washed with ether, and dried in vacuum to afford the title compound as a white solid (0.38 g, 81% yield).

$^1$H NMR (CDCl$_3$, 300 MHz): δ 10.75 (s, 1H), 7.52-7.40 (m, 3H), 7.18-7.14 (m, 5H), 6.99 (m, 1H), 3.61 (s, 3H), 3.20-3.14 (m, 2H), 3.03-2.98 (m, 2H), 2.82-2.73 (m, 2H), 2.44-2.30 (m, 4H), 2.03-1.82 (m, 2H).

LC-MSD (ES+): (m/z) 416 [(M+H)$^+$, 100].

HPLC: Betasil ODS-3V C18, 30:70 [KH$_2$PO$_4$ (0.01 M, pH 3.2): CH$_3$CN], PDA 264 nm, R$_t$ 19.03 min, purity 99.85%.

Example 34

Synthesis of 1-{4-[4-(benzyl-ethyl-amino)-6,7-dihydro-5H-cyclopentapyrimidin-2-ylamino]-phenyl}-cyclobutanecarboxylic acid

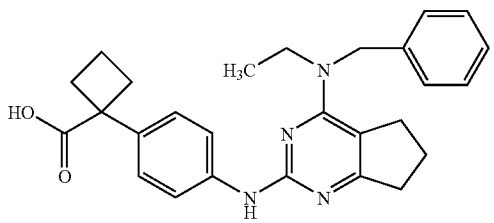

Step (i): Synthesis of benzyl-(2-chloro-6,7-dihydro-5H-cyclopentapyrimidin-4-yl)-ethyl-amine

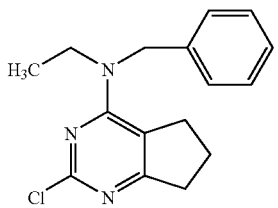

A mixture of 2,4-dichloro-6,7-dihydro-5H-cyclopentapyrimidine (0.4 g, 2.1 mmol), N-benzyl-ethylamine (0.35 mL, 2.3 mmol) and diisopropylethylamine (0.4 mL, 2.1 mmol) in anhydrous ethanol (5 mL) was heated at a temperature in the range of 20° C. to 90° C. for 18 hours. After cooling to about 20 to 35° C., the reaction mixture was concentrated under reduced pressure. The crude residue was diluted with ethyl acetate, washed with water, brine, dried over sodium sulfate, filtered and concentrated under reduced pressure to afford a light pink liquid (0.60 g, 98% yield).

$^1$H NMR (CDCl$_3$, 300 MHz): δ 7.44-7.08 (m, 5H), 4.80 (s, 2H), 3.62 (q, J=7.8 Hz, 2H), 3.28-2.76 (m, 4H), 2.24-2.08 (m, 2H), 1.26 (t, J=7.8 Hz, 3H).
LC-MSD (ES+): (m/z) 288 [(M+H)$^+$, 100].

Step (ii): Synthesis of 1-{4-[4-(benzyl-ethyl-amino)-6,7-dihydro-5H-cyclopentapyrimidin-2-ylamino]-phenyl}-cyclobutanecarboxylic acid methyl ester

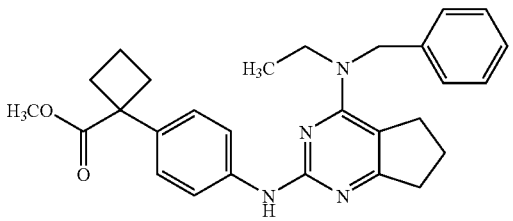

The title compound was prepared following the procedure as described in Example 24, step (ii) except benzyl-(2-chloro-6,7-dihydro-5H-cyclopentapyrimidin-4-yl)-ethyl-amine was used instead of 2-chloro-4-morpholin-4-yl-6,7-dihydro-5H-cyclopentapyrimidine.

$^1$H NMR (CDCl$_3$, 300 MHz): δ 7.74-7.0 (m, 9H), 4.85 (s, 2H), 3.78-3.62 (m, 5H), 3.18-1.71 (m, 12H), 1.28 (t, J=7.8 Hz, 3H).
LC-MSD (ES+): (m/z) 457 [(M+H)$^+$, 100].

Step (iii): Synthesis of 1-{4-[4-(benzyl-ethyl-amino)-6,7-dihydro-5H-cyclopentapyrimidin-2-ylamino]-phenyl}-cyclobutanecarboxylic acid

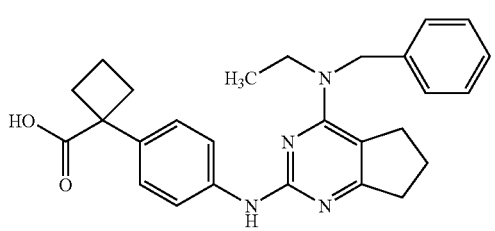

The title compound was prepared following the procedure as described in Example 24, step (iii).

$^1$H NMR (CDCl$_3$, 300 MHz): δ 7.33-7.0 (m, 9H), 4.75 (s, 2H), 3.60 (q, J=7.8 Hz, 2H), 2.83-2.63 (m, 6H), 2.36-2.26 (m, 2H), 2.0-1.72 (m, 4H), 1.15 (t, J=7.8 Hz, 3H).
LC-MSD (ES+): (m/z) 443 [(M+H)$^+$, 100].
HPLC: Betasil ODS-3V C18, 20:80 [KH$_2$PO$_4$ (0.01 M, pH 3.2): CH$_3$CN], gradient, PDA 264 nm, R$_t$ 13.17 min, purity 84.25%.

Example 35

Synthesis of sodium 1-{4-[ethyl-(2-morpholin-4-yl-6,7-dihydro-5H-cyclopentapyrimidin-4-yl)-amino]-phenyl}-cyclobutanecarboxylate

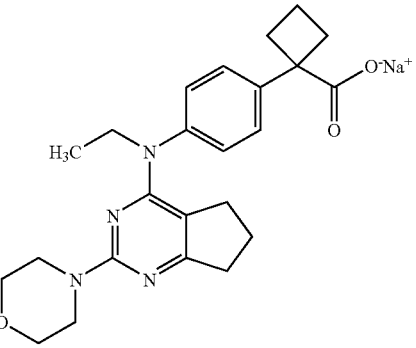

Step (i): Synthesis of 1-{4-[(2-chloro-6,7-dihydro-5H-cyclopentapyrimidin-4-yl)-ethyl-amino]-phenyl}-cyclobutanecarboxylic acid methyl ester

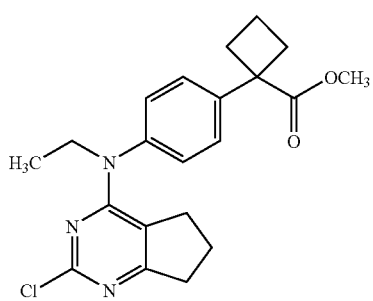

The title compound was prepared following the procedure as described in Example 4, step (iii) except 1-(4-ethylamino-phenyl)-cyclobutanecarboxylic acid methyl ester was used instead of 1-(4-amino-phenyl)-cyclobutanecarboxylic acid methyl ester (80% yield).

Step (ii): Synthesis of 1-{4-[ethyl-(2-morpholin-4-yl-6,7-dihydro-5H-cyclopentapyrimidin-4-yl)-amino]-phenyl}-cyclobutanecarboxylic acid methyl ester

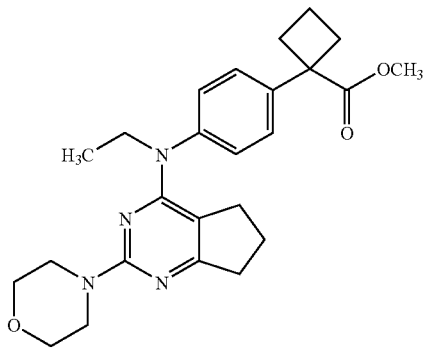

The title compound was prepared following the procedure as described in Example 4, step (iv) (90% yield).

$^1$H NMR (CDCl$_3$, 300 MHz): δ 7.13 (dd, J=6.6, 2.1 Hz, 2H), 6.57 (dd, J=6.6, 2.1 Hz, 2H), 3.76-3.62 (m, 11H), 3.15 (q, J=6.9 Hz, 2H), 2.89-2.72 (m, 6H), 2.48-2.42 (m, 2H), 2.01-1.82 (m, 4H), 1.26 (t, J=7.8 Hz, 3H).

LC-MSD (ES+): (m/z) 437 [(M+H)$^+$, 100].

Step (iii): Synthesis of Sodium 1-{4-[ethyl-(2-morpholin-4-yl-6,7-dihydro-5H-cyclopentapyrimidin-4-yl)-amino]-phenyl}-cyclobutanecarboxylate

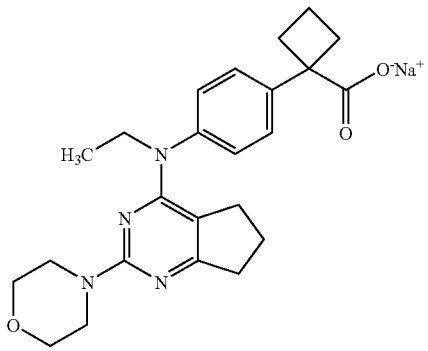

The title compound was prepared following the procedure as described in Example 4, step (v) followed by the procedure as described in Example 25 (39% yield).

$^1$H NMR (DMSO-d$_6$, 300 MHz): δ 7.23 (d, J=7.8 Hz, 1H), 6.98 (d, J=7.8H, 2H), 6.39 (d, J=7.8 Hz, 1H), 3.92-3.80 (q, J=7.2 Hz, 2H), 3.56-3.25 (m, 8H), 3.22-2.46 (m, 6H), 2.13-1.57 (m, 6H), 1.26 (t, J=7.2 Hz, 3H).

LC-MSD (ES+): (m/z) 423 [(M-Na+2H)$^+$, 100].

HPLC: Betasil ODS-3V C18, 30:70 [KH$_2$PO$_4$ (0.01 M, pH 3.2): CH$_3$CN], PDA 234 nm, R$_t$ 2.76 min, purity 93.40%.

Example 36

GATA Assay

Human HepG2 (ATCC) cells were grown in Eagle's Minimum Essential Media (MEM) containing 10% heat inactivated Fetal Bovine Serum (FBS) (Invitrogen) and 5 mL Penicillin-Streptomycin (Invitrogen) in T75 flasks (Corning) in a 37° C./5% CO$_2$ tissue culture incubator (Thermo Electron Corporation) prior to the study. 96-well plates (Corning) were seeded in MEM containing 10% FBS to yield ~50% confluency. The following day, cells were transfected using FuGENE 6 transfection reagent (Roche) and 550 ng/μL GATA Translucent Reporter Vector (Panomics) according the manufacturer's (Roche) protocol and incubated for about 10-19 h. The next day, the cells were treated with equal volumes of vehicle, dimethyl sulfoxide (DMSO) (Hybri-Max Sterile Filtered Sigma Aldrich) or compounds of formula (I) (in DMSO) diluted in MEM containing 1% FBS. The treated cells were incubated about 8-19 h. The next day the treatment media was removed and the cells were lysed and assayed for luciferase activity using the luciferase assay system (Promega) and using the Envision plate reader (Perkin Elmer). The lysates were also used to measure total protein content with the MicroBCA protein assay kit (Pierce) using the Multiskan Ascent plate reader at 570 nm. Luciferase values were normalized to total protein and fold induction was calculated.

Compounds that show an increase of ≧40% in luciferase levels at ≦20 μm concentration were considered as GATA activators.

| Example No. | GATA1 Activation (Fold Change Vs Control) | |
| --- | --- | --- |
| | 5μ | 10μ |
| 4 | 2.45 | 3.45 |
| 7 | 1.79 | 2.09 |
| 9 | 2.90 | 3.50 |
| 10 | 2.07 | 2.43 |
| 12 | 3.22 | 3.38 |
| 13 | 1.94 | 1.67 |

Example 37

Enzyme-Linked Immunosorbant Assay (ELISA)

Human HepG2 (ATCC) cells were grown in Eagle's Minimum Essential Media (MEM) Modified containing 10% heat inactivated Fetal Bovine Serum (FBS) (Invitrogen) and 5 mL Penicillin-Streptomycin (Invitrogen) in T75 flasks (Corning) in a 5% CO$_2$/37° C. the tissue culture incubator (Thermo Electron Corporation) prior to the study. 96-well plates (Corning) were seeded with 25,000 cells per well in MEM+ 10% FBS. The third day the media was changed to treatment media (MEM+1% FBS). Treatments were done with enough replicates for there to be triplicate samples for both the ELISA procedures as well as the MicroBCA procedure. The cells were treated with equal volumes of vehicle DMSO Hybri-Max Sterile Filtered (Sigma Aldrich) or compounds of formula (I) (prepared in DMSO) prepared in MEM containing 1% FBS at different concentrations for 24 & 48 hours. Cells from each time point were washed with 1×PBS and fixed with 100% methanol (Sigma Aldrich) for 10 minutes at about 20 to 35° C. or lysed with T-PER Tissue Protein Extraction Reagent (Pierce).

For the ELISAs, the methanol was removed and the plates were air dried and ready for use. The wells were blocked with 1×PBS containing 0.5% Bovine Serum Albumin fraction V (Fisher Scientific) with 200 µL/well for one hour at about 20 to 35° C. The block was removed and the wells were incubated with primary antibody (100 µL/well) for two hours at about 20 to 35° C. The primary antibodies are either ABCA1 (Santa Cruz Biotechnology) diluted 1:200 in 1×PBS+0.5% BSA or Anti-SRB1 (Novus Biologicals) diluted 1:2000 in 1×PBS+0.5% BSA. After the incubation, the wells were washed two times. Wells were washed with 1×PBS+0.5% BSA (200 µL/well) at about 20 to 35° C. for 5 minutes on an orbital shaker. After the washes wells were incubated in the secondary antibody, Goat α Rabbit IgG-HRP (Zymed, Invitrogen) (100 µL/well) diluted 1:5000 in 1×PBS+0.5% BSA, for one hour at about 20 to 35° C. Wells were washed as described above. For detection, 100 µL/well of color reagent (R&D systems) was added to the wells and the plates were incubated in the dark for 20 minutes. The color reaction was stopped with 50 µL/well 0.2N sulfuric acid (Fisher Scientific). The plates were read on the Multiskan Ascent plate reader at both 450 and 570 nm.

Cells for normalization with MicroBCA Protein assay were lysed by adding T-PER. The lysates were used to measure total protein content with the MicroBCA protein assay kit (Pierce) using the Multiskan Ascent plate reader at 570 nm.

The ELISA values were normalized total protein.

Compounds that showed an increase of ≧30% in ABCA1 and/or SR-B1 at ≦20 µm concentration are considered active compounds for RCT activity.

Example 38

Cholesterol Efflux Assay

Human THP-1 cells, monocytes (macrophages), from ATCC are plated in 24 well tissue culture plates (Corning) at a density of 2.2 E$^5$ cells per well in RMPI 1640 (ATCC) media containing 10% heat inactivated Fetal Bovine Serum (Invitrogen), 48.96 µM β-Mercaptoethanol (Sigma Aldrich), and 200 ng/mL Phorbol 12-myristate 13-acetate (PMA) (EMD Biosciences Inc). The macrophages were allowed to attach and adhere to the wells for 72 hours in a 37° C./5% CO$_2$ tissue culture incubator (Thermo Electron Corporation). The next day, the cells were labeled with RPMI 1640 containing 5% Lipid Reduced Fetal Bovine Serum (LRFBS) (Hyclone), 25 µg/mL human Acetylated Low Density Lipoprotein (Biomedical Technologies), and 1 µCI/mL 3H-Cholesterol (Perkin Elmer) for 24 hours. The following day, the wells were washed with 700 µL per well PBS, pH 7.4, and then 500 µL of RPMI 1640 media containing 0.2% Bovine Serum Albumin fraction V (Fisher Scientific) and either 20 µM of TO901317 (Cayman Chemical) or 20 µM compound of formula (I) or an equivalent volume of DMSO Hybri-Max Sterile Filtered (Sigma Aldrich) was added to the wells. The plates were incubated with compound treatments for 24 hours. The following day, the compound treatments were removed and 500 µL of RPMI 1640 media containing 0.2% BSA +/−25 µg/mL Apolipoprotein A-1, human (ApoA1) (Biomedical Technologies) was added to the wells. The plates were incubated with efflux media treatments for 24 hours. On the final day, the media was transferred to vials containing EcocintA (National Diagnostics USA) scintillation fluid; the cells were washed once in 1×PBS and then lysed with 500 µL lysis buffer containing 0.1 N NaOH (Fisher scientific) and 0.1% sodium lauryl sulfate (Sigma Aldrich). The lysates were also transferred to vials containing scintillation fluid. The samples were run on the TriCarb 2900 liquid scintillation counter (Perkin Elmer). Data was generated as counts per minute. The percentage cholesterol efflux was calculated by dividing media derived radioactivity by the sum of the radioactivity in the media and cells. The % efflux into BSA media was subtracted from the % efflux into the ApoA1 media for each treatment condition. The data are expressed as a percentage of the DMSO control.

Compounds that showed an increase of ≧30% at ≦30 µm concentration in cholesterol efflux are considered active RCT enhancing compounds.

Although several embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be exchanged in whole or in part.

All references cited in this specification are hereby incorporated by reference into this specification in their entireties.

The discussion of references herein is intended merely to summarize the assertions made by their authors and no admission is made that any reference constitutes prior art. Applicants reserve the right to challenge the accuracy and pertinence of the cited references.

We claim:
1. A compound of formula (I),

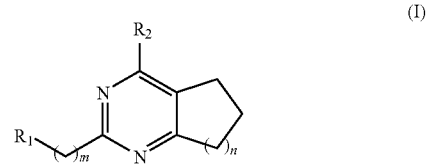

a stereoisomer of a compound formula (I), a pharmaceutically acceptable salt of a compound of formula (I), or a pharmaceutically acceptable salt of a stereoisomer of a compound of formula (I); wherein $R_1$ is —R, —OR, or —NR$^a$R$^b$;
$R_2$ is

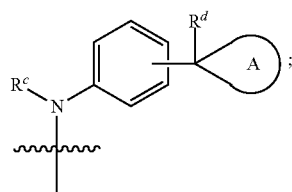

R is selected from an optionally substituted group selected from alkyl, cycloalkyl, aryl, heteroaryl or heterocyclyl, wherein one or more optional substituents on R are selected from halogen, hydroxy, cyano, alkyl, haloalkyl, cycloalkyl, —CO-alkyl, —(CH$_2$)$_r$—OH, —(CH$_2$)$_r$-alkoxy, aryl, heteroaryl, —(CH$_2$)$_r$SO$_2$NR$^f$R$^g$ or —(CH$_2$)$_r$SO$_2$R$^h$;

A is a 3- to 7-member cycloalkyl ring;

R$^a$ and R$^b$ are each independently selected from hydrogen, —(CH$_2$)$_r$-hydroxy, —(CH$_2$)$_r$-halogen, and an optionally substituted group selected from alkyl, —(CH$_2$)$_r$-cycloalkyl, —(CH$_2$)$_r$-heterocyclyl, —(CH$_2$)$_r$-aryl or —(CH$_2$)$_r$-heteroaryl, wherein one or more optional substituents on R$^a$ and R$^b$ are each independently selected from halogen, hydroxy, cyano, alkyl, haloalkyl, cycloalkyl, —CO-alkyl, —(CH$_2$)$_r$—OH, —(CH$_2$)$_r$-alkoxy, aryl, heteroaryl, —(CH$_2$)$_r$SO$_2$NR$^f$R$^g$ or —(CH$_2$)$_r$SO$_2$R$^h$; or R$^a$ and R$^b$ optionally combine with the nitrogen atom, to which they are attached, to form an optionally substituted 5- to 6-membered heterocyclic ring optionally having 1 to 3 additional hetero atoms or groups selected from nitrogen, oxygen, sulfur, SO$_2$ or CO, wherein one or more optional substituents on the 5- to 6-membered heterocyclic ring are selected from halogen, hydroxy, alkyl, haloalkyl, —CO-alkyl, —(CH$_2$)$_r$—OH or —(CH$_2$)$_r$-alkoxy; R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

R$^f$ and R$^g$ are each independently selected from hydrogen or an optionally substituted group selected from alkyl, cycloalkyl, alkoxy, aryl, heteroaryl or heterocyclyl, wherein one or more optional substituents on R$^f$ and R$^g$ are each independently selected from halogen, hydroxyl or alkyl;

R$^h$ is selected from alkyl, cycloalkyl, aryl, heterocyclyl or heteroaryl;

m is an integer from 0 to 2;

n is an integer from 1 to 3; and r is an integer from 0 to 3.

2. The compound as claimed in claim 1, having the formula (III),

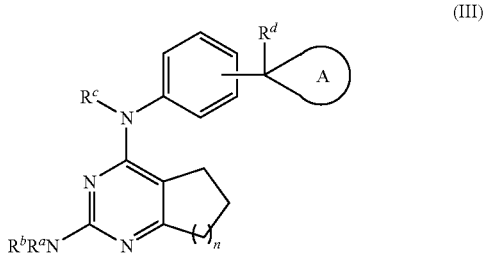

a stereoisomer of a compound of formula (III), a pharmaceutically acceptable salt of a compound of formula (III), or a pharmaceutically acceptable salt of a stereoisomer of a compound of formula (III).

3. The compound as claimed in claim 1, wherein

A is selected from cyclopropyl, cyclobutyl or cyclopentyl;

R$_1$ is selected from an optionally substituted group selected from alkyl, cycloalkyl, aryl, heteroaryl or heterocyclyl, wherein one or more optional substituents on R$_1$ are selected from halogen, hydroxy, cyano, alkyl, haloalkyl, cycloalkyl, —CO-alkyl, —(CH$_2$)$_r$—OH, —(CH$_2$)$_r$-alkoxy, aryl, heteroaryl, —(CH$_2$)$_r$SO$_2$NR$^f$R$^g$ or —(CH$_2$)$_r$SO$_2$R$^h$;

R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

R$^f$ and R$^g$ are each independently selected from hydrogen or an optionally substituted group selected from alkyl, cycloalkyl, alkoxy, aryl, heteroaryl or heterocyclyl, wherein one or more optional substituents on R$^f$ and R$^g$ are each independently selected from halogen, hydroxyl or alkyl;

R$^h$ is selected from alkyl, cycloalkyl, aryl, heterocyclyl or heteroaryl;

n is an integer selected from 1 or 2; and r is an integer from 0 to 3.

4. The compound as claimed in claim 2, wherein

A is selected from cyclopropyl, cyclobutyl or cyclopentyl;

R$^a$ is selected from hydrogen or (CH$_2$)$_r$-cycloalkyl;

R$^b$ is selected from hydrogen and an optionally substituted group selected from alkyl, —(CH$_2$)$_r$-cycloalkyl, —(CH$_2$)$_r$-heterocyclyl, —(CH$_2$)$_r$-aryl or —(CH$_2$)$_r$-heteroaryl, wherein one or more optional substituents on R$^b$ are selected from halogen, hydroxy, alkyl, haloalkyl, —CO-alkyl, —(CH$_2$)$_r$—OH, —(CH$_2$)$_r$-alkoxy, —(CH$_2$)$_r$SO$_2$NR$^f$R$^g$ or —(CH$_2$)$_r$SO$_2$R$^h$;

R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

R$^f$ and R$^g$ are each independently selected from hydrogen or an optionally substituted group selected from alkyl, cycloalkyl, alkoxy, aryl, heteroaryl or heterocyclyl, wherein one or more optional substituents on R$^f$ and R$^g$ are each independently selected from halogen, hydroxyl or alkyl;

R$^h$ is selected from alkyl, cycloalkyl, aryl, heterocyclyl or heteroaryl;

n is an integer selected from 1 or 2; and r is an integer from 0 to 3.

5. The compound as claimed in claim 4, wherein

R$^d$ is COOH.

6. The compound as claimed in claim 2, wherein

A is selected from cyclopropyl, cyclobutyl or cyclopentyl;

R$^a$ and R$^b$ combine with the nitrogen atom, to which they are attached, to form an optionally substituted 5- to 6-membered heterocyclic ring optionally having 1 to 3 additional hetero atoms or groups selected from nitrogen, oxygen, sulfur, SO$_2$ or CO, wherein one or more optional substituents on the 5- to 6-membered heterocyclic ring are selected from halogen, hydroxy, alkyl, haloalkyl or —CO-alkyl;

R$^c$ is selected from hydrogen or alkyl;

R$^d$ is selected from cyano, —(CH$_2$)$_r$—OH, —(CH$_2$)$_r$-alkoxy, alkyl, aryl, —NH-aryl, heteroaryl, —(CH$_2$)$_r$CO-alkyl, —(CH$_2$)$_r$COOR$^e$, —(CH$_2$)$_r$CONR$^f$R$^g$, —(CH$_2$)$_r$SO$_2$NR$^f$R$^g$ or —(CH$_2$)$_r$SO$_2$R$^h$;

R$^e$ is selected from hydrogen, alkyl, cycloalkyl, aryl, heterocyclyl or heteroaryl;

$R^f$ and $R^g$ are each independently selected from hydrogen or an optionally substituted group selected from alkyl, cycloalkyl, alkoxy, aryl, heteroaryl or heterocyclyl, wherein one or more optional substituents on $R^f$ and $R^g$ are each independently selected from halogen, hydroxyl or alkyl;

$R^h$ is selected from alkyl, cycloalkyl, aryl, heterocyclyl or heteroaryl;

n is an integer selected from 1 or 2; and r is an integer from 0 to 3.

7. The compound as claimed in claim 6, wherein $R^d$ is selected from —COOH;

$R^a$ and $R^b$ combine with the nitrogen atom, to which they are attached, to form an optionally substituted morpholinyl, piperidinyl, pyrrolidinyl, piperazinyl, thiomorpholinyl, dioxo-thiomorpholinyl, wherein one or more optional substituents on the heterocyclic ring formed may be selected from halogen, hydroxy, alkyl or —CO-alkyl.

8. A compound selected from:

1-[4-(2-Cyclopentyl-6,7-dihydro-5H-cyclopentapyrimidin-4-ylamino)-phenyl]-cyclopentanecarboxylic acid, 1-[4-(2-Cyclopentylmethyl-6,7-dihydro-5H-cyclopentapyrimidin-4-ylamino)-phenyl]-cyclopentanecarboxylic acid, 1-[4-(2-Cyclopentyl-6,7-dihydro-5H-cyclopentapyrimidin-4-ylamino)-phenyl]-cyclobutanecarboxylic acid, 1-[4-(2-Morpholin-4-yl-6,7-dihydro-5H-cyclopentapyrimidin-4-ylamino)-phenyl]-cyclobutanecarboxylic acid, 1-{4-[2-(4-Hydroxy-piperidin-1-yl)-6,7-dihydro-5H-cyclopentapyrimidin-4-ylamino]-phenyl}-cyclobutanecarboxylic acid, 1-[4-(2-Pyrrolidin-1-yl-6,7-dihydro-5H-cyclopentapyrimidin-4-ylamino)-phenyl]-cyclobutanecarboxylic acid, 1-{4-[2-(1-Methyl-1H-pyrazol-4-yl)-6,7-dihydro-5H-cyclopentapyrimidin-4-ylamino]-phenyl}-cyclobutanecarboxylic acid, 1-{4-[2-(4-Fluoro-phenyl)-6,7-dihydro-5H-cyclopentapyrimidin-4-ylamino]-phenyl}-cyclopentanecarboxylic acid, 1-{4-[2-(4-Acetyl-phenyl)-6,7-dihydro-5H-cyclopentapyrimidin-4-ylamino]-phenyl}-cyclobutanecarboxylic acid, 1-{4-[2-(3-Fluoro-phenylamino)-6,7-dihydro-5H-cyclopentapyrimidin-4-ylamino]-phenyl}-cyclobutanecarboxylic acid, 1-[4-(2-Cyclopentylamino-6,7-dihydro-5H-cyclopentapyrimidin-4-ylamino)-phenyl]-cyclobutanecarboxylic acid, 1-{4-[2-(Cyclopropylmethyl-amino)-6,7-dihydro-5H-cyclopentapyrimidin-4-ylamino]-phenyl}-cyclobutanecarboxylic acid, 1-{4-[2-(Bis-cyclopropylmethyl-amino)-6,7-dihydro-5H-cyclopentapyrimidin-4-ylamino]-phenyl}-cyclobutanecarboxylic acid, 1-{4-[2-(4-Methanesulfonyl-phenyl)-6,7-dihydro-5H-cyclopentapyrimidin-4-ylamino]-phenyl}-cyclobutanecarboxylic acid, 1-[4-(2-p-Tolyl-6,7-dihydro-5H-cyclopentapyrimidin-4-ylamino)-phenyl]-cyclobutanecarboxylic acid, 1-[4-(2-Phenyl-6,7-dihydro-5H-cyclopentapyrimidin-4-ylamino)-phenyl]-cyclobutanecarboxylic acid, 1-{4-[2-(2-Oxo-pyrrolidin-1-yl)-6,7-dihydro-5H-cyclopentapyrimidin-4-ylamino]-phenyl}-cyclobutanecarboxylic acid methyl ester, 1-{4-[2-(6-Methyl-pyridin-3-yl)-6,7-dihydro-5H-cyclopentapyrimidin-4-ylamino]-phenyl}-cyclobutanecarboxylic acid, {1-[4-(2-Morpholin-4-yl-6,7-dihydro-5H-cyclopentapyrimidin-4-ylamino)-phenyl]-cyclobutyl}-methanol, 1-[4-(2-Morpholin-4-yl-6,7-dihydro-5H-cyclopentapyrimidin-4-ylamino)-phenyl]-cyclopentanecarboxylic acid, {1-[4-(2-Morpholin-4-yl-6,7-dihydro-5H-cyclopentapyrimidin-4-ylamino)-phenyl]-cyclopentyl}-methanol, Sodium 1-[4-(2-morpholin-4-yl-6,7-dihydro-5H-cyclopentapyrimidin-4-ylamino)-phenyl]-cyclobutanecarboxylate, 1-{4-[2-(4,4-Difluoro-piperidin-1-yl)-6,7-dihydro-5H-cyclopentapyrimidin-4-ylamino]-phenyl}-cyclobutanecarboxylic acid 1-[4-(2-Morpholin-4-yl-5,6,7,8-tetrahydro-quinazolin-4-ylamino)-phenyl]-cyclobutanecarboxylic acid, 1-[4-(2-Phenoxy-6,7-dihydro-5H-cyclopentapyrimidin-4-ylamino)-phenyl]-cyclobutanecarboxylic acid, 1-[4-(2-Morpholin-4-yl-6,7-dihydro-5H-cyclopentapyrimidin-4-ylamino)-phenyl]-cyclobutanecarboxylic acid cyclopentylamide, 1-(4-{2-[4-(Pyrrolidine-1-sulfonyl)-phenylamino]-6,7-dihydro-5H-cyclopentapyrimidin-4-ylamino}-phenyl)-cyclobutanecarboxylic acid, 1-[4-(2-Morpholin-4-yl-6,7-dihydro-5H-cyclopentapyrimidin-4-ylamino)-phenyl]-cyclobutanecarbonitrile, Sodium 1-{4-[ethyl-(2-morpholin-4-yl-6,7-dihydro-5H-cyclopentapyrimidin-4-yl)-amino]-phenyl}-cyclobutanecarboxylate, a stereoisomer, a pharmaceutically acceptable salt, or a pharmaceutically acceptable salt of a stereoisomer thereof.

9. The compound as claimed in claim 8, wherein the compound is

1-[4-(2-Cyclopentyl-6,7-dihydro-5H-cyclopentapyrimidin-4-ylamino)-phenyl]-cyclopentanecarboxylic acid, 1-[4-(2-Cyclopentylmethyl-6,7-dihydro-5H-cyclopentapyrimidin-4-ylamino)-phenyl]-cyclopentanecarboxylic acid, 1-[4-(2-Cyclopentyl-6,7-dihydro-5H-cyclopentapyrimidin-4-ylamino)-phenyl]-cyclobutanecarboxylic acid, 1-{4-[2-(4-Fluoro-phenyl)-6,7-dihydro-5H-cyclopentapyrimidin-4-ylamino]-phenyl}-cyclopentanecarboxylic acid, 1-{4-[2-(4-Acetyl-phenyl)-6,7-dihydro-5H-cyclopentapyrimidin-4-ylamino]-phenyl}-cyclobutanecarboxylic acid, 1-{4-[2-(4-Methanesulfonyl-phenyl)-6,7-dihydro-5H-cyclopentapyrimidin-4-ylamino]-phenyl}-cyclobutanecarboxylic acid, 1-[4-(2-p-Tolyl-6,7-dihydro-5H-cyclopentapyrimidin-4-ylamino)-phenyl]-cyclobutanecarboxylic acid, 1-[4-(2-Phenyl-6,7-dihydro-5H-cyclopentapyrimidin-4-ylamino)-phenyl]-cyclobutanecarboxylic acid, a stereoisomer, a pharmaceutically acceptable salt, or a pharmaceutically acceptable salt of a stereoisomer thereof.

10. The compound as claimed in claim 8, wherein the compound is

1-[4-(2-Morpholin-4-yl-6,7-dihydro-5H-cyclopentapyrimidin-4-ylamino)-phenyl]-cyclobutanecarboxylic acid, 1-{4-[2-(4-Hydroxy-piperidin-1-yl)-6,7-dihydro-5H-cyclopentapyrimidin-4-ylamino]-phenyl}-cyclobutanecarboxylic acid, 1-[4-(2-Pyrrolidin-1-yl-6,7-dihydro-5H-cyclopentapyrimidin-4-ylamino)-phenyl]-cyclobutanecarboxylic acid, 1-{4-[2-(1-Methyl-1H-pyrazol-4-yl)-6,7-dihydro-5H-cyclopentapyrimidin-4-ylamino]-phenyl}-cyclobutanecarboxylic acid, 1-{4-[2-(2-Oxo-pyrrolidin-1-yl)-6,7-dihydro-5H-cyclopentapyrimidin-4-ylamino]-phenyl}-cyclobutanecarboxylic acid methyl ester, 1-{4-[2-(6-Methyl-pyridin-3-yl)-6,7-dihydro-5H-cyclopentapyrimidin-4-ylamino]-phenyl}-cyclobutanecarboxylic acid, {1-[4-(2-Morpholin-4-yl-6,7-dihydro-5H-cyclopentapyrimidin-4-ylamino)-phenyl]-cyclobutyl}-methanol, 1-[4-(2-Morpholin-4-yl-6,7-dihydro-5H-cyclopentapyrimidin-4-ylamino)-phenyl]-cyclopentanecarboxylic acid, {1-[4-(2-Morpholin-4-yl-6,7-dihydro-5H-cyclopentapyrimidin-4-ylamino)-phenyl]-cyclopentyl}-methanol, Sodium 1-[4-(2-morpholin-4-yl-6,7-dihydro-5H-cyclopentapyrimidin-4-ylamino)-phenyl]-cyclobutanecarboxylate, 1-{4-[2-(4,4-Difluoro-piperidin-1-yl)-6,7-dihydro-5H-cyclopentapyrimidin-4-ylamino]-phenyl}-cyclobutanecarboxylic acid, 1-[4-(2-Morpholin-4-yl-5,6,7,8-tetrahydro-quinazolin-4-ylamino)-phenyl]-cyclobutanecarboxylic acid, 1-[4-(2-Morpholin-4-yl-6,7-dihydro-5H-cyclopentapyrimidin-4-ylamino)-phenyl]-cyclobutanecarboxylic acid cyclopentylamide, Sodium 1-{4-[ethyl-(2-morpholin-4-yl-6,7-dihydro-5H-cyclopentapyrimidin-4-yl)-amino]-phenyl}-cyclobutanecarboxylate, a stereoisomer, a pharmaceutically acceptable salt, or a pharmaceutically acceptable salt of a stereoisomer thereof.

11. The compound as claimed in claim 8, wherein the compound is

1-{4-[2-(3-Fluoro-phenylamino)-6,7-dihydro-5H-cyclopentapyrimidin-4-ylamino]-phenyl}-cyclobutanecarboxylic acid, 1-[4-(2-Cyclopentylamino-6,7-dihydro-5H-cyclopentapyrimidin-4-ylamino)-phenyl]-cyclobutanecarboxylic acid, 1-{4-[2-(Cyclopropylmethyl-amino)-6,7-dihydro-5H-cyclopentapyrimidin-4-ylamino]-phenyl}-cyclobutanecarboxylic acid, 1-{4-[2-(Bis-cyclopropylmethyl-amino)-6,7-dihydro-5H-cyclopentapyrimidin-4-ylamino]-phenyl}-cyclobutanecarboxylic acid, 1-(4-{2-[4-(Pyrrolidine-1-sulfonyl)-phenylamino]-6,7-dihydro-5H-cyclopentapyrimidin-4-ylamino}-phenyl)-cyclobutanecarboxylic acid, a stereoisomer, a pharmaceutically acceptable salt, or a pharmaceutically acceptable salt of a stereoisomer thereof.

12. The compound as claimed in claim 8, wherein the compound is

1-[4-(2-Phenoxy-6,7-dihydro-5H-cyclopentapyrimidin-4-ylamino)-phenyl]-cyclobutanecarboxylic acid, 1-[4-(2-Morpholin-4-yl-6,7-dihydro-5H-cyclopentapyrimidin-4-ylamino)-phenyl]-cyclobutanecarbonitrile, a stereoisomer, a pharmaceutically acceptable salt, or a pharmaceutically acceptable salt of a stereoisomer thereof.

13. The compound as claimed in claim 8, wherein the compound is

1-{4-[2-(2-Oxo-pyrrolidin-1-yl)-6,7-dihydro-5H-cyclopentapyrimidin-4-ylamino]-phenyl}-cyclobutanecarboxylic acid methyl ester, {1-[4-(2-Morpholin-4-yl-6,7-dihydro-5H-cyclopentapyrimidin-4-ylamino)-phenyl]-cyclobutyl}-methanol, 1-[4-(2-Morpholin-4-yl-6,7-dihydro-5H-cyclopentapyrimidin-4-ylamino)-phenyl]-cyclopentanecarboxylic acid, {1-[4-(2-Morpholin-4-yl-6,7-dihydro-5H-cyclopentapyrimidin-4-ylamino)-phenyl]-cyclopentyl}-methanol, Sodium 1-[4-(2-morpholin-4-yl-6,7-dihydro-5H-cyclopentapyrimidin-4-ylamino)-phenyl]-cyclobutanecarboxylate, 1-{4-[2-(4,4-Difluoro-piperidin-1-yl)-6,7-dihydro-5H-cyclopentapyrimidin-4-ylamino]-phenyl}-cyclobutanecarboxylic acid, 1-[4-(2-Morpholin-4-yl-5,6,7,8-tetrahydro-quinazolin-4-ylamino)-phenyl]-cyclobutanecarboxylic acid, Sodium 1-{4-[ethyl-(2-morpholin-4-yl-6,7-dihydro-5H-cyclopentapyrimidin-4-yl)-amino]-phenyl}-cyclobutanecarboxylate.

a stereoisomer, a pharmaceutically acceptable salt, or a pharmaceutically acceptable salt of a stereoisomer thereof.

14. A pharmaceutical composition comprising a pharmaceutically acceptable carrier and at least one compound according to claim 1, a stereoisomer of a compound of formula (I), a pharmaceutically acceptable salt of a compounds of formula (I), or a pharmaceutically acceptable salt of a stereoisomer of a compound of formula (I).

15. A pharmaceutical composition comprising a pharmaceutically acceptable carrier and at least one compound according to claim 8.

* * * * *